(12) United States Patent
Kim et al.

(10) Patent No.: US 9,362,506 B2
(45) Date of Patent: Jun. 7, 2016

(54) HETEROCYCLIC COMPOUND AND ORGANIC LIGHT-EMITTING DEVICE INCLUDING THE SAME

(71) Applicant: Samsung Display Co., Ltd., Yongin, Gyeonggi-Do (KR)

(72) Inventors: Young-Kook Kim, Yongin (KR); Seok-Hwan Hwang, Yongin (KR); Yoon-Hyun Kwak, Yongin (KR); Sun-Young Lee, Yongin (KR); Hye-Jin Jung, Yongin (KR); Jin-O Lim, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 0 days.

(21) Appl. No.: 14/302,909

(22) Filed: Jun. 12, 2014

(65) Prior Publication Data

US 2014/0291654 A1 Oct. 2, 2014

Related U.S. Application Data

(62) Division of application No. 13/210,599, filed on Aug. 16, 2011, now Pat. No. 8,815,417.

(30) Foreign Application Priority Data

Oct. 25, 2010 (KR) .......................... 10-2010-0104186

(51) Int. Cl.
*H01L 51/50* (2006.01)
*H01L 51/00* (2006.01)
(Continued)

(52) U.S. Cl.
CPC .......... *H01L 51/0052* (2013.01); *C07D 209/80* (2013.01); *C07D 401/04* (2013.01);
(Continued)

(58) Field of Classification Search
None
See application file for complete search history.

(56) References Cited

U.S. PATENT DOCUMENTS

| 5,635,308 A | 6/1997 | Inoue et al. |
| 5,645,948 A | 7/1997 | Shi et al. |

(Continued)

FOREIGN PATENT DOCUMENTS

| EP | 1 955 750 | 8/2008 |
| JP | 8-12600 | 1/1996 |

(Continued)

*Primary Examiner* — Gregory Clark
(74) *Attorney, Agent, or Firm* — Robert S. Bushnell, Esq.

(57) ABSTRACT

A heterocyclic compound represented by Formula 1 below and an organic light-emitting device including the heterocyclic compound:

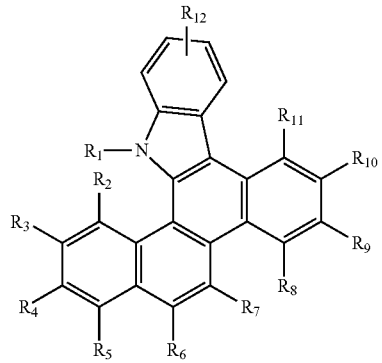

Formula 1 wherein $R_1$ to $R_{12}$ are defined as in the specification.

21 Claims, 1 Drawing Sheet

(51) Int. Cl.

| | | |
|---|---|---|
| *C07D 209/80* | (2006.01) | |
| *C07D 401/04* | (2006.01) | |
| *C07D 401/10* | (2006.01) | |
| *C07D 401/12* | (2006.01) | |
| *C07D 401/14* | (2006.01) | |
| *C07D 403/04* | (2006.01) | |
| *C07D 403/10* | (2006.01) | |
| *C07D 403/14* | (2006.01) | |
| *C07D 405/04* | (2006.01) | |
| *C07D 409/04* | (2006.01) | |
| *C07D 409/14* | (2006.01) | |
| *C07D 413/04* | (2006.01) | |
| *C07D 413/10* | (2006.01) | |
| *C07D 417/10* | (2006.01) | |
| *C07D 471/04* | (2006.01) | |
| *C07D 487/04* | (2006.01) | |

(52) U.S. Cl.
CPC ............ *C07D401/10* (2013.01); *C07D 401/12* (2013.01); *C07D 401/14* (2013.01); *C07D 403/04* (2013.01); *C07D 403/10* (2013.01); *C07D 403/14* (2013.01); *C07D 405/04* (2013.01); *C07D 409/04* (2013.01); *C07D 409/14* (2013.01); *C07D 413/04* (2013.01); *C07D 413/10* (2013.01); *C07D 417/10* (2013.01); *C07D 471/04* (2013.01); *C07D 487/04* (2013.01); *H01L 51/0058* (2013.01); *H01L 51/0061* (2013.01); *H01L 51/0068* (2013.01); *H01L 51/0072* (2013.01); *H01L 51/0073* (2013.01); *H01L 51/5012* (2013.01); *H01L 51/5076* (2013.01); *H01L 51/5092* (2013.01); *H01L 51/0054* (2013.01); *H01L 51/0059* (2013.01); *H01L 51/0069* (2013.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 2006/0124924 | A1 | 6/2006 | Suh et al. |
| 2006/0210830 | A1 | 9/2006 | Funahashi et al. |
| 2007/0155991 | A1 | 7/2007 | Funahashi |
| 2008/0268283 | A1 | 10/2008 | Funahashi |
| 2008/0306303 | A1 | 12/2008 | Rostovtsev et al. |
| 2010/0032658 | A1 | 2/2010 | Lee et al. |
| 2010/0127618 | A1 | 5/2010 | Ohrui et al. |

FOREIGN PATENT DOCUMENTS

| | | |
|---|---|---|
| JP | 2000-003782 | 1/2000 |
| JP | 2008-290999 | 12/2008 |
| KR | 10-2010-0007780 | 1/2010 |
| WO | 2010114264 | 10/2010 |

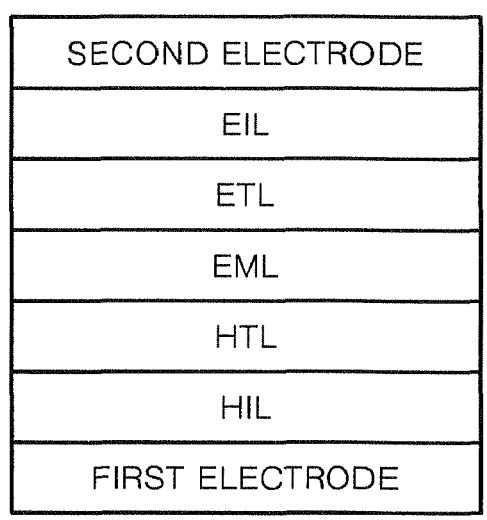

HETEROCYCLIC COMPOUND AND ORGANIC LIGHT-EMITTING DEVICE INCLUDING THE SAME

CROSS-REFERENCE TO RELATED PATENT APPLICATION

This application is a divisional application of the prior application Ser. No. 13/210,599 entitled HETEROCYCLIC COMPOUND AND ORGANIC LIGHT-EMITTING DEVICE INCLUDING THE SAME filed in the U.S. Patent & Trademark Office on 16 Aug. 2011 and assigned to the assignee of the present invention. Furthermore, this application claims the benefit of Korean Patent Application No. 10-2010-0104186, filed on Oct. 25, 2010, in the Korean Intellectual Property Office, the disclosure of which is incorporated herein in its entirety by reference.

BACKGROUND OF THE INVENTION

1. Field of the Invention

The present invention relates to a heterocyclic compound represented by Formula 1 and an organic light-emitting device including the heterocyclic compound.

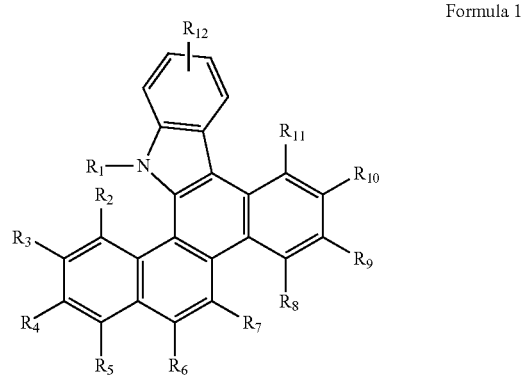

Formula 1

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multicolored displays. Thus, much research into such organic light-emitting devices has been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

Anthracene derivatives are widely known as materials for organic light-emission layer materials. Alq3, 2,2',2"-(1,3,5-phenylene)tris-(1-phenyl)-1H-benzimidazol (TPBI), 2-biphenyl-4-yl-5-(4-tert-butyl-phenyl)-[1,3,4]oxadiazole (PBD), perfluoronated chemical (PF-6P), and 2,5-bis(6'-(2', 2"-bipyridyl))-1,1-dimethyl-3,4-diphenylsiylol (PyPySPyPy) are known as electron transport materials. However, these materials are not yet satisfactory to meet requirements for organic light-emitting devices in terms of efficiency and lifespan, thereby improvement in this regard still being necessary.

SUMMARY OF THE INVENTION

The present invention provides a heterocyclic compound having good electrical characteristics, charge transporting capabilities, light-emission capabilities, and a high glass-transition temperature that is high enough to prevent crystallization.

The present invention provides an organic light-emitting device including the heterocyclic compound.

The present invention provides a flat panel display device including the organic light-emitting device.

The present invention provides an organic light-emitting device including at least one layer containing the heterocyclic compound, wherein the at least one layer is formed using a wet process.

According to an aspect of the present invention, there is provided a heterocyclic compound represented by Formula 1 below:

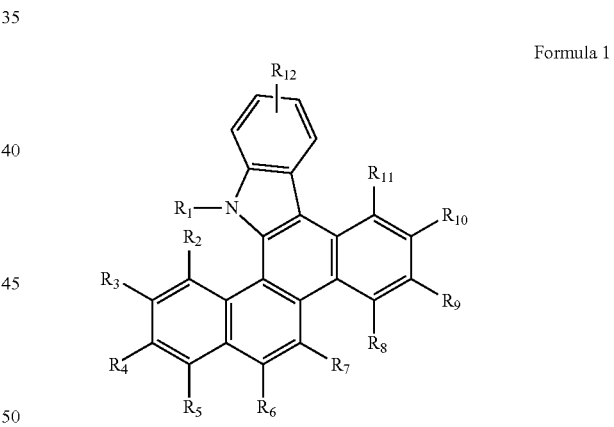

Formula 1 wherein, in Formula 1, $R_1$ to $R_{12}$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group, a halogen atom, a cyano group, a nitro group, a hydroxyl group, and a carboxyl group, wherein $R_6$ and $R_7$ may be respectively linked to binding sites indicated by ** and *, respectively, in Formula 2 below:

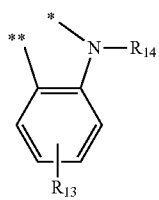

Formula 2 wherein, in Formula 2, $R_{13}$ and $R_{14}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_2$-$C_{60}$ heterocyclic group, a substituted or unsubstituted $C_2$-$C_{60}$ heterocyclic group, a halogen atom, a cyano group, a nitro group, a hydroxyl group, or a carboxyl group; and two adjacent substituents among $R_1$ to $R_{14}$ are optionally linked to each other to form a ring.

The heterocyclic compound of Formula 1 may be one of the compounds below:

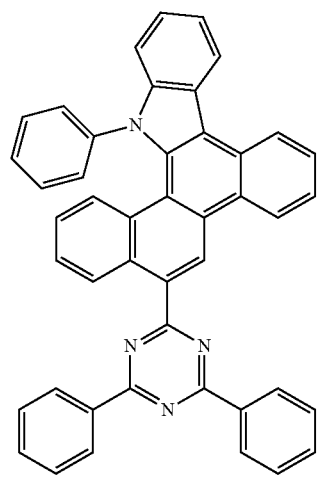

7

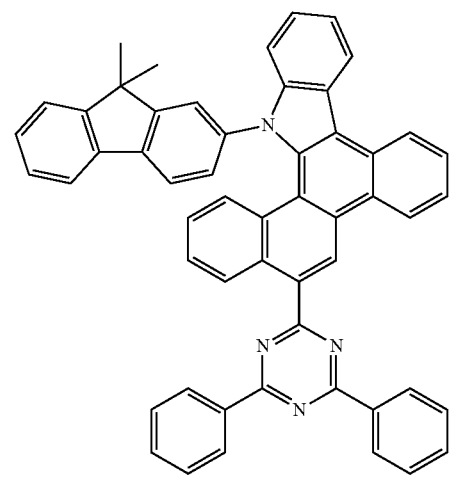

8

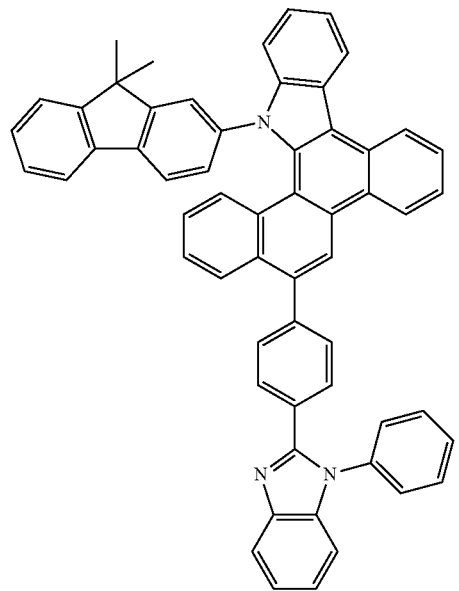

13

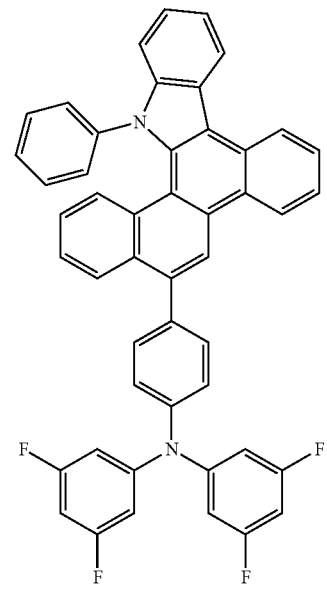

29

-continued
37
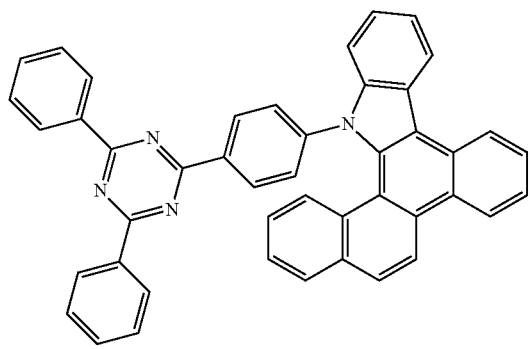
64
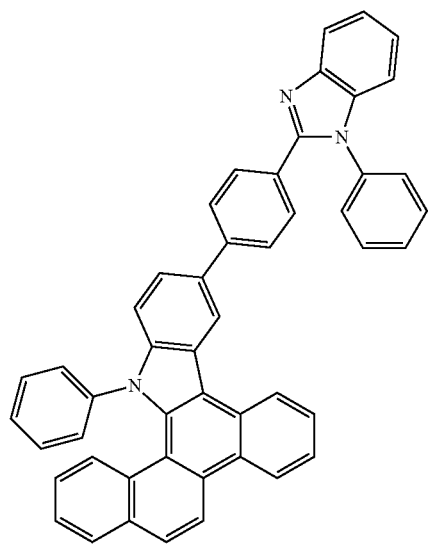
65
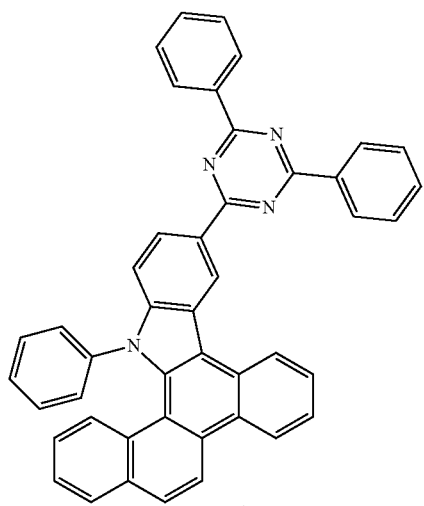
68
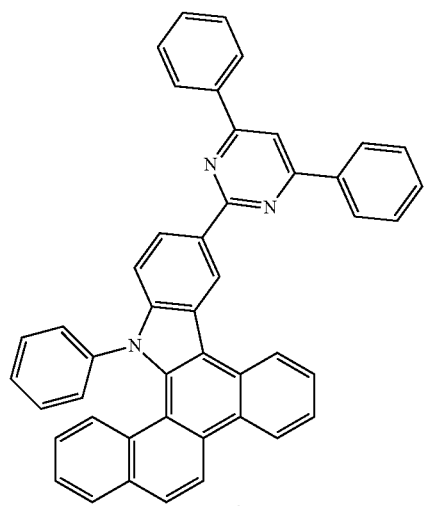
69
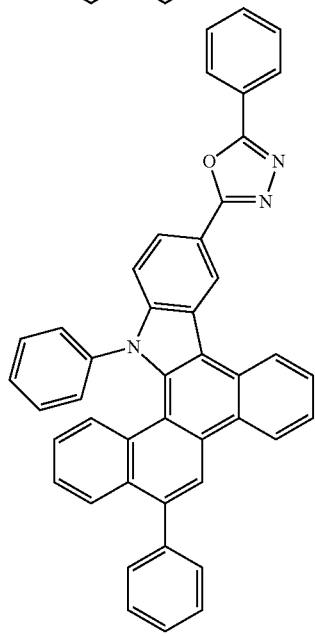
79
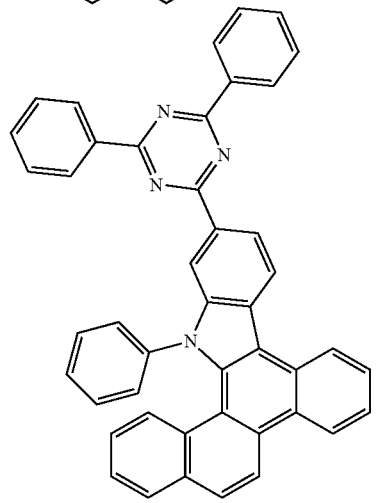

-continued
86
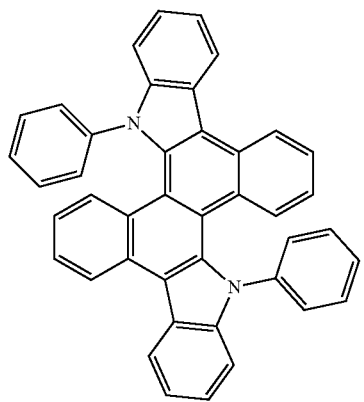
94
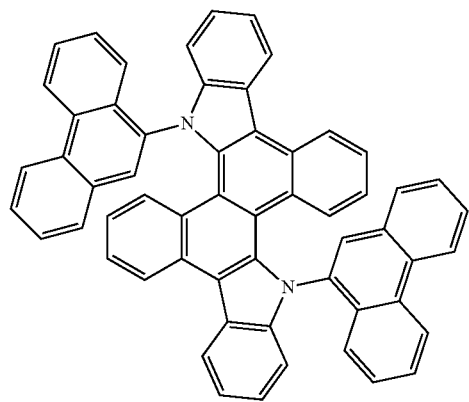
99
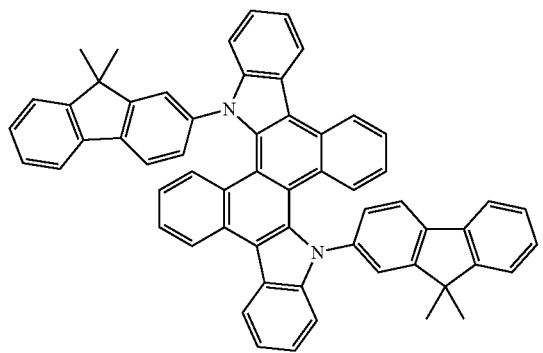
107
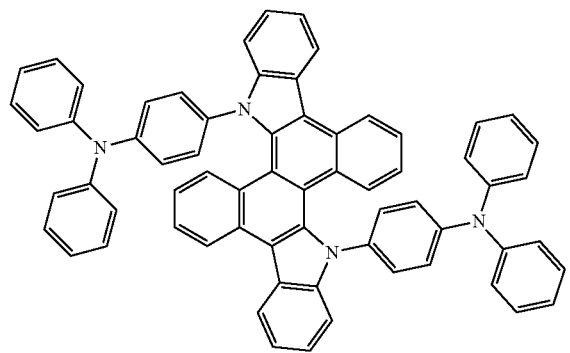
109
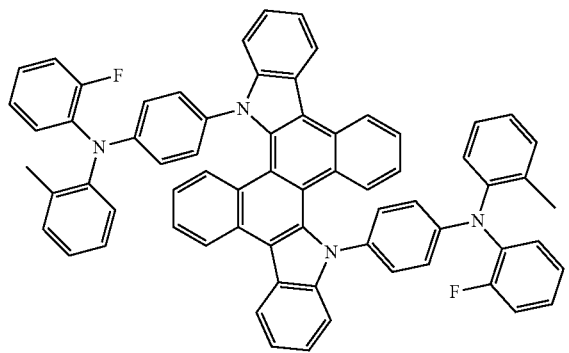
116
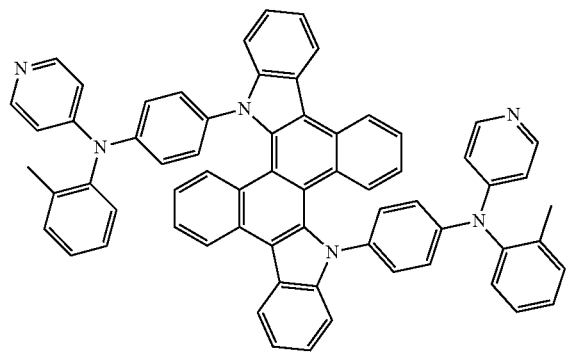
119
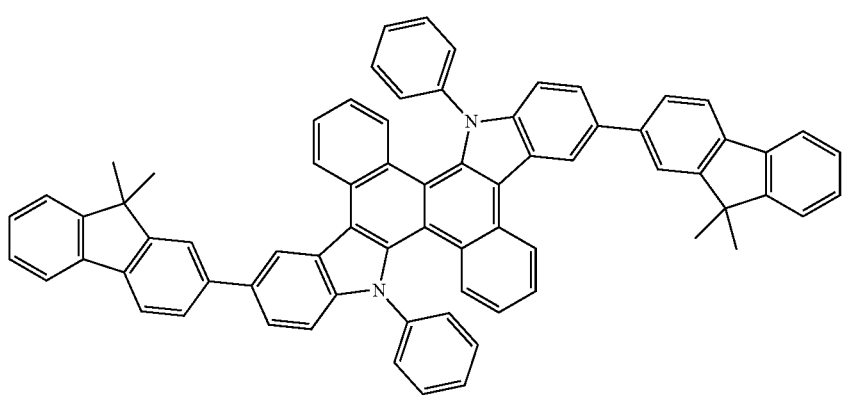

According to another aspect of the present invention, there is provided an organic light-emitting device including: a first electrode; a second electrode; and an organic layer between the first electrode and the second electrode, wherein the organic layer includes the heterocyclic compound represented by Formula 1 above.

The organic layer may include an emission layer including the heterocyclic compound of Formula 1 above as a host for a fluorescence or phosphorescence device.

The organic layer may include an emission layer including the heterocyclic compound of Formula 1 above as a dopant for a fluorescence device.

The organic layer may include an electron injection layer or an electron transport layer.

The organic layer may include a single layer having both an electron injection function and an electron transport function.

In some embodiments the organic layer may include an emission layer, an electron injection layer, or an electron transport layer. The emission layer, the electron injection layer, or the electron transport layer may include the heterocyclic compound of Formula 1 above. The emission layer may include an anthracene compound, an arylamine compound, or a styryl compound.

In some other embodiments the organic layer may include an emission layer, an electron injection layer, or an electron transport layer. The emission layer, the electron injection layer, or the electron transport layer may include the heterocyclic compound of Formula 1 above. The emission layer may include red, green, blue, and white emission layers one of which includes a phosphorescent compound.

According to another aspect of the present invention, there is provided an organic light-emitting device including: a first electrode; a second electrode; and an organic layer between the first electrode and the second electrode, wherein the organic layer includes at least one layer comprising the heterocyclic compound of Formula 1 above, the at least one layer being formed using a wet process.

According to another aspect of the present invention, there is provided a flat panel display device including the organic light-emitting device described above, wherein the first electrode of the organic light-emitting device is electrically connected to a source electrode or a drain electrode of a thin-film transistor.

BRIEF DESCRIPTION OF THE DRAWING

The above and other features and advantages of the present invention will become more apparent by describing in detail exemplary embodiments thereof with reference to the attached drawing in which:

FIG. 1 is a diagram of the structure of an organic light-emitting device according to an embodiment of the present invention.

DETAILED DESCRIPTION OF THE INVENTION

Organic light-emitting devices manufactured using anthracene derivatives, for example, a compound of phenylanthracene dimer or trimer, as organic emission layer materials are widely known. However, such organic light-emitting devices have a narrow energy gap and lower blue-light color purity since two or three oligomeric species of anthracene are linked by conjugation. In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 positions or using a diphenylanthracene compound including an aryl group substituted for a phenyl group at m-position have been introduced. However, these organic light-emitting devices have a lower light-emission efficiency. Organic light-emitting devices may also be manufactured using nathphalene-substituted monoanthracene derivatives. However, the light-emission efficiency thereof is low at about 1 cd/A, and thus such organic light-emitting devices are not suitable for practical use. Furthermore, organic light-emitting devices may be manufactured using phenylanthracene compounds including aryl substituents at m-position. Such compounds have good thermal resistance but lead to an unsatisfactorily low light-emission efficiency of about 2 cd/A, and thus further improvement is required in this regard.

The present invention will now be described more fully with reference to the accompanying drawings, in which exemplary embodiments of the invention are shown.

An aspect of the present invention includes a heterocyclic compound represented by Formula 1 below:

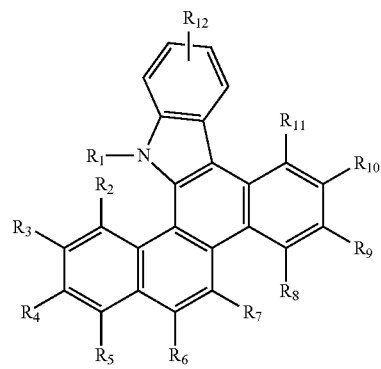

Formula 1 where $R_1$ to $R_{12}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group, a halogen atom, a cyano group, a nitro group, a hydroxyl group, or a carboxyl group, wherein $R_6$ and $R_7$ may be linked to each other to form a group represented by Formula 2 in which ** and * indicates binding sites corresponding to the binding sites of $R_6$ and $R_7$ of Formula 1:

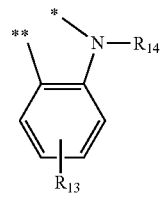

Formula 2 wherein $R_{13}$ to $R_{14}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group, a halogen atom, a cyano group, a nitro group, a hydroxyl group, or a carboxyl group; and two adjacent substituents among $R_1$ to $R_{14}$ may be linked to each other to form a ring.

In some embodiments the heterocyclic compound of Formula 1 may be used as a light-emitting material, an electron-transporting material or an electron-injecting material. The heterocyclic compound of Formula 1, having a heterocyclic group in the molecules thereof, has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments.

An organic light-emitting device manufactured using the heterocyclic compound of Formula 1 has high durability when stored or operated. In addition, due to the inclusion of a substituent such as an aryl group or heterocyclic group, molecular layers formed as thin films may be maintained in good condition, thereby improving the characteristics of the organic light-emitting device.

When $R_6$ and $R_7$ in Formula 1 may be linked to each other to form the group represented by Formula 2, the heterocyclic compound represented by Formula 1 is a compound represented by Formula 1a:

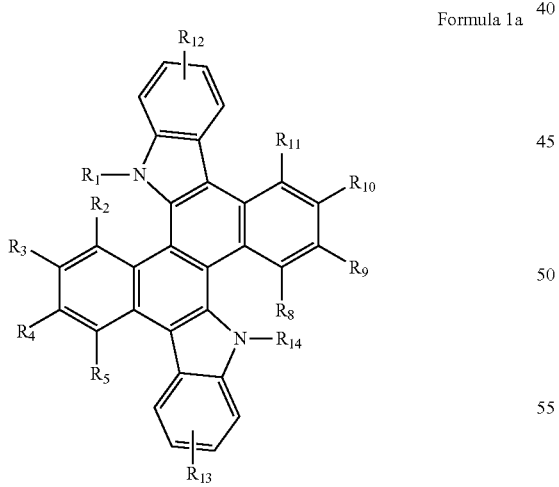

Formula 1a wherein $R_1$-$R_{14}$ in Formula 1a are the same as those described above.

Substituents in Formulae 1 and 2 will now be described in detail.

In some embodiments $R_1$ to $R_{14}$ in Formulae 1 and 2 may be each independently a hydrogen atom, a deuterium atom, a halogen atom, a cyano group, a $C_1$-$C_{20}$ alkyl group, or groups represented by Formulae 2a to 2l below:

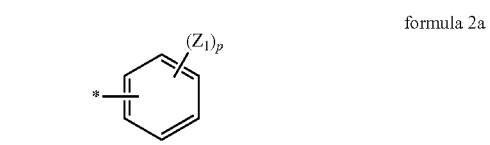

formula 2a

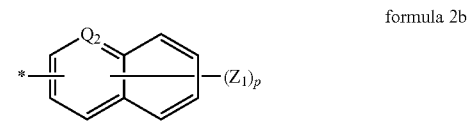

formula 2b

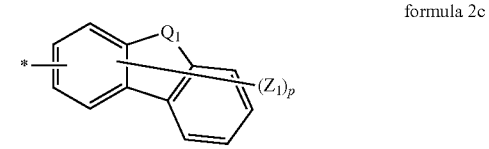

formula 2c

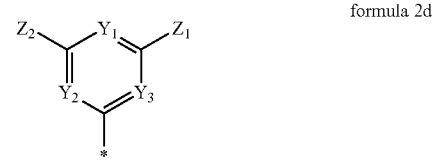

formula 2d

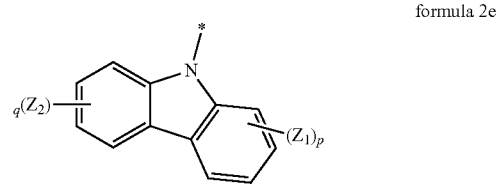

formula 2e

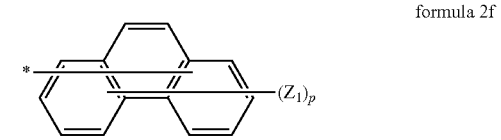

formula 2f

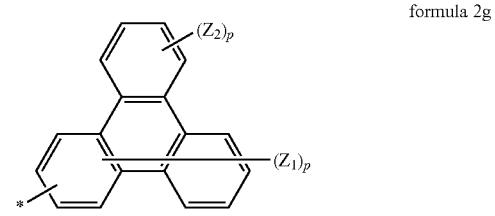

formula 2g formula 2h

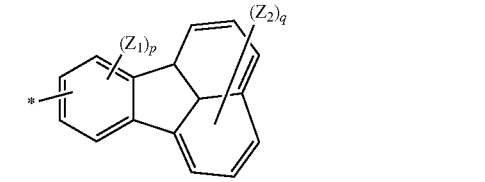

formula 2i

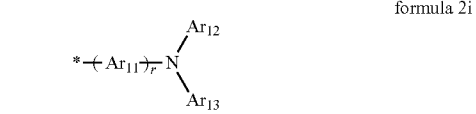

formula 2j

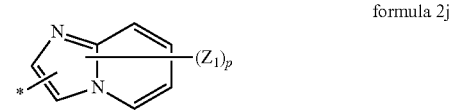

-continued formula 2k
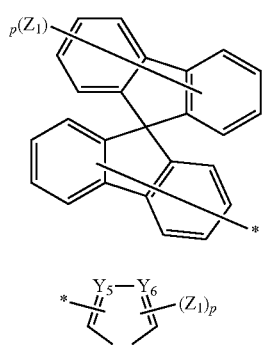

formula 2l
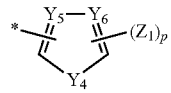

In Formula 2a to 2l above, $Q_1$ and $Q_2$ are each independently a linking group selected from among —$C(R_{15})(R_{16})$—, —$N(R_{15})$—, —S—, and —O—; $Y_1, Y_2, Y_3, Y_4, Y_5$ and $Y_6$ are each independently a linking group selected from among —N=, —$C(R_{17})$=, —S—, and —O—;

$Z_1, Z_2, Ar_{12}, Ar_{13}, R_{15}, R_{16}$, and $R_{17}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_2$-$C_{20}$ heterocyclic group, a halogen atom, a cyano group, a nitro group, a hydroxyl group, or a carboxyl group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_2$-$C_{20}$ divalent heterocyclic group; and p is an integer from 1 to 12; q is an integer from 1 to 12; r is an integer from 0 to 5; and * indicates a binding site.

In some embodiments $R_1$ to $R_{14}$ in Formulae 1 and 2 above may be each independently a hydrogen atom, a deuterium atom, a halogen atom, a cyano group, a methyl group, an ethyl group, a propyl group, a butyl group, a pentyl group, or groups represented by Formulae 3a to 3h below:

formula 3a
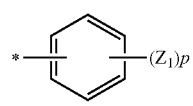

formula 3b
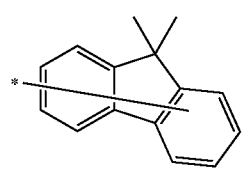

formula 3c
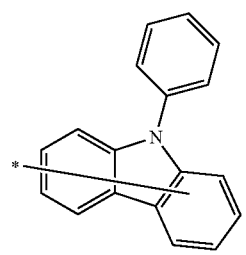

formula 3d
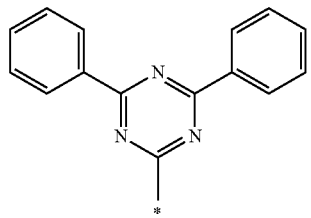

formula 3e
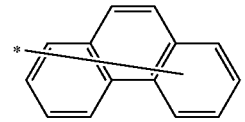

formula 3f
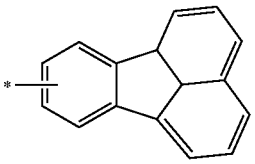

formula 3g
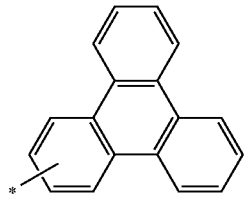

formula 3h
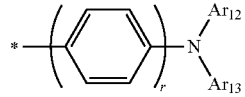

In Formulae 3a to 3h above, $Z_1$, $Ar_{12}$, and $Ar_{13}$ are each independently a hydrogen atom, a deuterium atom, a substituted or unsubstituted aryl group, or a substituted or unsubstituted $C_2$-$C_{20}$ heterocyclic group; and r is an integer from 0 to 2; p is an integer from 1 to 5; and * indicates a binding site.

According to an embodiment of the present embodiment, in Formula 1, $R_2$ to $R_5$ and $R_7$ to $R_{11}$ may be each independently a hydrogen atom or a deuterium atom.

In some embodiments, $R_2$ to $R_5$ and $R_7$ to $R_{11}$ in Formula 1 are each independently a hydrogen atom or a deuterium atom; and $R_1$, $R_6$ and $R_{12}$ are each independently a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group, a halogen atom, a cyano group, a nitro group, a hydroxyl group, or a carboxyl group.

In some embodiments, $R_2$ to $R_5$, and $R_7$ to $R_{11}$ in Formula 1 are each independently a hydrogen atom or a deuterium atom; and $R_1$, $R_6$ and $R_{12}$ are each independently a halogen atom, a cyano group, a substituted or unsubstituted $C_1$-$C_{20}$ alkyl group, or groups represented by Formulae 2a to 2l below.

In some embodiments, $R_2$ to $R_5$, and $R_8$ to $R_{11}$ in Formula 1 are each independently a hydrogen atom or a deuterium atom; and $R_{11}$, $R_{12}$, $R_{13}$, and $R_{14}$ are each independently a halogen atom, a cyano group, a substituted or unsubstituted $C_1$-$C_{20}$ alkyl group, or groups represented by Formulae 2a to 2l below:

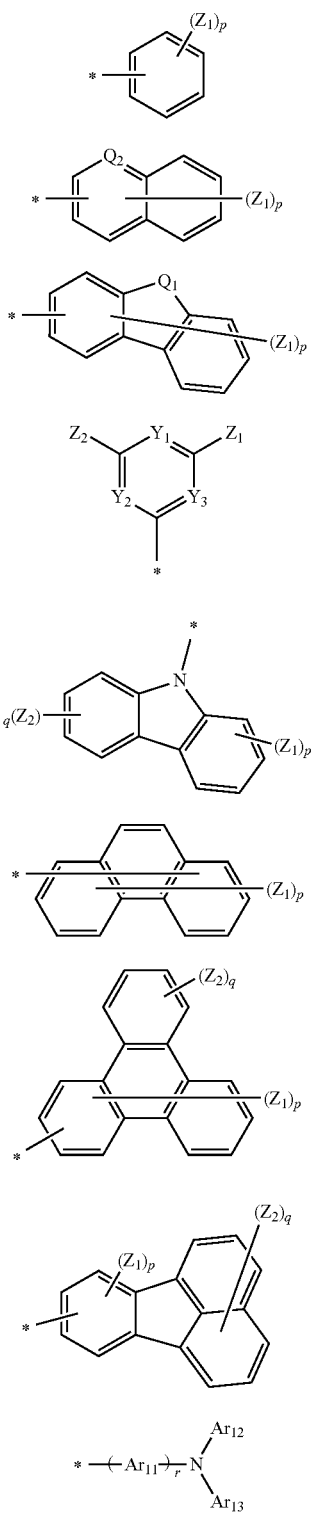

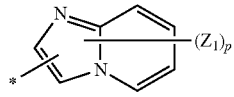

formula 2j

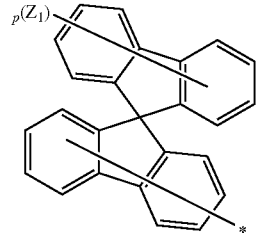

formula 2k

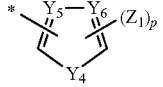

formula 2l

In Formulae 2a to 2l, $Q_1$ and $Q_2$ are each independently a linking group selected from among —C($R_{15}$)($R_{16}$)—, —N($R_{15}$)—, —S—, and —O—;

$Y_1$, $Y_2$, $Y_3$, $Y_4$, $Y_5$, and $Y_6$ are each independently a linking group selected from among —N=, —C($R_{17}$)=, —S—, and —O—;

$Z_1$, $Z_2$, $Ar_{12}$, $Ar_{13}$, $R_{15}$, $R_{16}$, and $R_{17}$ are each independently a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_2$-$C_{20}$ heterocyclic group, a halogen atom, a cyano group, a nitro group, a hydroxyl group, or a carboxyl group;

$Ar_{11}$ is a substituted or unsubstituted $C_1$-$C_{20}$ alkylene group, a substituted or unsubstituted $C_5$-$C_{20}$ arylene group, or a substituted or unsubstituted $C_2$-$C_{20}$ divalent heterocyclic group; and p is an integer from 1 to 12; q is an integer from 1 to 12; r is an integer from 0 to 5; and * indicates a binding site.

In some embodiments, in Formulae 1 and 2 above, $R_1$, $R_2$, $R_3$, $R_4$, $R_5$ and $R_{12}$ may be respectively identical with $R_{14}$, $R_8$, $R_9$, $R_{10}$, $R_{11}$, and $R_{13}$; and $R_1$ to $R_5$ and $R_8$ to $R_{14}$ may be each independently a hydrogen atom, a deuterium atom, a halogen atom, a cyano group, a methyl group, an ethyl group, a propyl group, a butyl group, a pentyl group, or groups represented by Formulae 3a to 3h below:

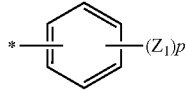

formula 3a

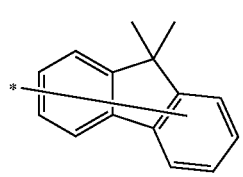

formula 3b

-continued

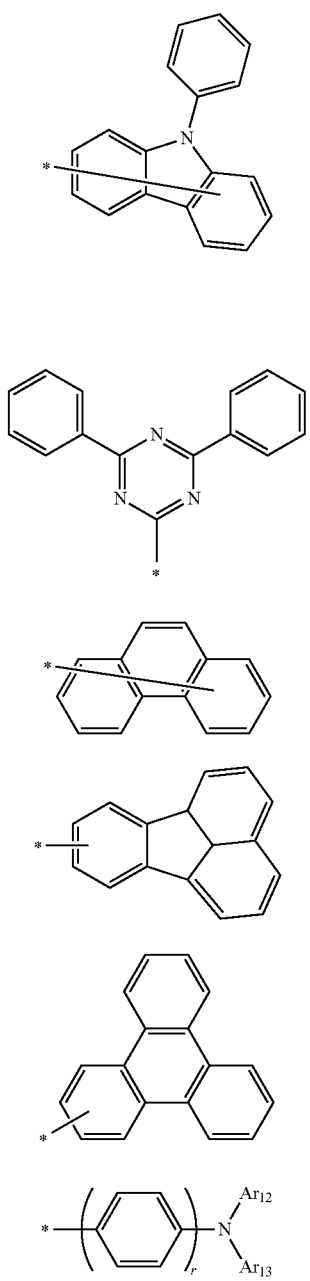

formula 3c formula 3d formula 3e formula 3f formula 3g formula 3h

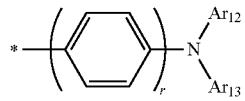

In Formulae 3a to 3h above, $Z_1$, $Ar_{12}$, and $Ar_{13}$ are each independently a hydrogen atom, a deuterium atom, a substituted or unsubstituted aryl group, or a substituted or unsubstituted $C_2$-$C_{20}$ heterocyclic group; and r is an integer from 0 to 2; p is an integer from 1 to 5; and * indicates a binding site.

In some embodiments, in Formulae 1 and 2 above, $R_1$, $R_2$, $R_3$, $R_4$, $R_5$, and $R_{12}$ may be respectively identical with $R_{14}$, $R_8$, $R_9$, $R_{10}$, $R_{11}$, and $R_{13}$; $R_2$ to $R_5$ and $R_8$ to $R_{11}$ are each respectively a hydrogen atom or a deuterium atom; and $R_{11}$, $R_{12}$, $R_{13}$ and $R_{14}$ are each independently a hydrogen atom, a deuterium atom, a halogen atom, a cyano group, a methyl group, an ethyl group, a propyl group, a butyl group, a pentyl group, or groups represented by Formulae 3a to 3h below:

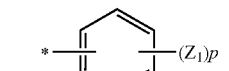

formula 3a

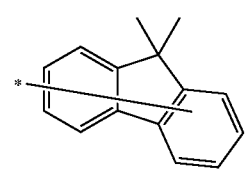

formula 3b

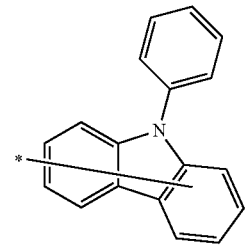

formula 3c

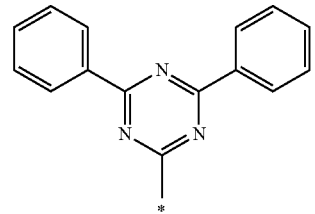

formula 3d

formula 3e

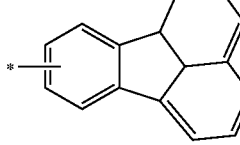

formula 3f

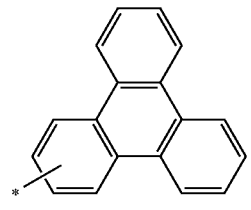

formula 3g

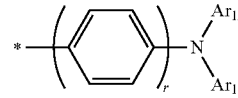

formula 3h

In Formulae 3a to 3h above, $Z_1$, $Ar_{12}$, and $Ar_{13}$ are each independently a hydrogen atom, a deuterium atom, a substituted or unsubstituted aryl group, or a substituted or unsubstituted $C_2$-$C_{20}$ heterocyclic group; and r is an integer from 0 to 2; p is an integer from 1 to 5; and * indicates a binding site.

Examples of the heterocyclic compound of Formula 1 include, but are not limited to, Compounds I to 125 represented below. However, the heterocyclic compounds represented by Formula 1 are not limited thereto.

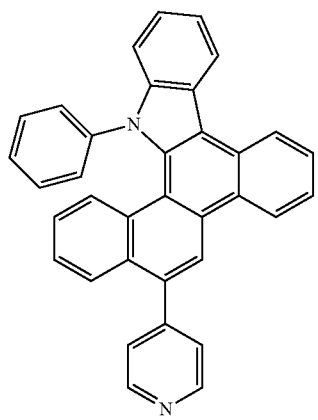
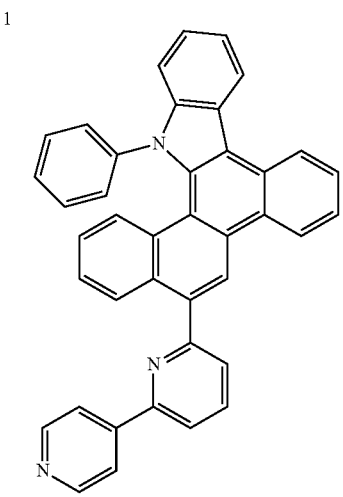
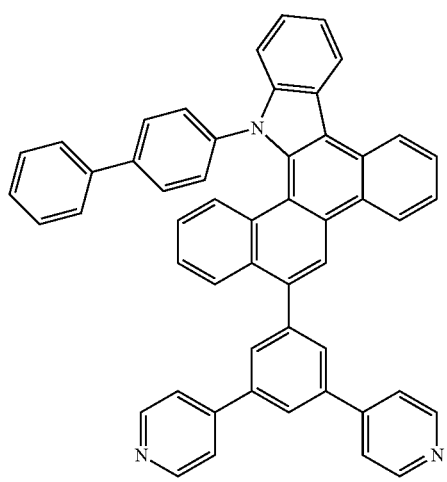
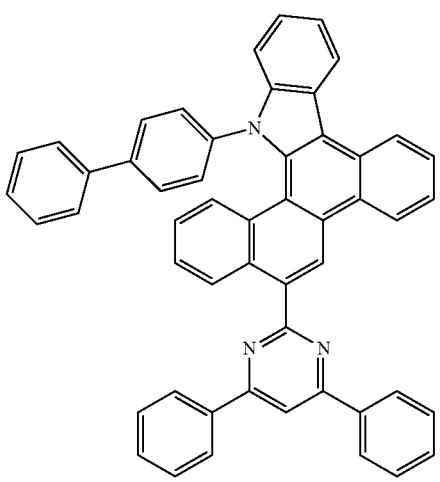
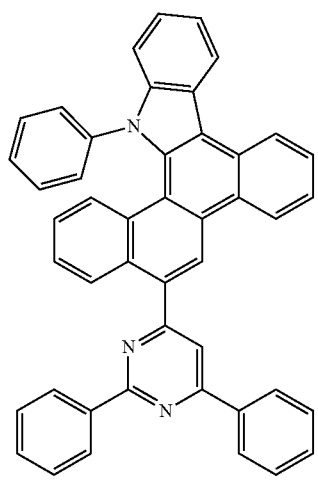
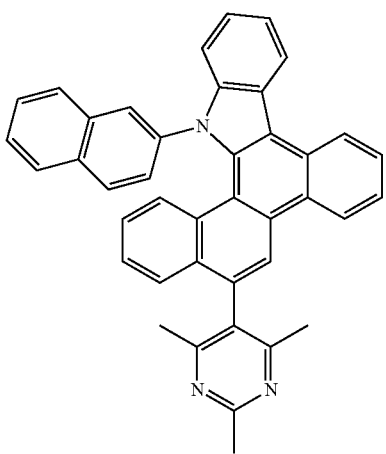

-continued
7
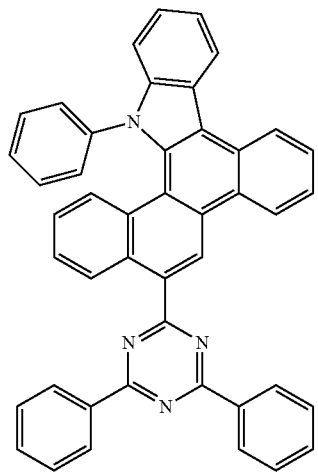
8
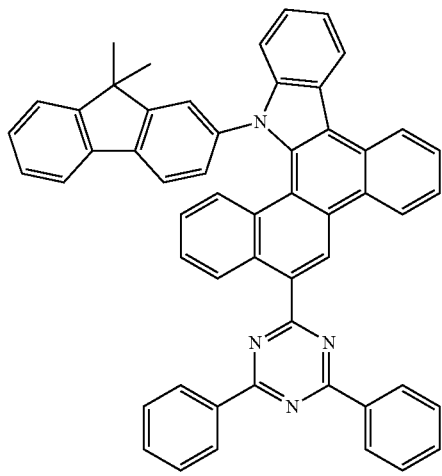
9
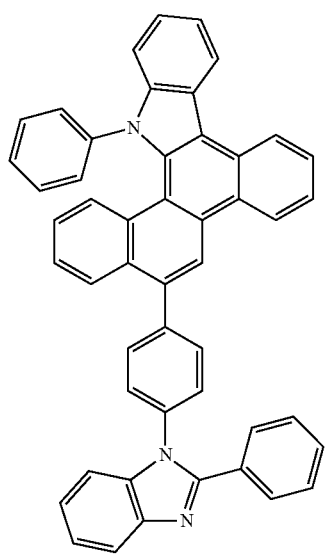
10
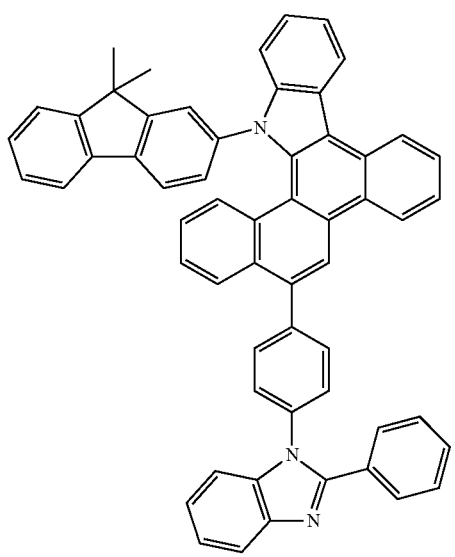
11
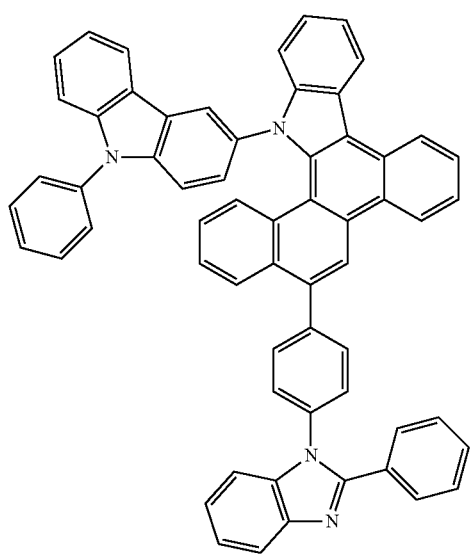
12
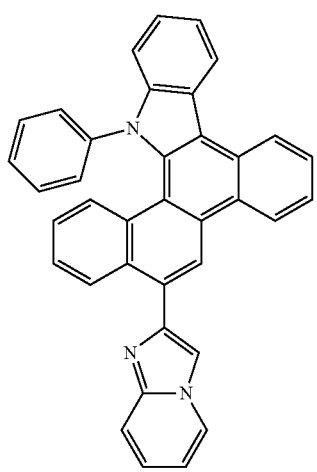

-continued
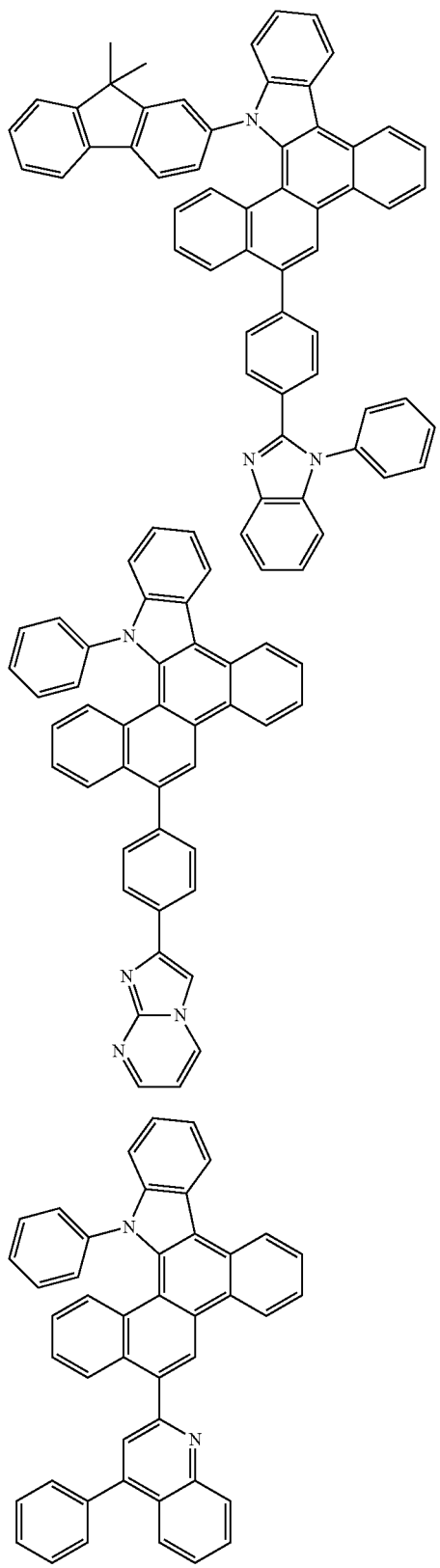
13
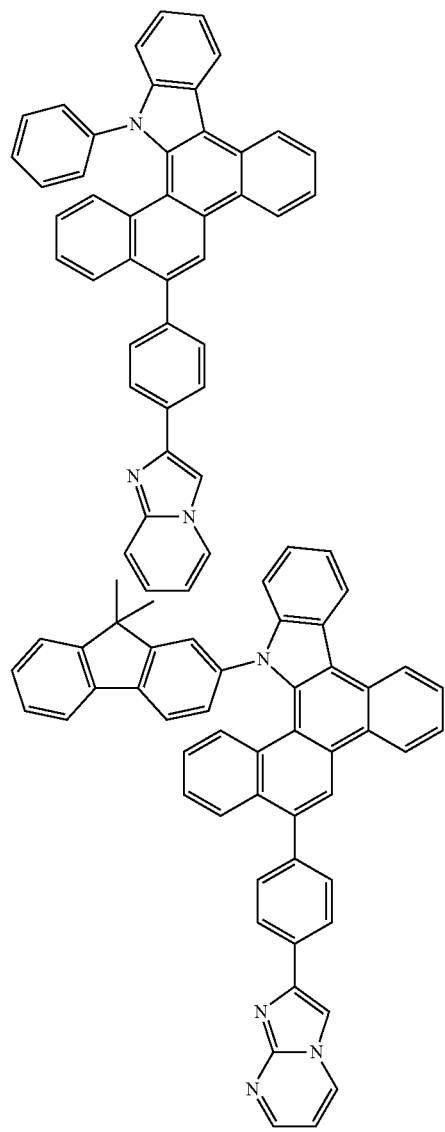
14
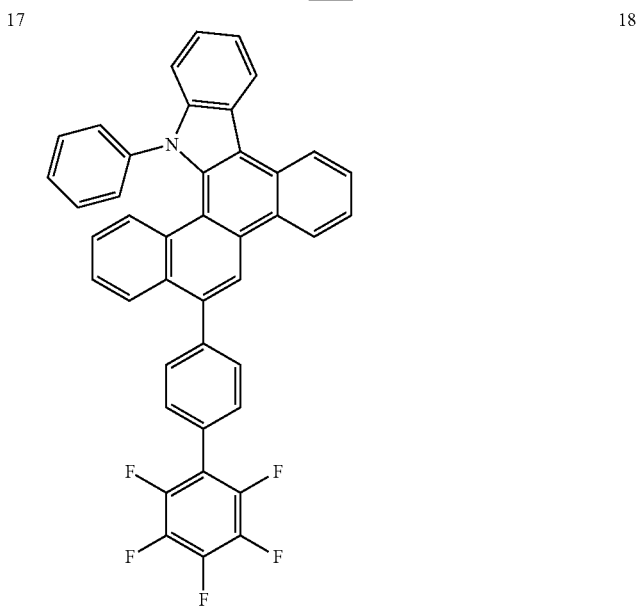
15 16
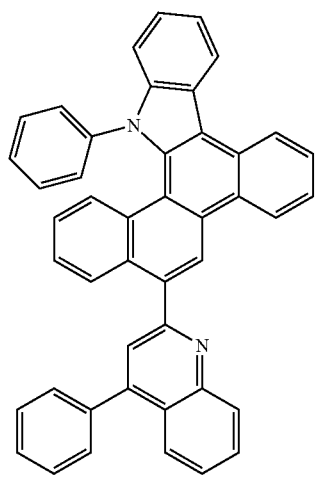
17
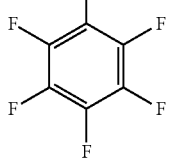
18

19
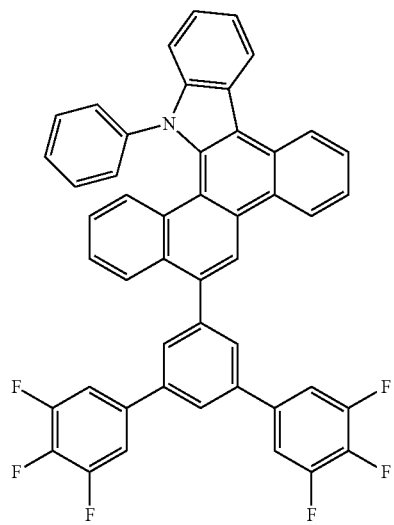
20
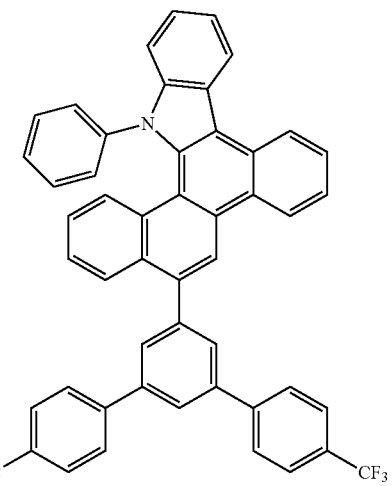
21
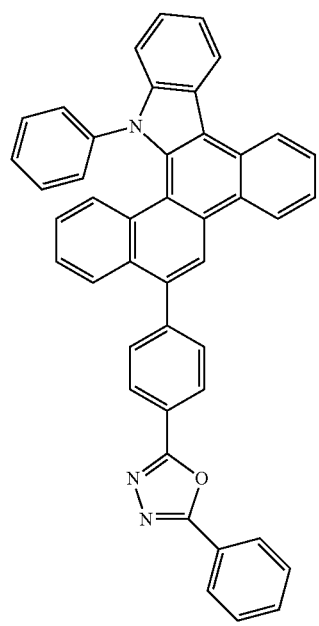
22
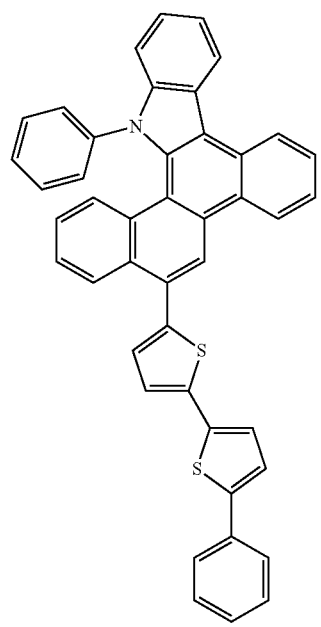
23
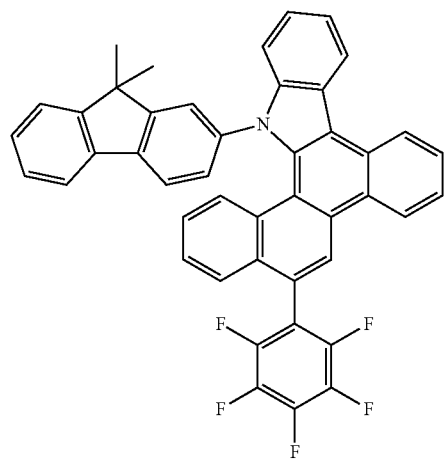
24
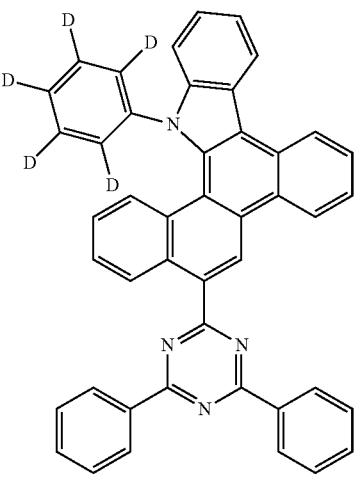

-continued
25
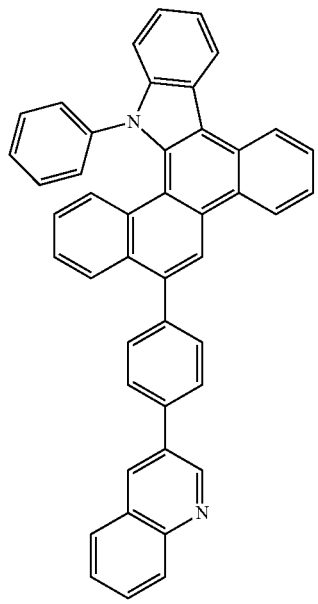
26
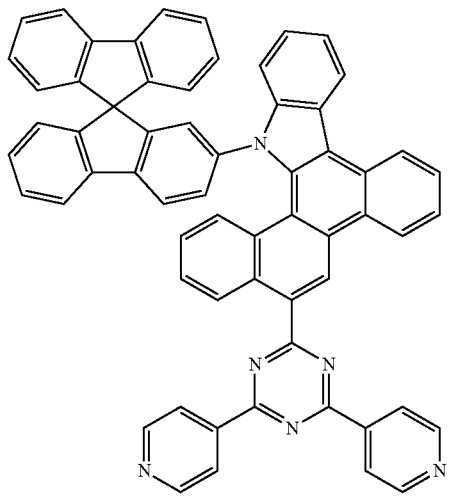
27
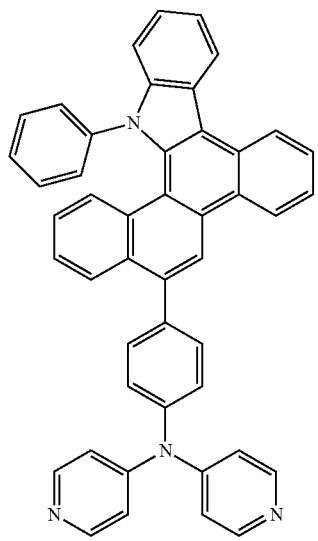
28
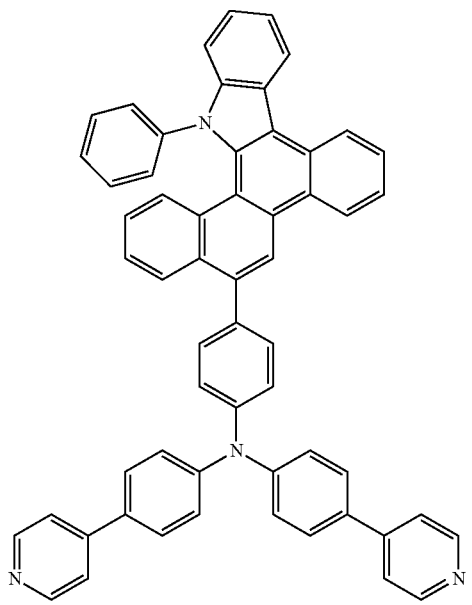

-continued
| 29 | 30 |
|---|---|
| 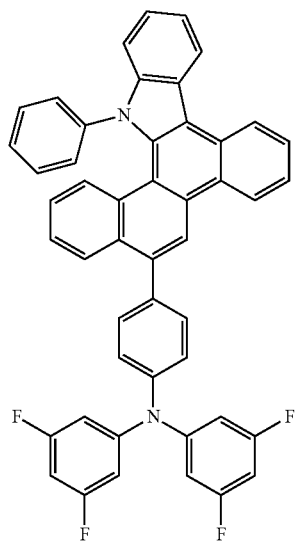 | 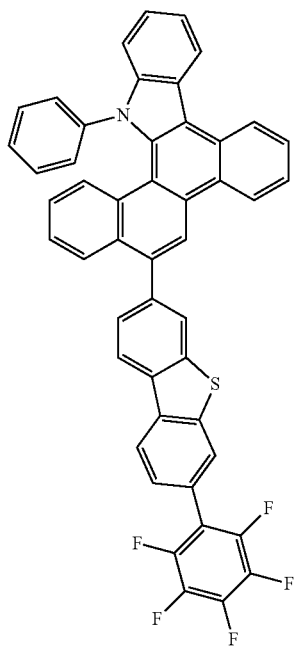 |
| 31 | 32 |
|---|---|
| 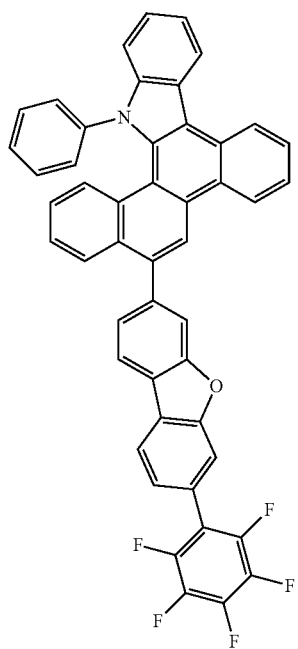 | 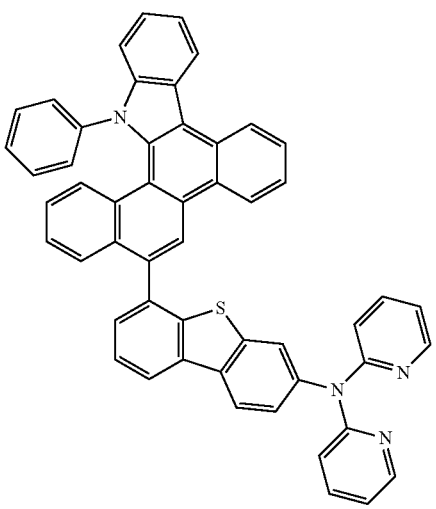 |
| 33 | 34 |
|---|---|
| 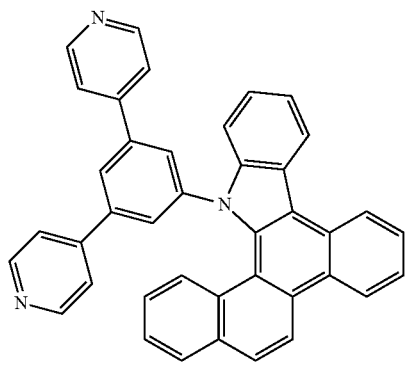 | 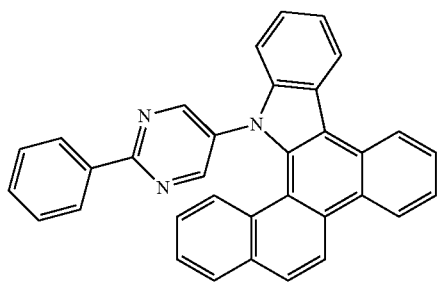 |

-continued
31
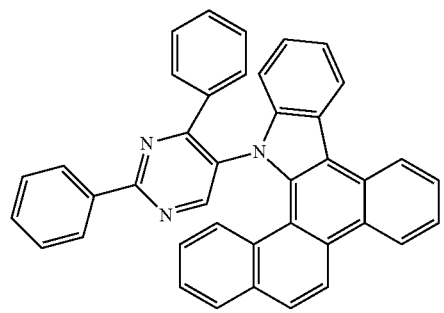
32
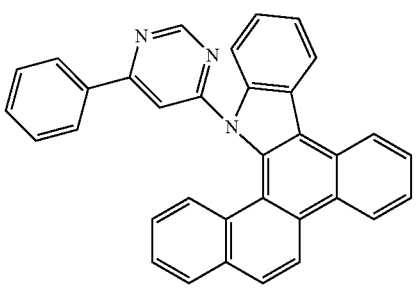
35
37
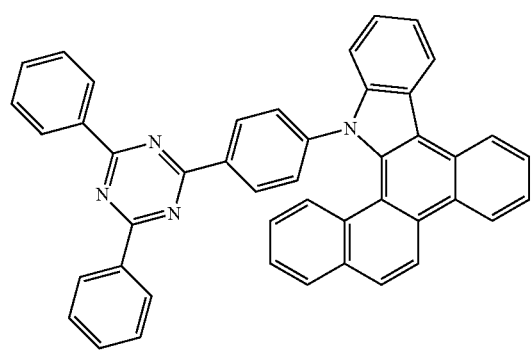
36
38
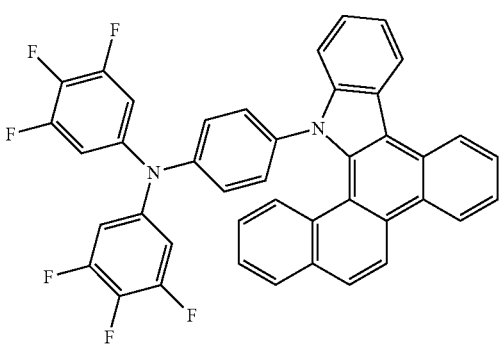
39
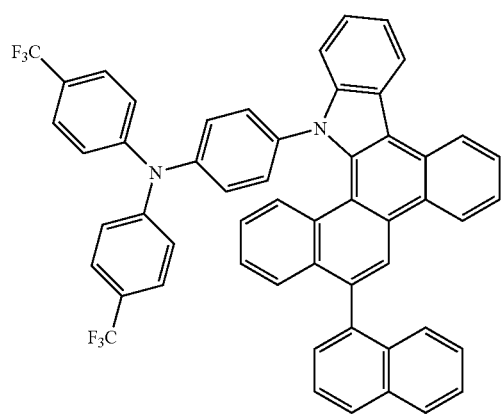
40
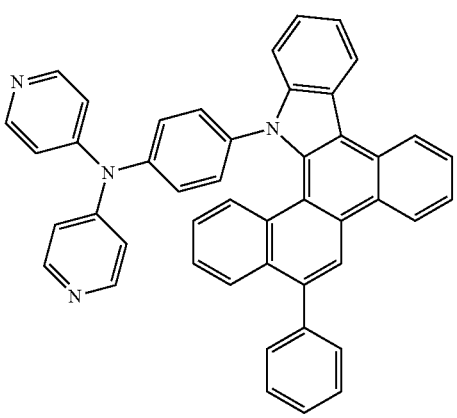
41
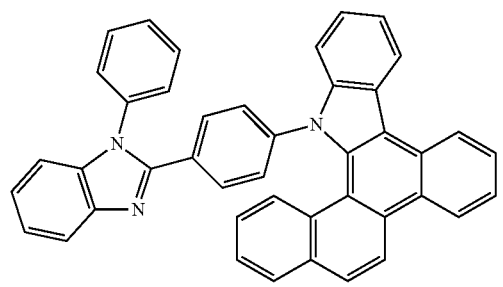
42
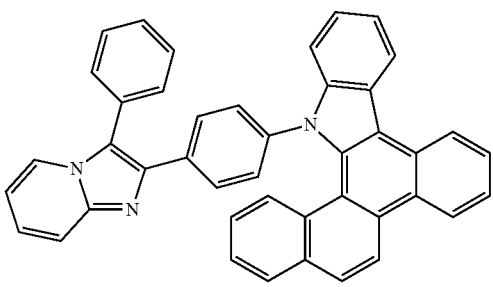

43
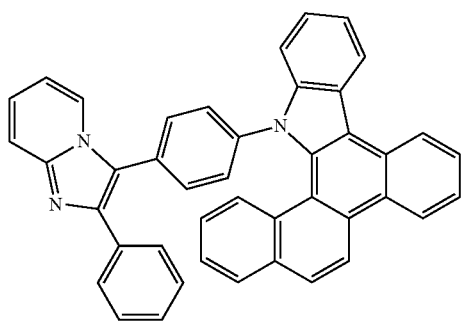
44
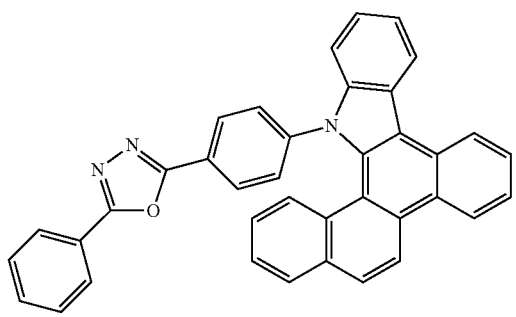
45
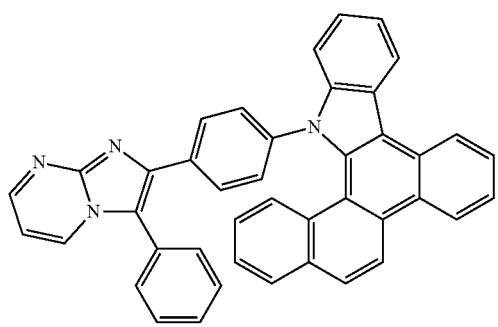
46
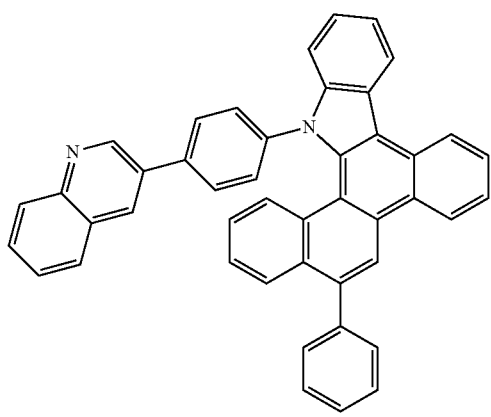
47
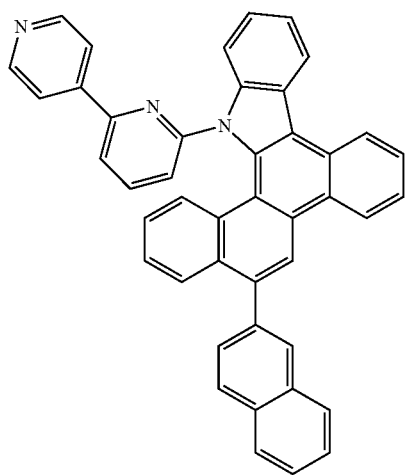
48
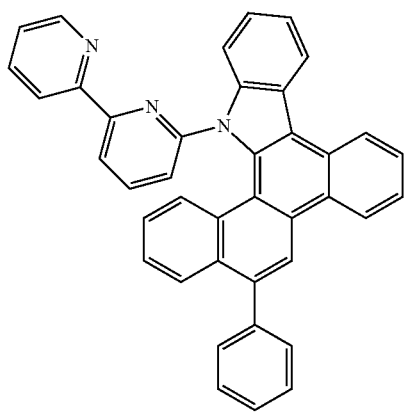

-continued
49
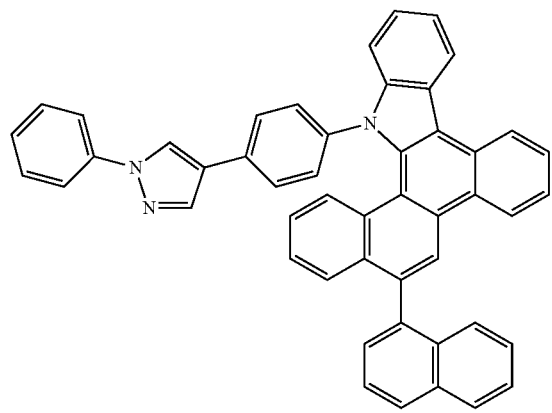
50
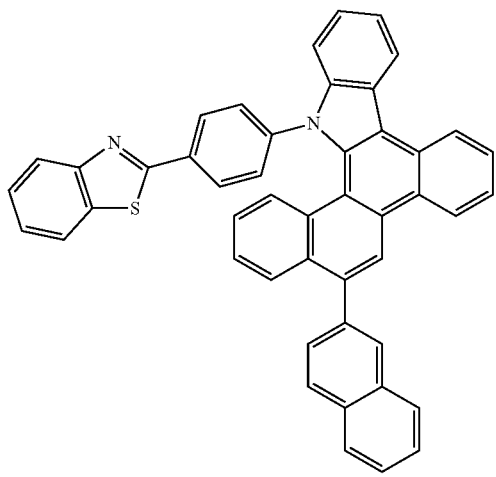
51
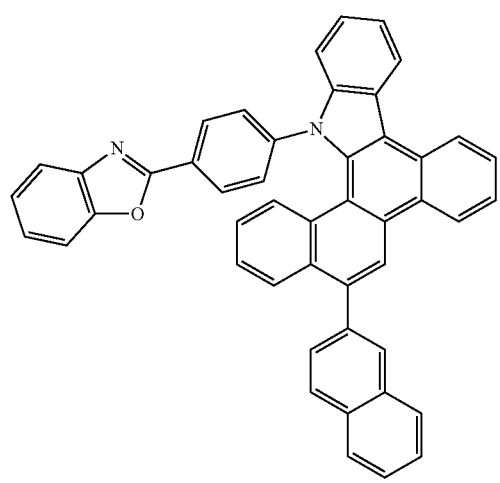
52
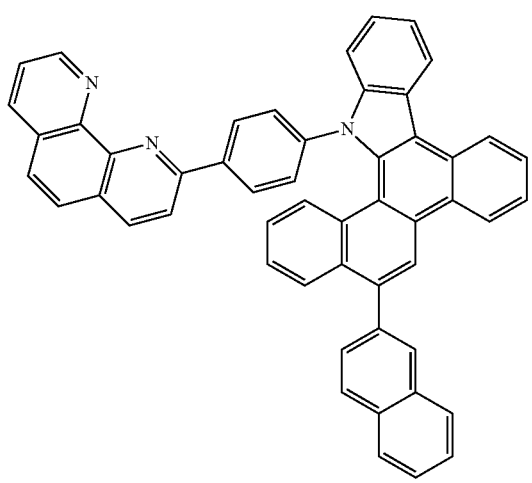
53
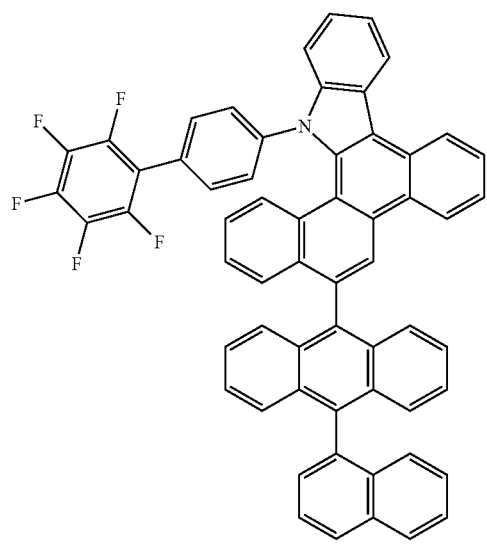
54
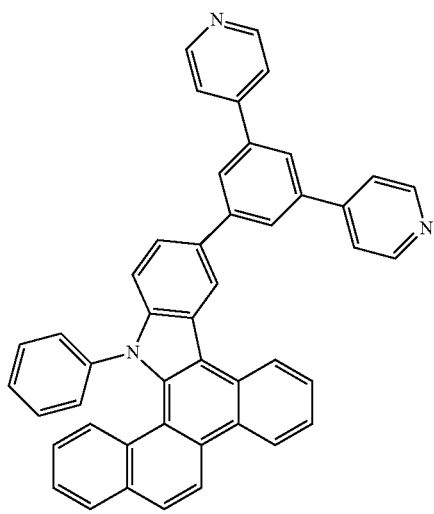

-continued
55
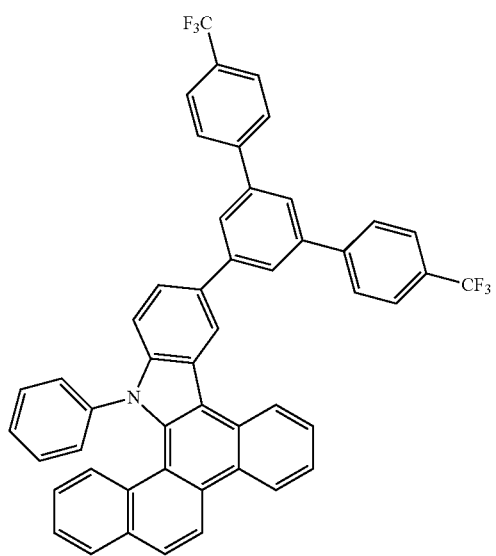
56
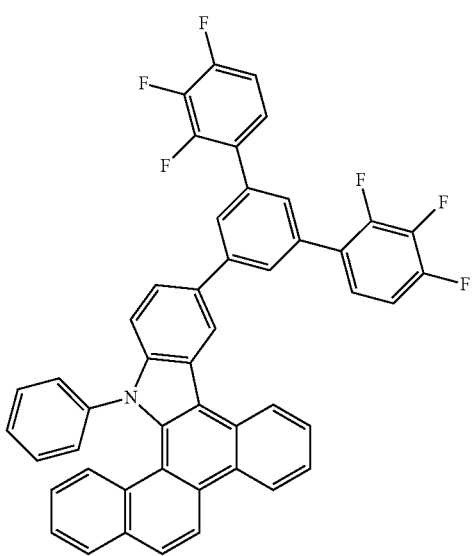
57
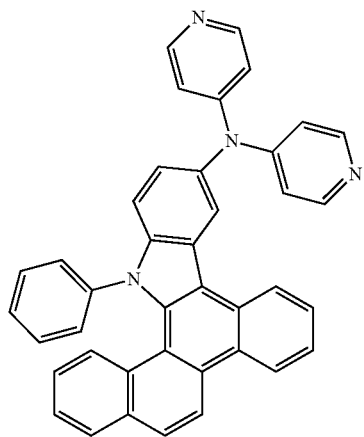
58
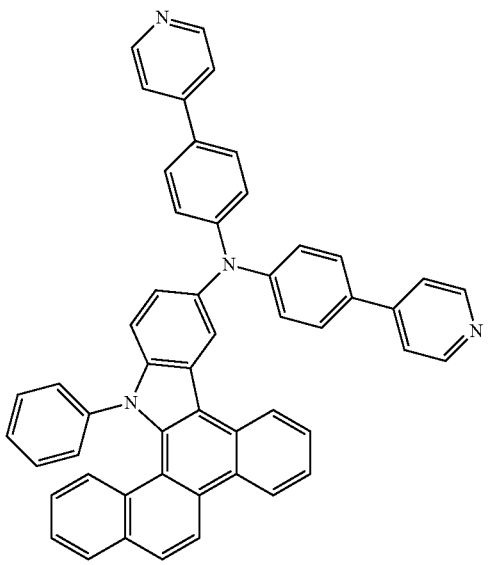
59
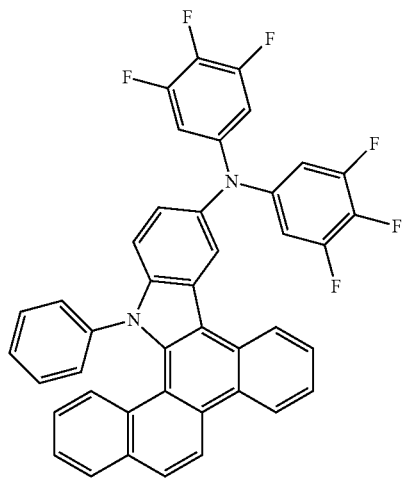
60
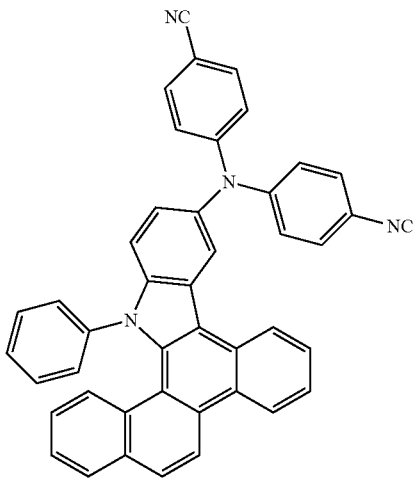

-continued
61
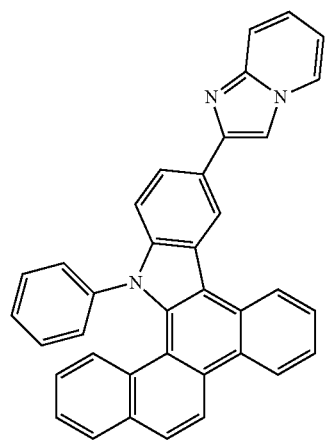
62
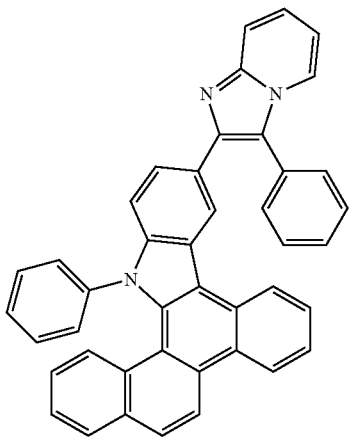
63
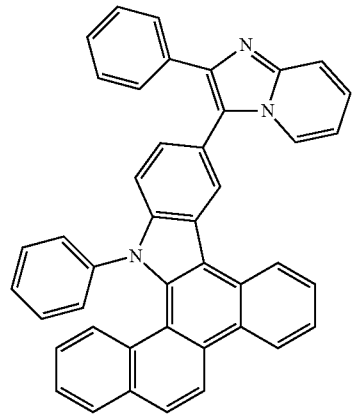
64
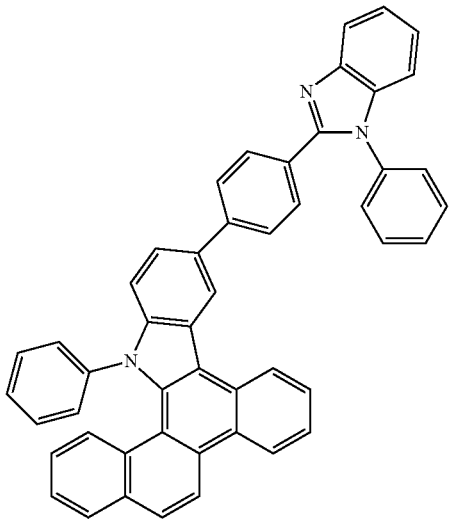
65
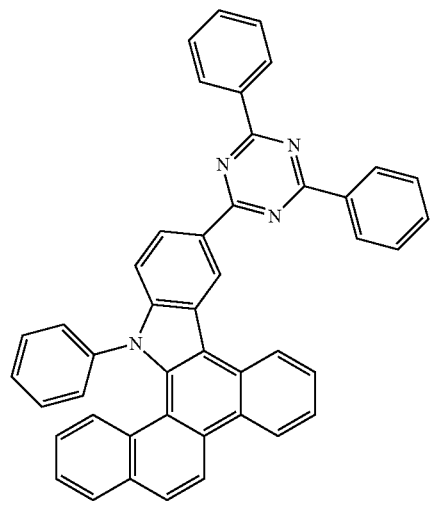
66
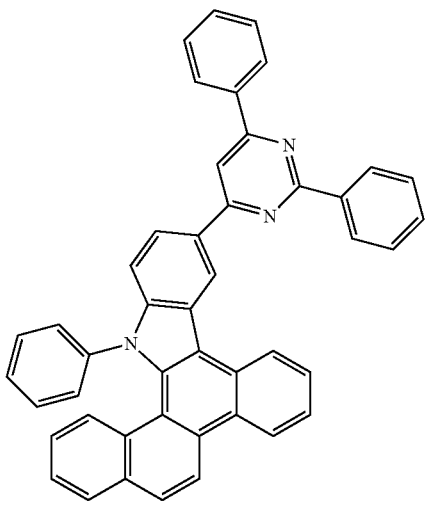

-continued
67
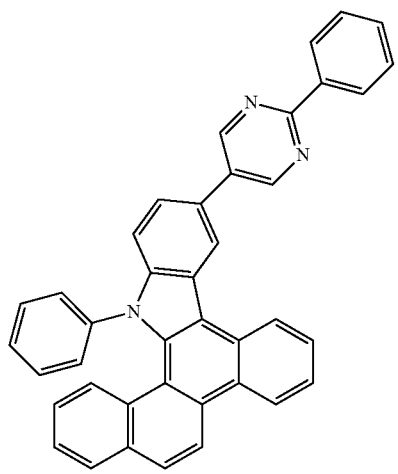
68
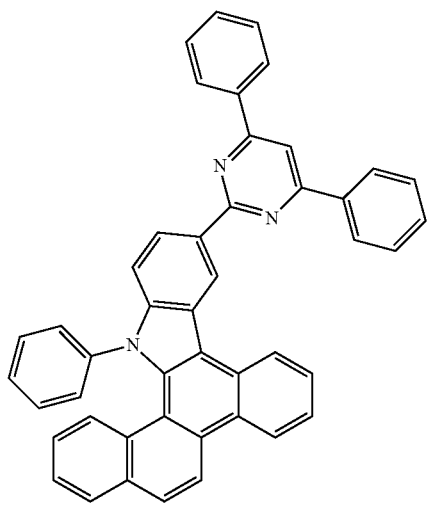
69
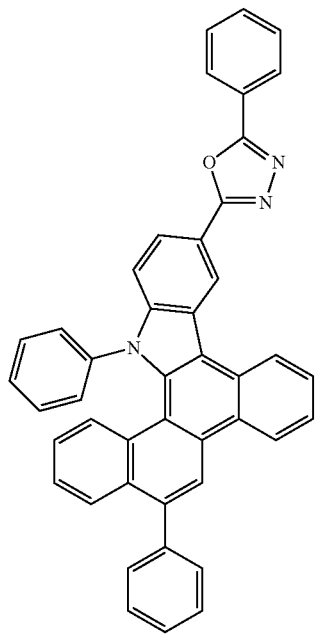
70
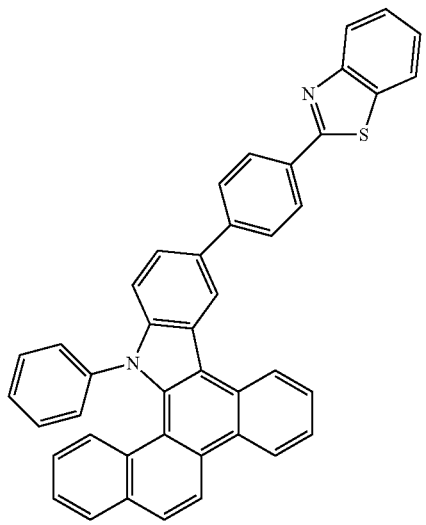
71
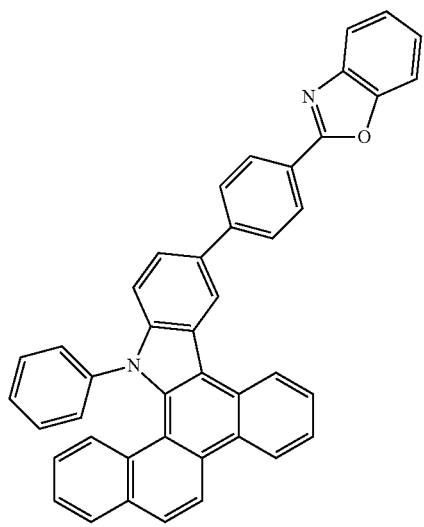
72
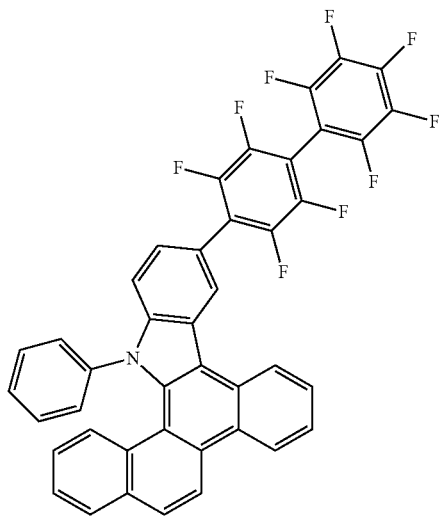

-continued
73
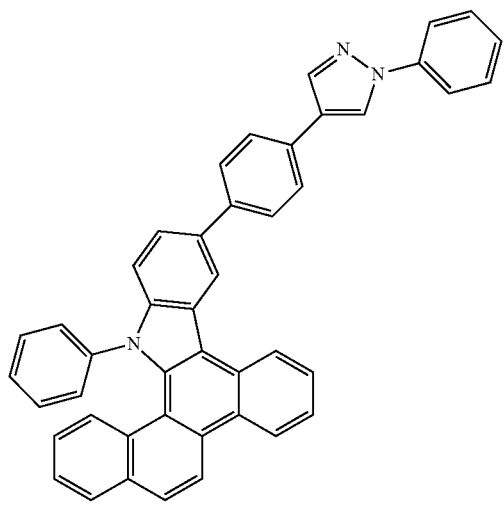
74
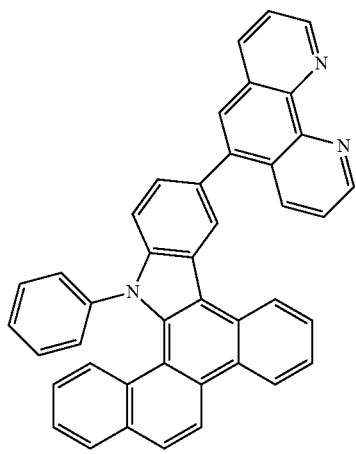
75
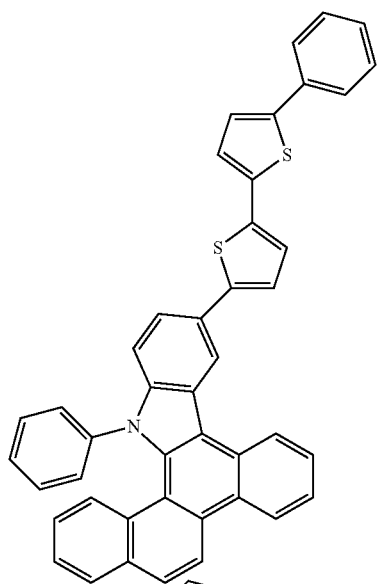
76
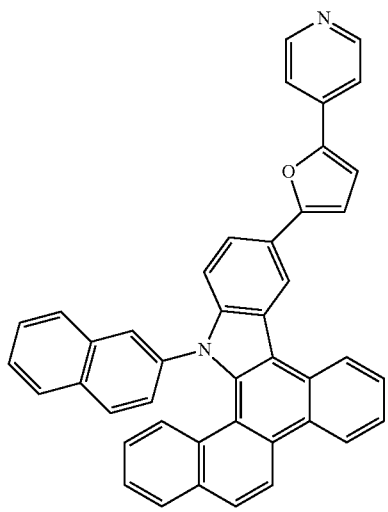
77
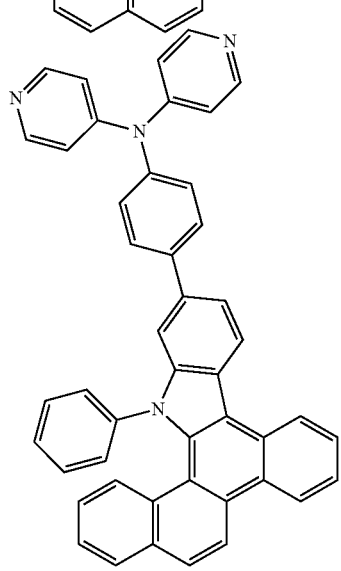
78
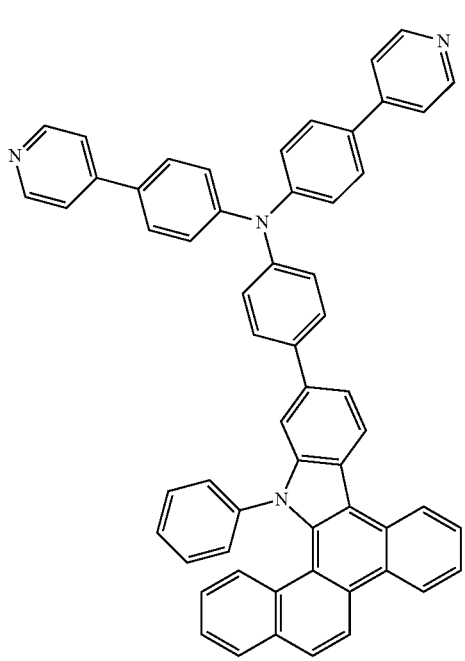

-continued
79
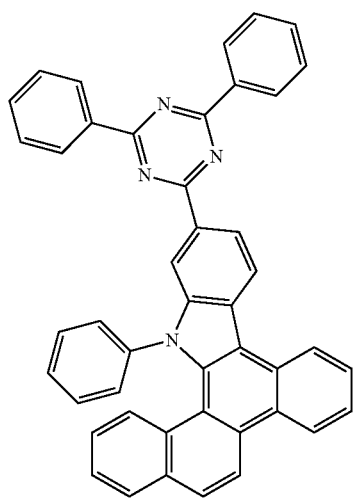
80
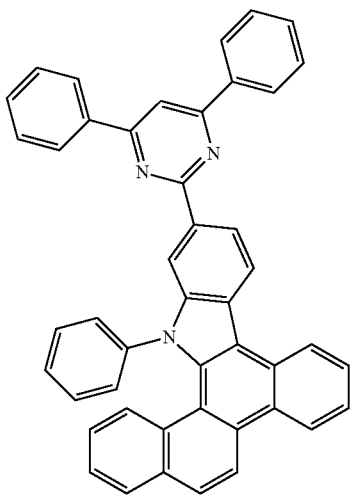
81
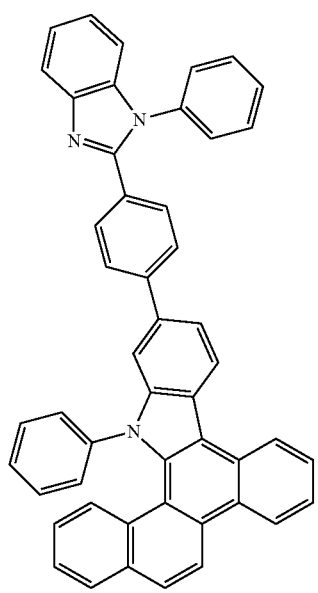
82
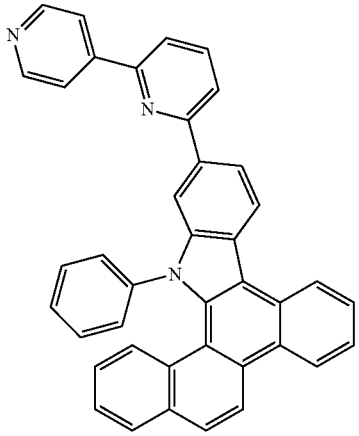
83
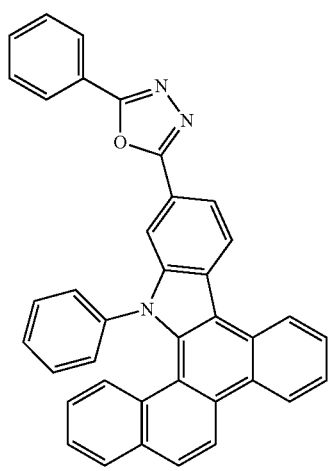
84
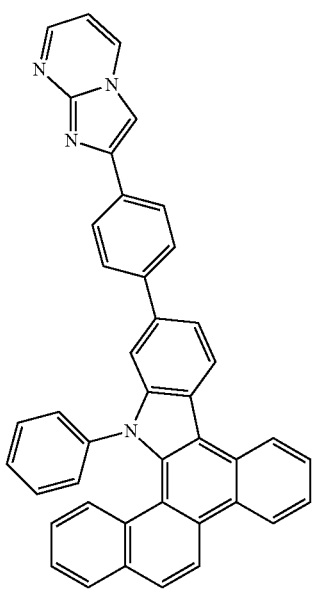

-continued
85
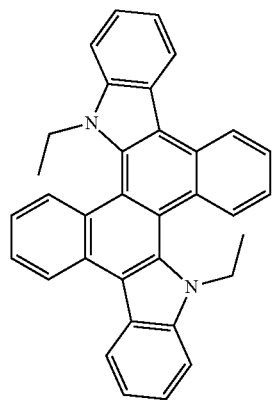
86
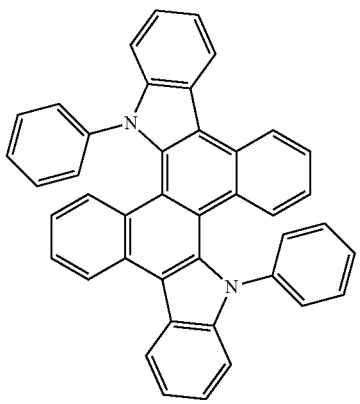
87
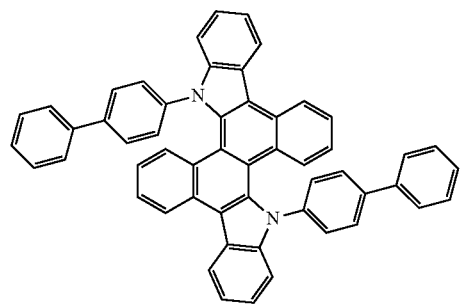
88
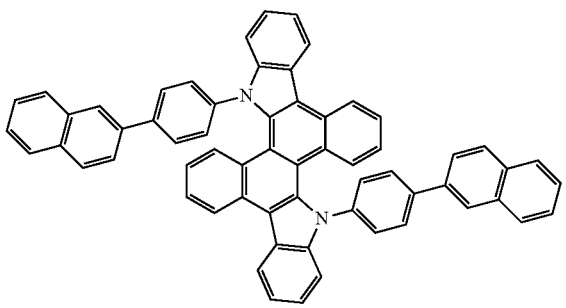
89
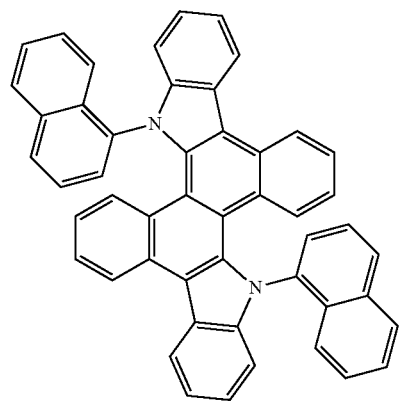
90
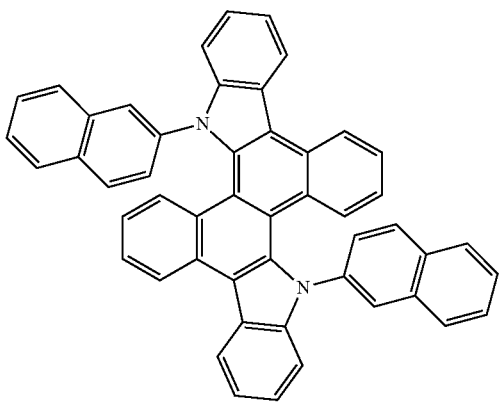
91
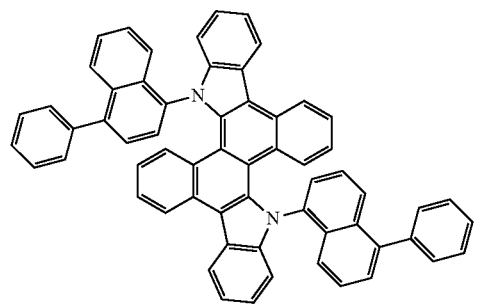
92
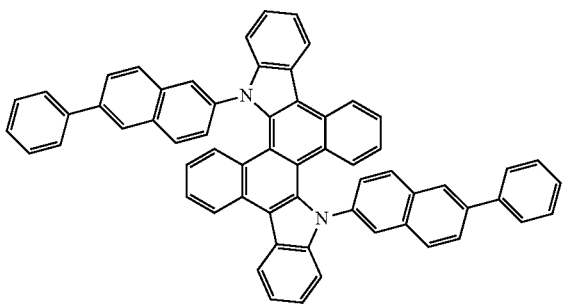

-continued
93
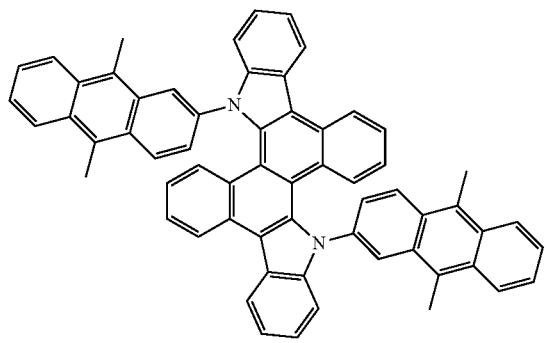
94
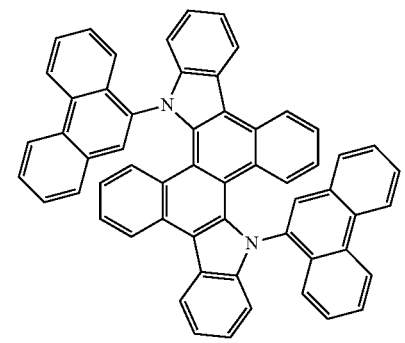
95
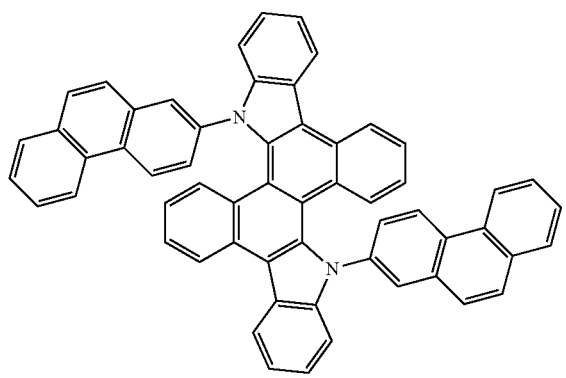
96
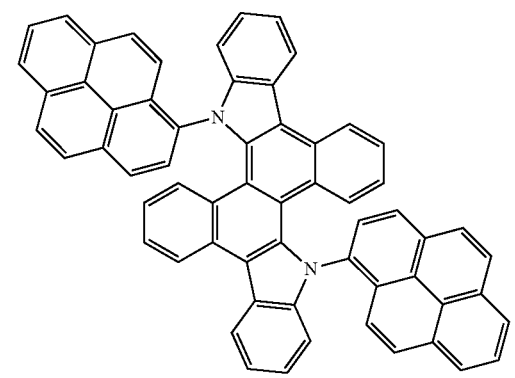
97
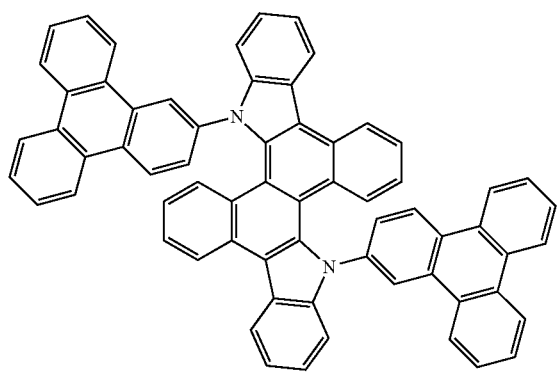
98
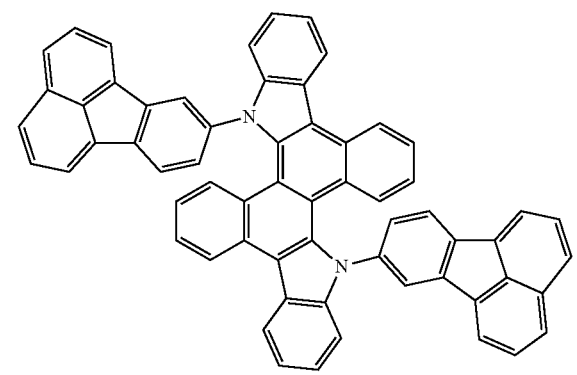
99
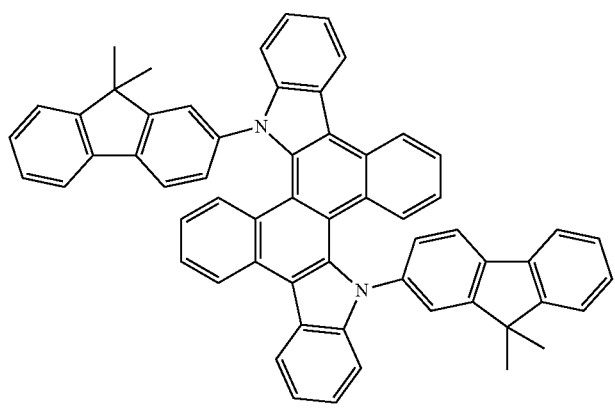

-continued
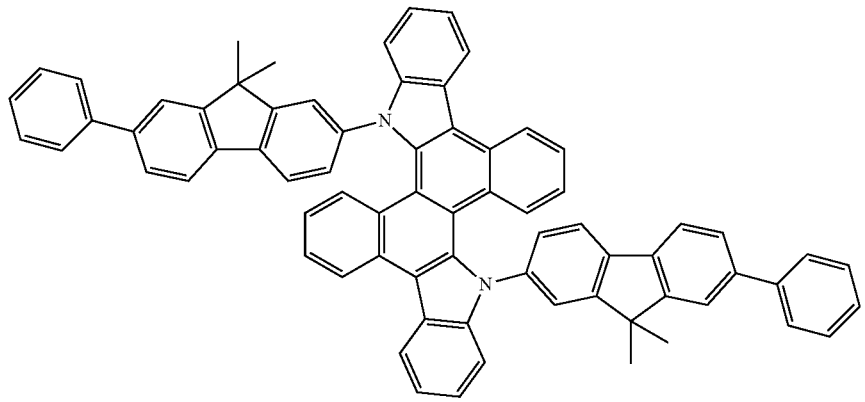
100
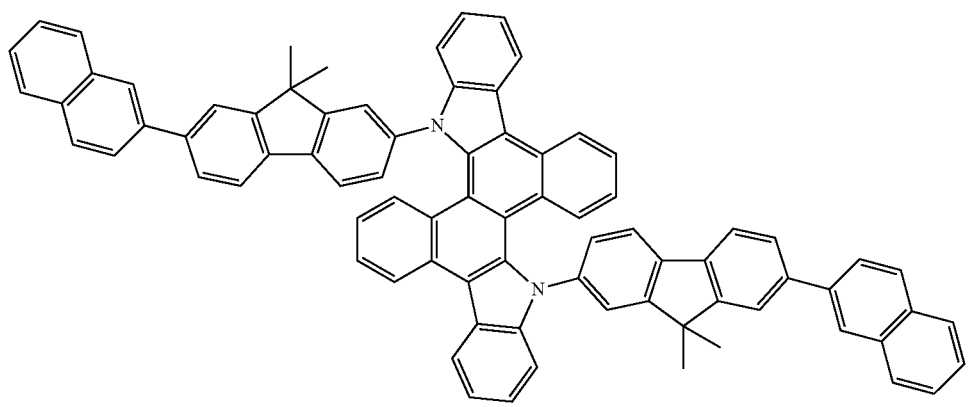
101
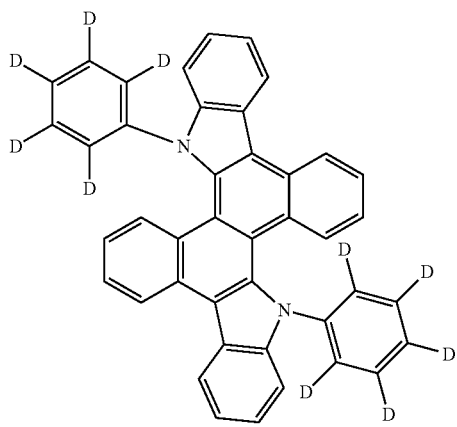
102
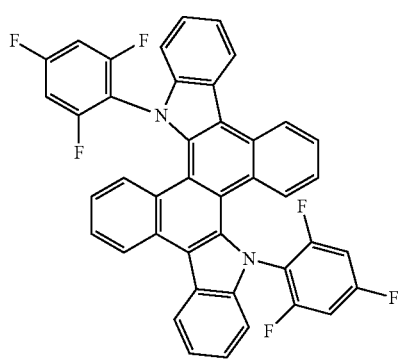
104
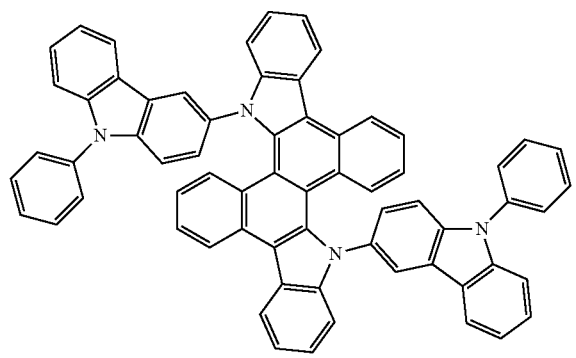
105

-continued
106
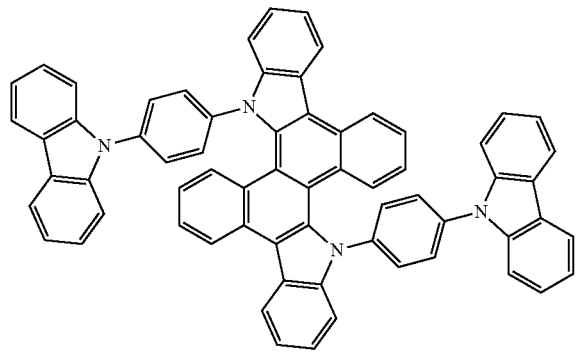
107
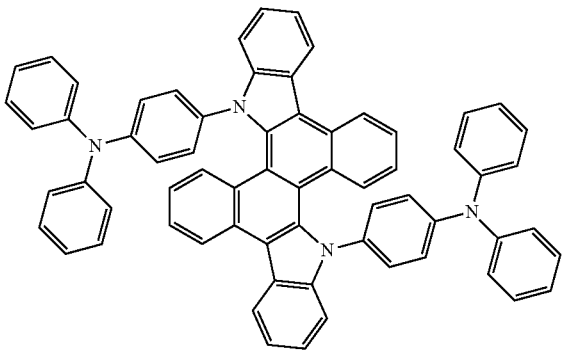
108
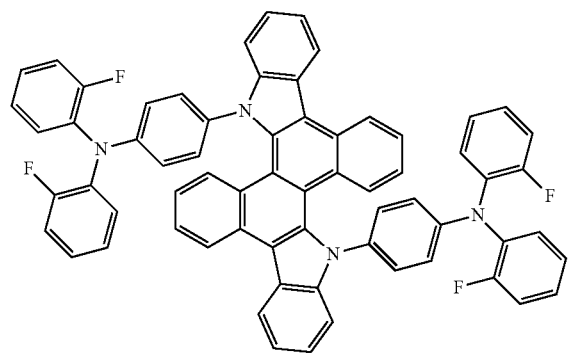
109
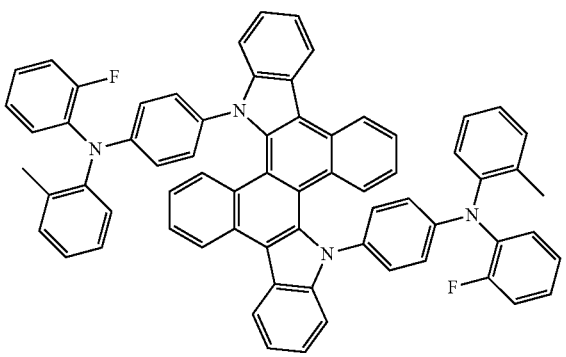
110
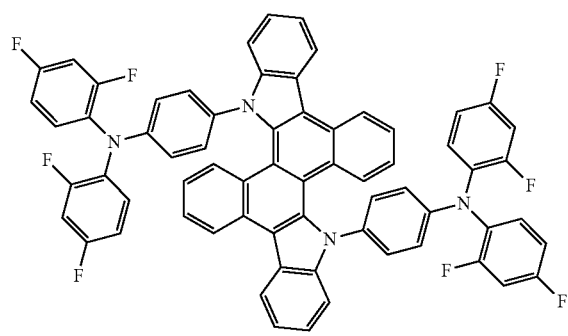
111
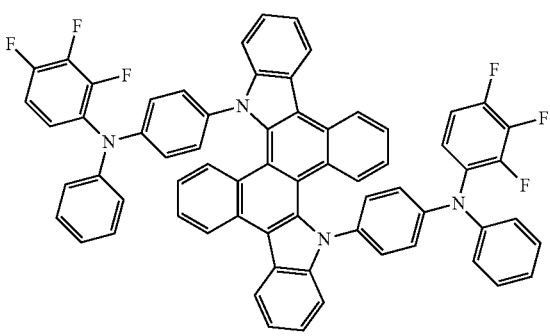
112
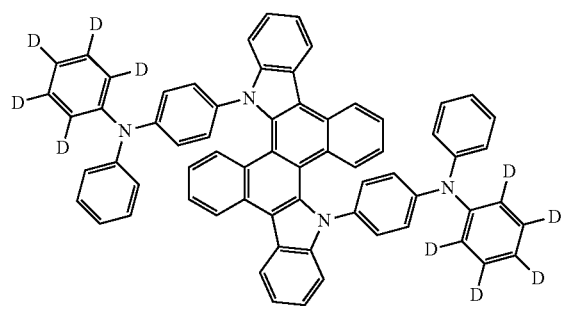
113
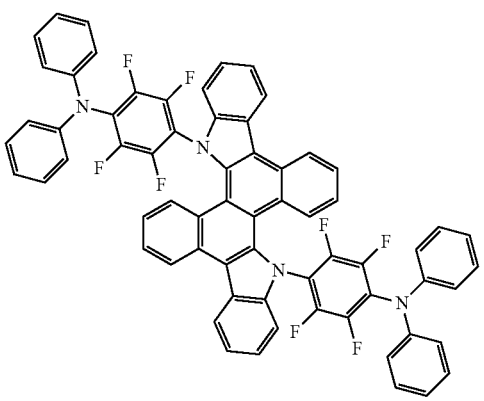

-continued
114
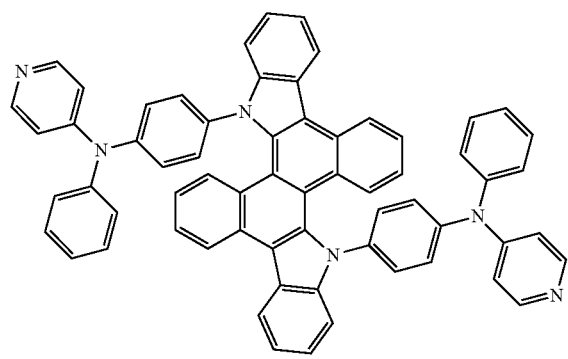
115
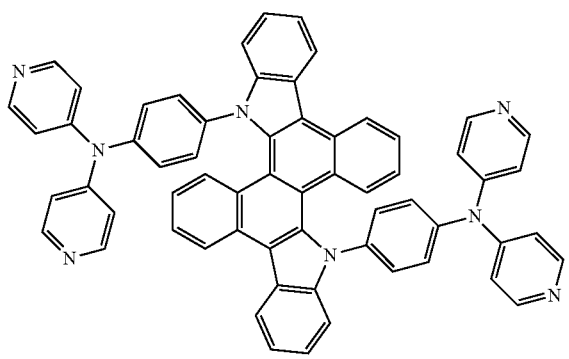
116
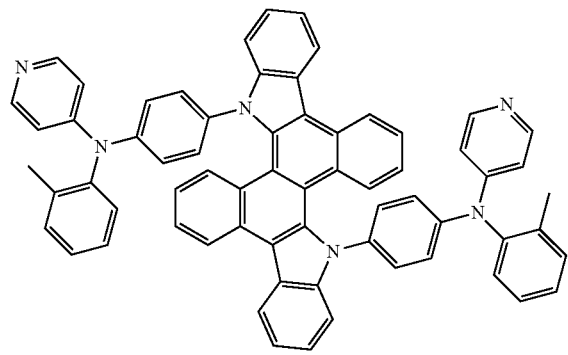
117
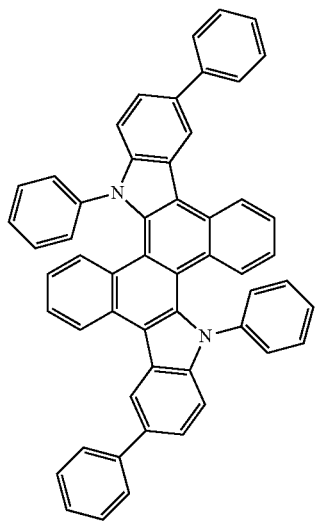
118
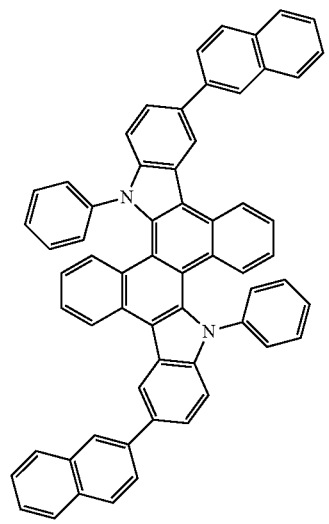
119
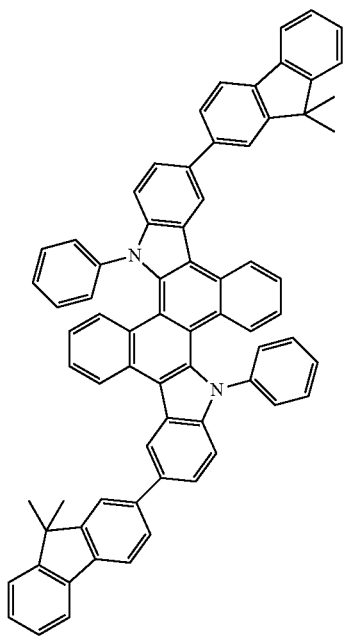

-continued
120
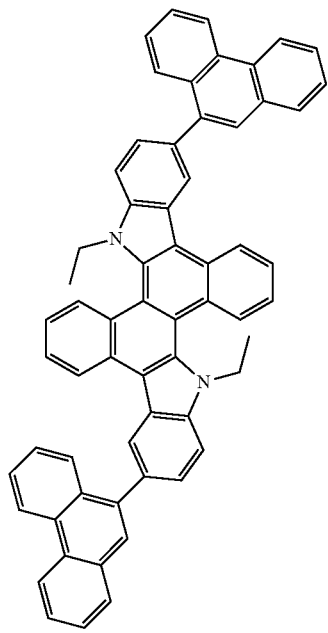
121
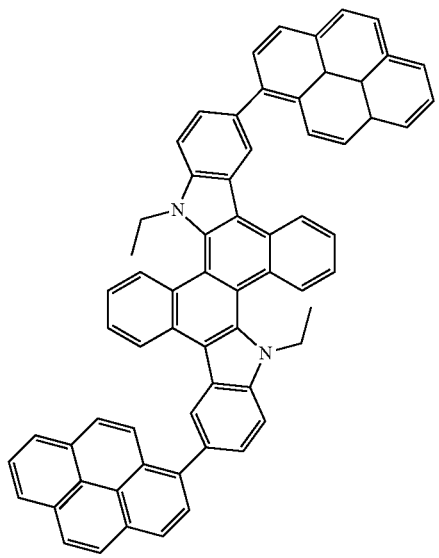
122
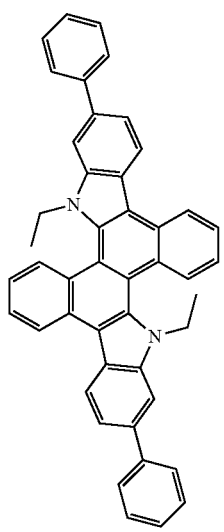
123
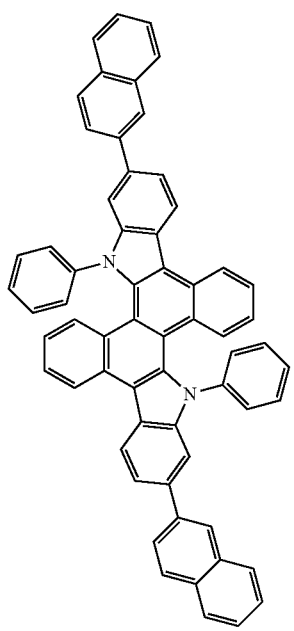

-continued

124

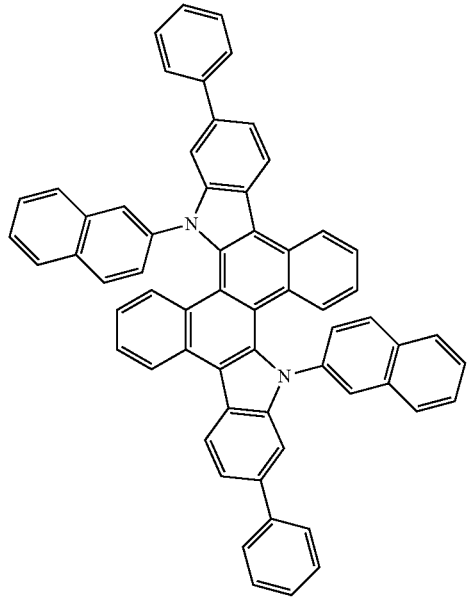

125

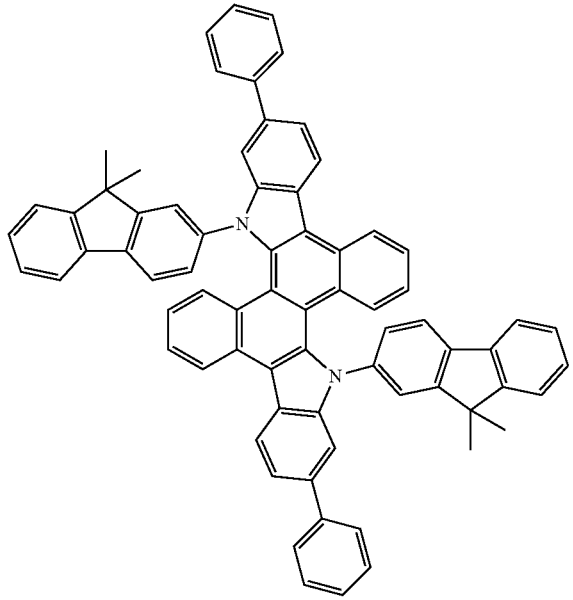

Hereinafter, substituents described with reference to Formulae 1 and 2 will now be described in detail. In this regard, the numbers of carbons in substituents are presented only for illustrative purposes and do not limit the characteristics of the substituents As used herein, the term "substituted A" in the term "substituted or unsubstituted A (wherein A is an arbitrary substituent)" refers to a group A whose at least one hydrogen atom is substituted with a deuterium atom, a halogen atom, a hydroxy group, a cyano group, an amidino group, a hydrazinyl group, a carboxylic acid group or a salt derivative thereof, a sulfonic acid group or a salt derivative thereof, a phosphoric acid group or a salt derivative thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_2$-$C_{60}$ heterocyclic group, —N($Q_{101}$)($Q_{102}$), or —Si($Q_{103}$)($Q_{104}$)($Q_{105}$).

In particular, $Q_{101}$ to $Q_{105}$ may be each independently a hydrogen atom, a halogen atom, a hydroxy group, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, or a substituted or unsubstituted $C_2$-$C_{60}$ heterocyclic group. In this regard, the "substituted A" may include at least one substitute, wherein at least two substituents may be the same or different from each other.

In some embodiments, the "substituted A" may refers to a group A in which at least one hydrogen atom is substituted with a deuterium atom, a halogen atom, a hydroxy group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{20}$ aryl group, a substituted or unsubstituted $C_2$-$C_{20}$ heterocyclic group, —N($Q_1$)($Q_2$), or —Si($Q_3$)($Q_4$)($Q_5$), wherein $Q_1$ to $Q_5$ may be each independently a hydrogen atom, a halogen atom, a hydroxy group, a cyano group, a substituted or unsubstituted $C_1$-$C_{10}$ alkyl group, a substituted or unsubstituted $C_1$-$C_{10}$ alkoxy group, a substituted or unsubstituted $C_6$-$C_{20}$ aryl group, or a substituted or unsubstituted $C_2$-$C_{20}$ heterocyclic group.

In some embodiments, the "substituted A" may refer to a group A in which at least one hydrogen atoms is substituted with a deuterium atom, a halogen atom, a hydroxyl group, a cyano group, a methyl group, an ethyl group, a propyl group, a butyl group, a pentyl group, a methoxy group, an ethoxy group, a propoxy group, a pentoxy group, a phenyl group, a naphthyl group, or an anthryl group.

As used herein, the term "unsubstituted $C_1$-$C_{60}$ alkyl group" may have a linear or branched group. Examples of the $C_1$-$C_{60}$ alkyl group include, but are not limited to, methyl, ethyl, propyl, isobutyl, sec-butyl, pentyl, iso-amyl, hexyl, and the like. Substituents of the substituted $C_1$-$C_{60}$ alkyl group are the same as those described above in conjunction with the "substituted A".

As used herein, the unsubstituted $C_2$-$C_{60}$ alkenyl group indicates a hydrocarbon chain having at least one carbon-carbon double bond in the center or at a terminal of the unsubstituted $C_2$-$C_{60}$ alkyl group. Non-limiting examples of the unsubstituted $C_2$-$C_{60}$ alkenyl group include ethenyl, propenyl, butenyl, pentenyl, hexenyl, heptenyl, octenyl, propadienyl, isoprenyl, and allyl. Substituents of the substituted $C_2$-$C_{60}$ alkenyl group are the same as those described above in conjunction with the "substituted A".

As used herein, the unsubstituted $C_2$-$C_{60}$ alkynyl group indicates a hydrocarbon chain having at least one carbon-carbon triple bond in the center or at a terminal of the unsubstituted $C_2$-$C_{60}$ alkyl group. An example of the unsubstituted $C_2$-$C_{60}$ alkynyl group is acetylenyl. Substituents of the substituted $C_2$-$C_{60}$ alkynyl group are the same as those described above in conjunction with the "substituted A".

As used herein, the unsubstituted $C_1$-$C_{60}$ alkoxy group refers to a group having a structure of —OY wherein Y is an unsubstituted $C_1$-$C_{60}$ alkyl group as described above. Examples of the unsubstituted $C_1$-$C_{60}$ alkoxy group include a methoxy group, an ethoxy group, a propoxy group, an isopropyloxy group, a butoxy group, and a pentoxy group. Substituents of the substituted $C_1$-$C_{60}$ alkoxy group are the same as those described above in conjunction with the "substituted A".

As used herein, the unsubstituted $C_3$-$C_{60}$ cycloalkyl group indicates a cyclic saturated hydrocarbon group. Examples of the unsubstituted $C_3$-$C_{60}$ cycloalkyl group include cyclopropyl, cyclobutyl, cyclopentyl, cyclohexyl, and cyclooctyl. Substituents of the substituted $C_1$-$C_{60}$ cycloalkyl group are the same as those described above in conjunction with the "substituted A".

As used herein, the unsubstituted $C_3$-$C_{60}$ cycloalkenyl group indicates a nonaromatic, cyclic unsaturated hydrocarbon group with at least one carbon-carbon double bond. Examples of the unsubstituted $C_3$-$C_{60}$ cycloalkenyl group include cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyl. Substituents of the substituted $C_3$-$C_{60}$ cycloalkenyl group are the same as those described above in conjunction with the "substituted A".

As used herein, the unsubstituted $C_5$-$C_{60}$ aryl group indicates a monovalent group including a $C_6$-$C_{60}$ carbocyclic aromatic system, which may be monocyclic or polycyclic. In a polycyclic group, at least two rings may be fused to each other. Examples of the unsubstituted $C_5$-$C_{60}$ aryl group include phenyl, pentalenyl, indenyl, naphtyl, azulenyl, heptalenyl, indacenyl, acenaphtyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, and hexacenyl. Substituents of the substituted $C_6$-$C_{60}$ aryl group are the same as those described above in conjunction with the "substituted A".

As used herein, the unsubstituted $C_5$-$C_{60}$ aryloxy group refers to a group having a structure of —OY, wherein Y is an unsubstituted $C_5$-$C_{60}$ aryl group as described above. An example of the unsubstituted $C_5$-$C_{60}$ aryloxy group is a phenoxy group. Substituents of the substituted $C_5$-$C_{50}$ aryloxy group are the same as those described above in conjunction with the "substituted A".

As used herein, the unsubstituted $C_5$-$C_{60}$ arylthio group refers to a group having a structure of —SY, wherein Y is an unsubstituted $C_5$-$C_{60}$ aryl group as described above. Examples of the unsubstituted $C_5$-$C_{60}$ arylthio group include a benzenethio group and a naphthylthio group. Substitutes of the substituted $C_5$-$C_{50}$ arylthio group are the same as those described above in conjunction with the "substituted A".

As used herein, the unsubstituted $C_6$-$C_{60}$ arylene group indicates a divalent group including a $C_6$-$C_{60}$ carbocyclic aromatic system, which may be monocyclic or polycyclic. Examples of the unsubstituted $C_6$-$C_{60}$ arylene group may be understood from those of the of the unsubstituted $C_6$-$C_{60}$ aryl group. Substituents of the substituted $C_6$-$C_{60}$ arylene group are the same as those described above in conjunction with the "substituted A".

As used herein, the unsubstituted $C_2$-$C_{60}$ heterocyclic group indicates a monocyclic or polycyclic group including at least one ring member with at least one heteroatom selected from among N, O, P, and . In a polycyclic group, at least two rings may be fused to each other. Examples of the unsubstituted $C_2$-$C_{60}$ heterocyclic group include pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazole, oxadiazolyl, triazinyl, and benzooxazolyl. Substituents of the substituted $C_2$-$C_{60}$ heterocyclic group are the same as those described above in conjunction with the "substituted A".

As used herein, the unsubstituted $C_2$-$C_{20}$ divalent heterocyclic group indicates a divalent monocyclic or polycyclic group including at least one ring with at least one heteroatom selected from among N, O, P, and S. Examples of the unsubstituted $C_2$-$C_{20}$ divalent heterocyclic group may be understood from those of the unsubstituted $C_2$-$C_{60}$ heterocyclic group described above. Substituents of the substituted $C_2$-$C_{20}$ divalent heterocyclic group may be understood from those described above in conjunction with the "substituted A".

The heterocyclic compound of Formula 1 may be synthesized by using organic synthesis. A synthesis method of the heterocyclic compound of Formula 1 may be understood by those of ordinary skill in the art from the examples that will be described below.

The heterocyclic compound of Formula 1 may be used in an organic light-emitting device. According to another aspect of the present invention, an organic light-emitting device includes a first electrode, a second electrode disposed opposite to the first electrode, and an organic layer between the first electrode and the second electrode, wherein the first layer includes the heterocyclic compound of Formula 1 described above.

When the organic layer, including the heterocyclic compound of Formula 1, is an emission layer, the heterocyclic compound of Formula 1 may be used as a host or dopant for a fluorescence or phosphorescence device.

The organic layer may be an electron injection layer or an electron transport layer. The organic layer may be a single layer having both electron injection and electron transport functions.

In some embodiments the organic layer of the organic light-emitting device may include an emission layer, an electron injection layer, or an electron transport layer, wherein the emission layer, the electron injection layer, or the electron transport layer may include the heterocyclic compound of Formula 1 above, and the emission layer may include a known anthracene, arylamine or styryl compound.

In some embodiments the organic layer of the organic light-emitting device may include an emission layer, an electron injection layer, or an electron transport layer, wherein the emission layer, the electron injection layer, or the electron transport layer may include the heterocyclic compound of Formula 1 above, and a red, green, blue or white emission layer in the emission layer may include a known phosphorescent compound.

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure. Alternatively, the organic light-emitting device may have a first electrode/hole transport layer/emission layer/single layer having both electron injection and electron transport capabilities/second electrode structure, a first electrode/hole injection layer/emission layer/single layer having both electron injection and electron transport capabilities/second electrode structure, or a first electrode/hole injection layer/hole transport layer/emission layer/single layer having both electron injection and electron transport capabilities/second electrode structure.

According to some embodiments of the present invention, the organic light-emitting device may be either a top-emission organic light-emitting device or a bottom-emission organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

The substrate may be any substrate that is used in conventional organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode constitutes an anode, a material having a high work function may be used as the first electrode-forming material to facilitate hole injection. The first electrode may be a reflective electrode or a transmission electrode. Suitable first electrode-forming materials include transparent and conductive materials such as ITO, IZO, $SnO_2$, and ZnO. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like. The first electrode may include two different materials. The first electrode may have any of various structures, and in some embodiments, may have a double-layer structure including two different materials.

An organic layer(s) is formed on the first electrode. The term "organic layer" used herein indicates any layer interposed between the first electrode and the second electrode. The organic layer may not be formed of pure organic materials, and may also include a metal complex.

The organic layer may include a first layer including the heterocyclic compound of Formula 1. The organic layer may further include at least one of a HIL, a HTL, an EML, a hole blocking layer (HBL), an ETL and an EIL. The first layer may include an emission layer.

Next, the HIL may be formed on the first electrode by using any of a variety of methods, and in some embodiments, by using vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any hole-injecting material that is known in the art. Non-limiting examples of suitable hole-injecting materials include a phthalocyanine compound such as copperphthalocyanine, 4,4',4"-tris(3-methylphenylphenylamino) triphenylamine (m-MTDATA; see the formula below), TDATA (see the formula below), 2-TNATA (see formula below), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS).

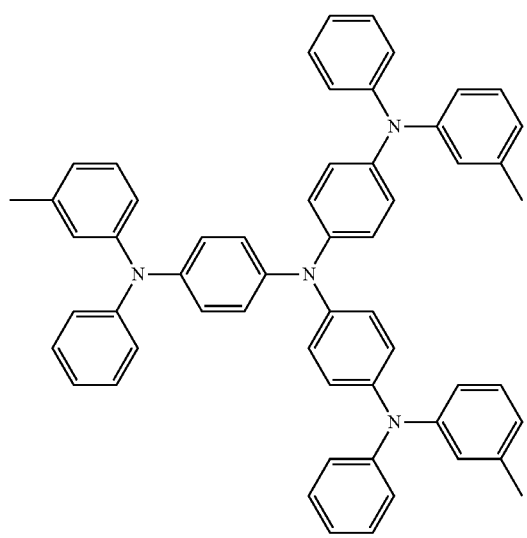

m-MTDATA

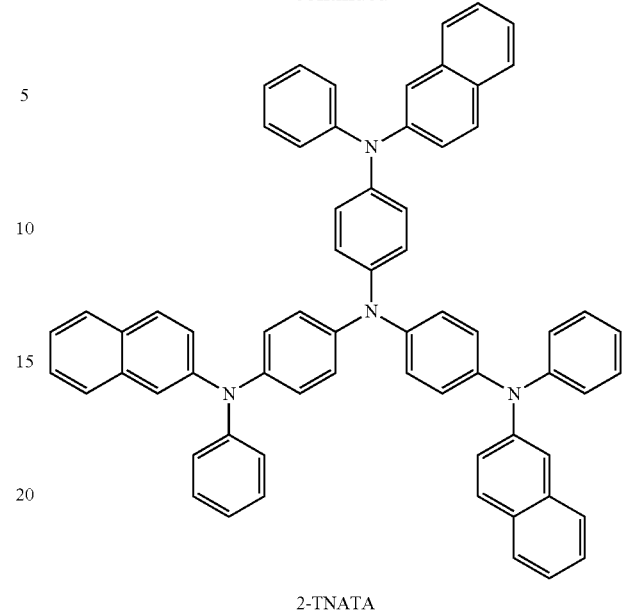

2-TNATA

The thickness of the HIL may be from about 100 Å to about 10000 Å, and in some embodiments, may be from about 100 Å to about 1000 Å. When the thickness of the HIL is within these ranges, the HIL may have good hole injecting ability without a substantial increase in driving voltage.

Next, the HTL may be formed on the HIL using various methods, for example, vacuum deposition, spin coating, casting, LB deposition, or the like. When the HTL is formed using vacuum deposition or spin coating, the conditions for deposition and coating may be similar to those for the formation of the HIL, though the conditions for the deposition and coating may vary according to the material that is used to form the HTL.

Any known hole-transporting material, for example, TPD (see the formula below), or NPB (see the formula below), may be used to form the HTL.

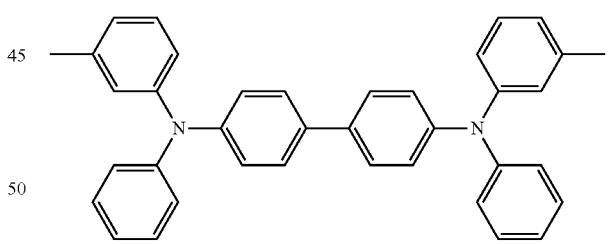

TPD

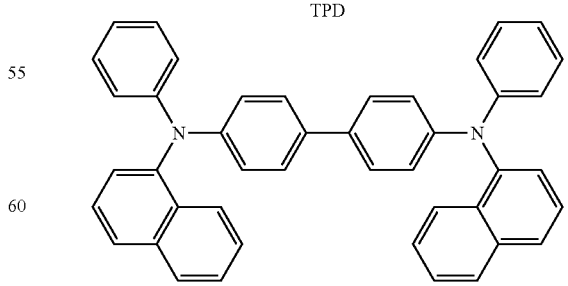

NPB

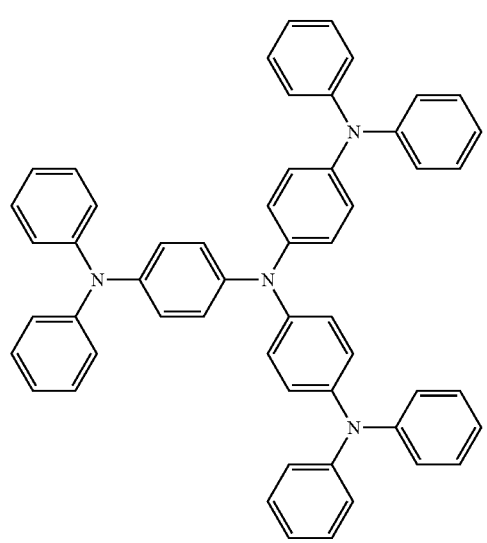

TDATA

The thickness of the HTL may be from about 50 Å to about 1000 Å, and in some embodiments, may be from about 100 Å to about 800 Å. When the thickness of the HTL is within these ranges, the HTL may have good hole transporting ability without a substantial increase in driving voltage.

Then, the EML may be formed on the HTL by using vacuum deposition, spin coating, casting, LB deposition, or the like. When the EML is formed using vacuum deposition or spin coating, the deposition and coating conditions may be similar to whose for the formation of the HIL, though the conditions for deposition and coating may vary according to the material that is used to form the EML.

The EML may include the heterocyclic compound represented by Formula 1 above as a host or a dopant. In some embodiments the EML may further include a known host or dopant, in addition to the heterocyclic compound of Formula 1 above. Non-limiting examples of suitable hosts include 4,4'-N,N'-dicarbazole-biphenyl (CPB), ADN (see the formula below), TPBI (see the formula below), TBADN (see the formula below), and E3 (see the formula below).

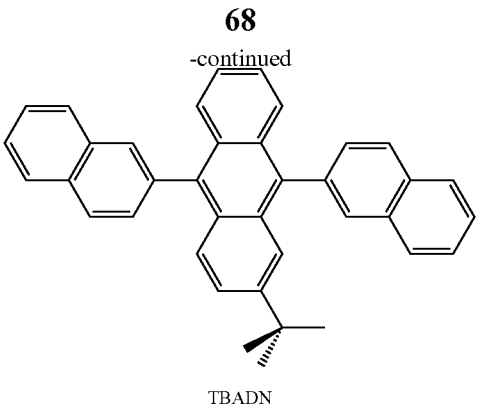

TBADN

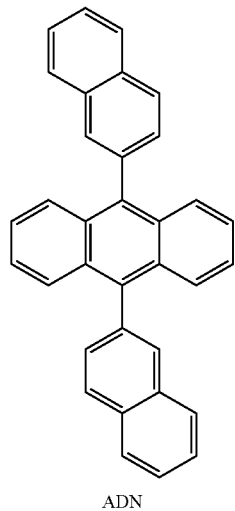

ADN

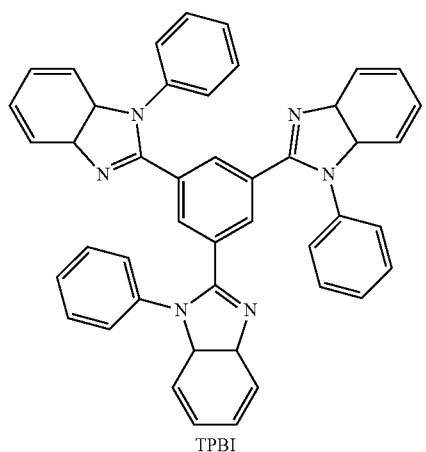

TPBI

E3

Non-limiting examples of suitable red dopants include PtOEP (see the formula below), Ir(piq)$_3$ (see the formula below), and Btp$_2$Ir(acac) (see the formula below).

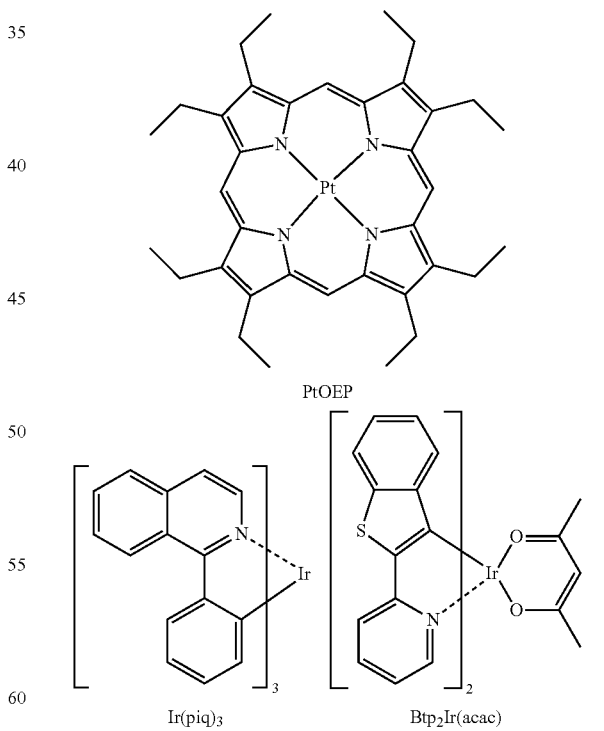

PtOEP

Ir(piq)$_3$      Btp$_2$Ir(acac)

Non-limiting examples of suitable green dopants include Ir(ppy)$_3$ (ppy=phenylpyridine, see the formula below), Ir(ppy)$_2$(acac) (see the formula below), and Ir(mpyp)$_3$ (see the formula below).

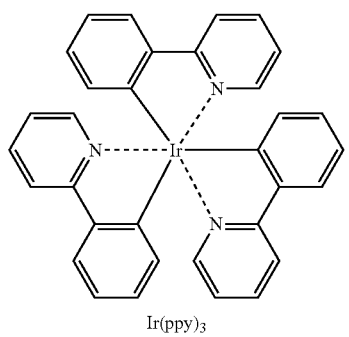

Ir(ppy)₃

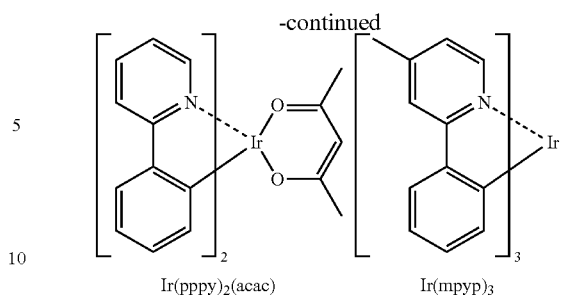

Ir(pppy)₂(acac)  Ir(mpyp)₃

Non-limiting examples of suitable blue dopants include F₂Irpic (see the formula below), (F₂ppy)₂Ir(tmd) (see the formula below), Ir(dfppz)₃ (see the formula below), DPVBi (see the formula below), 4,4'-bis(4-diphenylaminostyryl)biphenyl (DPAVBi, see the formula below), and 2,5,8,11-tetra-tert-butyl perylene (TBPe, see the formula below).

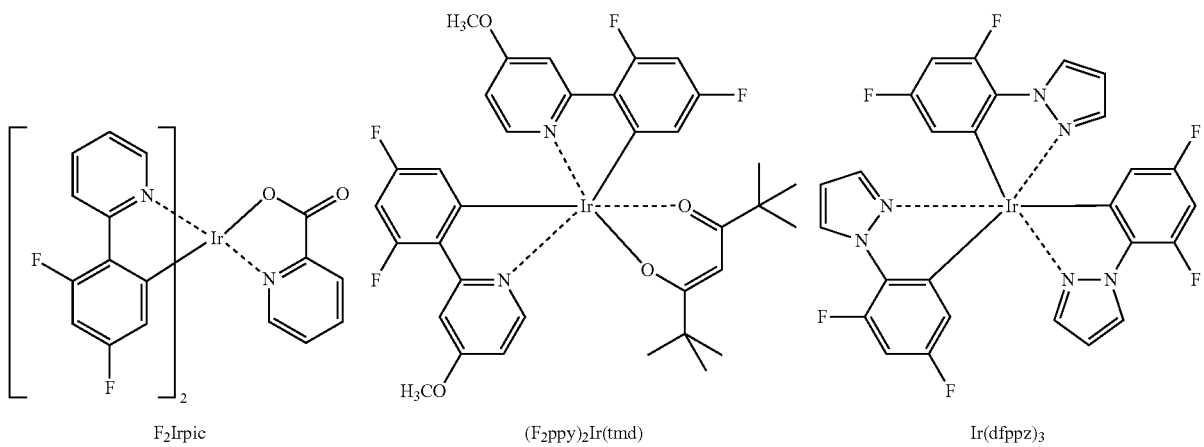

F₂Irpic  (F₂ppy)₂Ir(tmd)  Ir(dfppz)₃

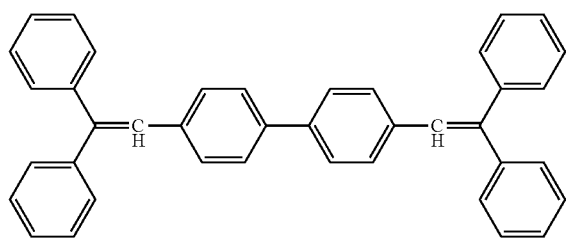

DPVBi

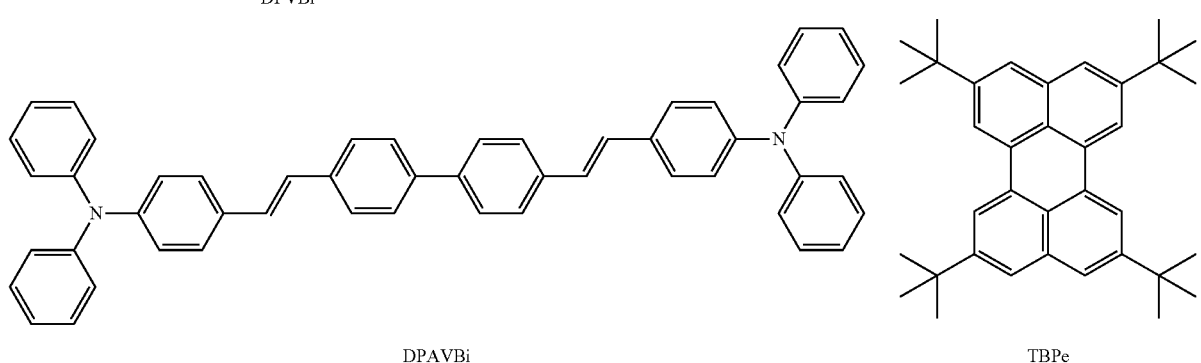

DPAVBi  TBPe

If the emission layer includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, may be from about 200 Å to about 600 Å. When the thickness of the EML is within these ranges, the EML may have good light emitting ability without a substantial increase in driving voltage.

When the EML further includes a phosphorescent dopant, a HBL may be formed between the HTL and the EML by using vacuum deposition, spin coating, casting, LB deposition, or the like, to prevent diffusion of triplet excitons or holes into an ETL. When the HBL is formed using vacuum deposition or spin coating, the conditions for deposition and coating may be similar to those for the formation of the HIL, though the conditions for deposition and coating may vary according to the material that is used to form the HBL. Any known hole-blocking material may be used. Non-limiting examples of hole-blocking materials include an oxadiazole derivative, a triazole derivative, and a phenanthroline derivative.

The thickness of the HBL may be from about 50 Å to about 1000 Å, and in some embodiments, may be from about 100 Å to about 300 Å. When the thickness of the HBL is within these ranges, the HBL may have a good hole blocking ability without a substantial increase in driving voltage.

Then, an ETL may be formed on the HBL or EML by vacuum deposition, spin coating, casting, or the like. When the ETL is formed using vacuum deposition or spin coating, the deposition or coating conditions may be similar to those applied to form the HIL, though the deposition or coating conditions may vary according to the material that is used to form the ETL. Electron-transporting materials for the ETL should be able to stably transport electrons injected from an electron injecting electrode (cathode). An example of electron-transporting materials is the heterocyclic compound of Formula 1 above. In some other embodiments any known electron-transporting material may be used. Non-limiting examples of suitable electron-transporting materials for the ETL include a quinoline derivative, such as tris(8-quinolinorate)aluminum (Alq3), TAZ (see the formula below), BAlq (see the formula below), and beryllium bis(benzoquinolin-10-olate) (Bebq$_2$).

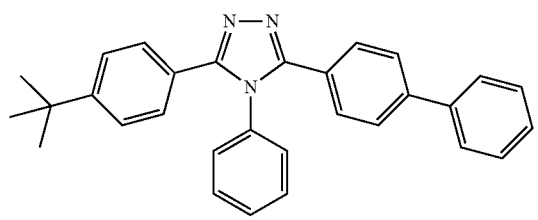

TAZ

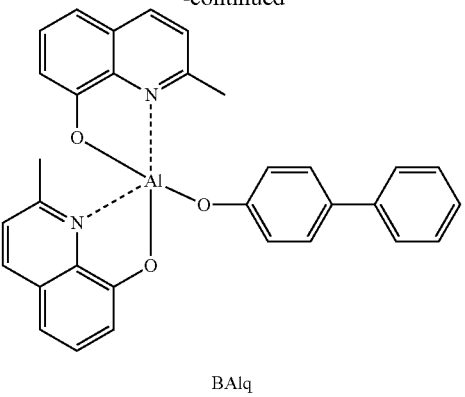

BAlq

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

Then, an EIL, which facilitates injection of electrons from the cathode, may be formed on the ETL. Any suitable electron-injecting material may be used to form the EIL.

Examples of electron-injecting materials for the EIL include LiF, NaCl, CsF, Li$_2$O, and BaO, which are known in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

Finally, the second electrode, which may be a transmission electrode, is disposed on the organic layer. The second electrode may be a cathode, which is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

According to embodiments of the present invention, the organic light-emitting device may be included in various types of flat panel display devices, such as in a passive matrix organic light-emitting display device, in an active matrix organic light-emitting display device, or in a double-screen flat display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor.

According to embodiments of the present invention, the organic light-emitting device may include a plurality of organic layers, wherein at least one of the organic layers may be formed of the heterocyclic compound of Formula 1 by using a deposition method or a wet method of coating a solution of the heterocyclic compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

Synthesis of Compound 7

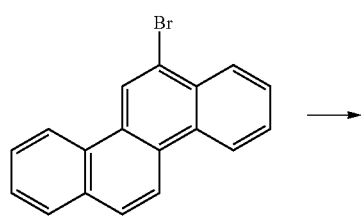

I-1

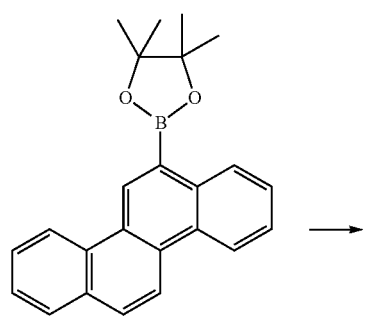

I-2

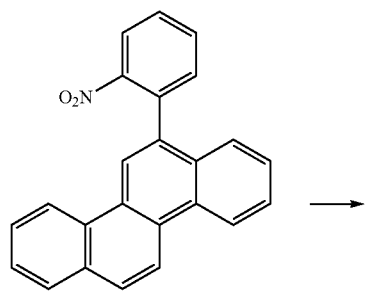

I-3

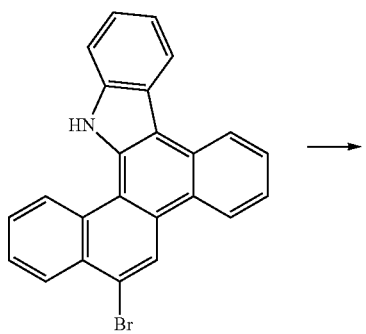

I-4

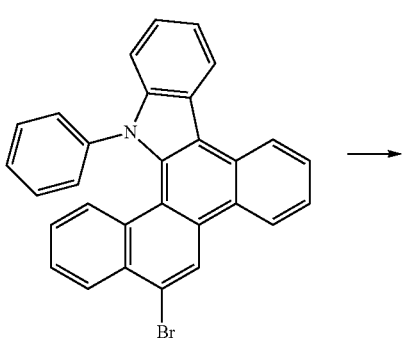

I-5

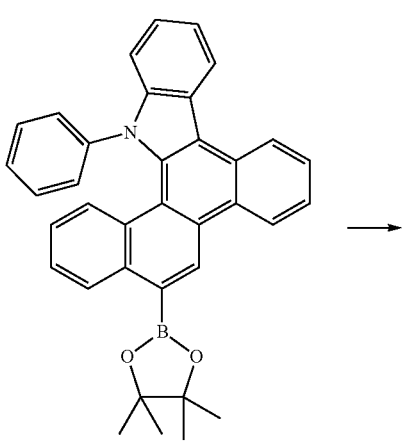

I-6

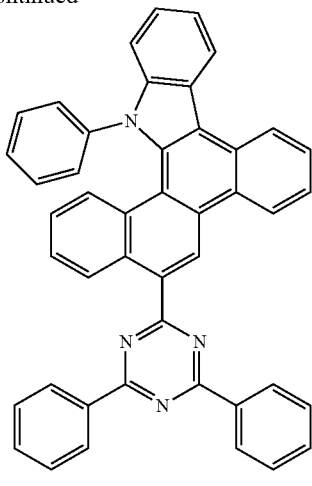

Synthesis of Intermediate I-1

3.07 g (10.0 mmol) of 6-bromochrysene, 2.54 g (10.0 mmol) of bis(pinacolato)diborone, 0.36 g (0.5 mmol) of [1,1'-bis(diphenylphosphino)ferrocene]dichloro palladium (II) (hereinafter, $PdCl_2(dppf)_2$), and 2.94 g (30.0 mmol) of KOAc were dissolved in 40 mL of dimethylsulfoxide (DMSO) to obtain a solution, which was then stirred at about 80° C. for about 6 hours. The reaction solution was cooled to room temperature, followed by extraction three times with 50 mL of water and 50 mL of diethylether. The organic phase was collected, and was dried using magnesium sulfate to evaporate the solvent. The residue was separated and purified using silica gel column chromatography to obtain 3.01 g of Intermediate I-1 (Yield: 85%) This compound was identified using liquid chromatography-mass spectroscopy (LC-MS). $C_{24}H_{23}BO_2$: M+354.2

Synthesis of Intermediate I-2

7.08 g (20.0 mmol) of Intermediate I-1, 4.04 g (20.0 mmol) of 2-bromonitrobenzene, 1.15 g (1.0 mmol) of tetrakis triphenylphosphine palladium ($Pd(PPh_3)_4$), and 8.29 g (60.0 mmol) of $K_2CO_3$ were dissolved in 60 mL of a mixed tetrahydrofuran (THF) and $H_2O$ (2:1) solution to obtain a solution, which was then stirred at about 70° C. for about 5 hours. The reaction solution was cooled to room temperature, and 40 mL of water was added thereto, followed by extraction three times with 50 mL of ethylether. The organic phase was collected, and was dried using magnesium sulfate to evaporate the solvent. The residue was separated and purified using silica gel column chromatography to obtain 6.22 g of Intermediate I-2 (Yield: 89%) This compound was identified using LC-MS. $C_{24}H_{15}NO_2$: M+349.1

Synthesis of Intermediate I-3

3.49 g (10.0 mmol) of Intermediate I-2 and 5.77 g (22 mmol) of triphenylphosphine ($PPh_3$) were dissolved in 30 mL of 1,2-dichlorobenzene to obtain a solution, which was then stirred at about 170° C. for about 12 hours. The reaction solution was cooled to room temperature, and the solvent was removed therefrom under vacuum conditions, followed by extraction three times with 50 mL of water and 50 mL of dichloromethane. The organic phase was collected, and was dried using magnesium sulfate to evaporate the solvent. The residue was separated and purified using silica gel column chromatography to obtain 2.35 g of Intermediate I-3 (Yield: 74%) This compound was identified using LC-MS. $C_{24}H_{15}N$: M+317.1

Synthesis of Intermediate I-4

4.76 g (15.0 mmol) of Intermediate I-3 was dissolved in 100 mL of dichloromethane to obtain a solution, and 1.75 mL (15.0 mmol) of bromine ($Br_2$) was slowly dropwise added to the solution at about 0° C. to obtain a reaction solution. The reaction solution was stirred at about 0° C. for about 3 hours. 60 mL of water and 30 mL of a 20% aqueous thiosodium sulfate solution were added to the reaction solution, followed by extraction three times with 80 mL of dichloromethane. The organic phase was collected, and was dried using magnesium sulfate to evaporate the solvent. The residue was separated and purified by silica gel column chromatography, followed by recrystallization with a dichloromethane/hexane solution to obtain 3.80 g of Intermediate I-4 (Yield 64%). This compound was identified using LC-MS. $C_{24}H_{14}BrN$: M+395.0

Synthesis of Intermediate I-5

3.96 g (10.0 mmol) of Intermediate I-4, 3.06 g (15.0 mmol) of iodobenzene, 0.19 g (1.0 mmol) of CuI, 0.05 g (0.2 mmol) of 18-Crown-6, and 4.15 g (30.0 mmol) of $K_2CO_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by extraction three times with 50 mL of water and 50 mL of dichloromethane. The organic phase was collected, and was dried using magnesium sulfate to evaporate the solvent. The residue was separated and purified using silica gel column chromatography to obtain 4.29 g of Intermediate I-5 (Yield: 91%) This compound was identified using LC-MS. $C_{30}H_{18}BrN$: M+471.1

Synthesis of Intermediate I-6

4.72 g (10.0 mmol) of Intermediate I-5, 2.54 g (10.0 mmol) of bis(pinacolato)diborone, 0.36 g (0.5 mmol) of [1,1'-bis(diphenylphosphino)ferrocene]dichloro palladium (II) (hereinafter, $PdCl_2(dppf)_2$), and 2.94 g (30.0 mmol) of KOAc were dissolved in 40 mL of DMSO to obtain a solution, which was then stirred at about 80° C. for about 6 hours. The reaction solution was cooled to room temperature, followed by extraction three times with 50 mL of water and 50 mL of diethylether. The organic phase was collected, and was dried using magnesium sulfate to evaporate the solvent. The residue was separated and purified using silica gel column chromatography to obtain 4.10 g of Intermediate I-6 (Yield: 79%) This compound was identified using LC-MS. $C_{36}H_{30}BNO_2$: M+519.2

Synthesis of Compound 7

2.59 g (5.0 mmol) of Intermediate I-6, 1.34 g (5.0 mmol) of 2-chloro-4,6-diphenyl-[1,3,5]-triazine, 0.29 g (0.25 mmol) of $Pd(PPh_3)_4$, and 2.07 g (15.0 mmol) of $K_2CO_3$ were dissolved in 30 mL of a mixed solution $THF/H_2O$ (2:1) to obtain a solution, which was then stirred at about 70° C. for about 5 hours. The reaction solution was cooled to room temperature, followed by extraction three times with 50 mL of water and 50 mL of diethylether. The organic phase was collected, and was dried using magnesium sulfate to evaporate the solvent. The residue was separated and purified using silica gel column chromatography to obtain 2.24 g of Compound 7 (Yield: 72%) This compound was identified using LC-MS and nuclear magnetic resonance (NMR). $C_{45}H_{28}N_4$: M+624.2

$^1$H NMR (CDCl$_3$, 400 MHz) δ (ppm) 9.31 (s, 1H), 9.01-8.98 (m, 1H), 8.83 (d, 1H), 8.67-8.63 (m, 4H), 8.52 (d, 1H), 8.43-8.40 (m, 1H), 8.20 (d, 1H), 7.71-7.61 (m, 3H), 7.51-7.25 (m, 13H), 6.84-6.79 (m, 2H)

Synthesis Example 2

Synthesis of Compound 8

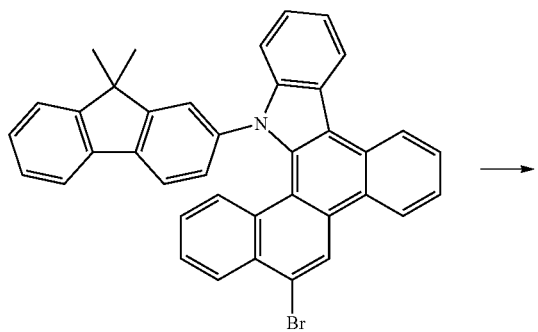

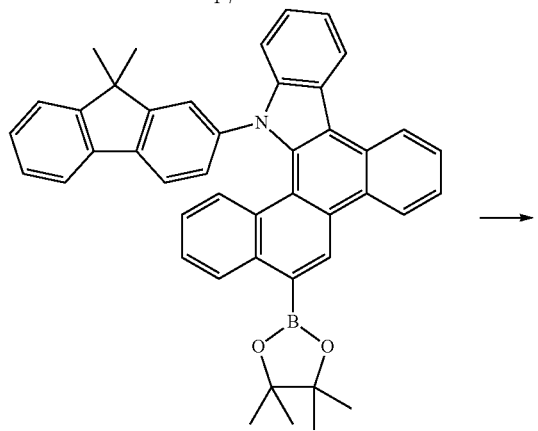

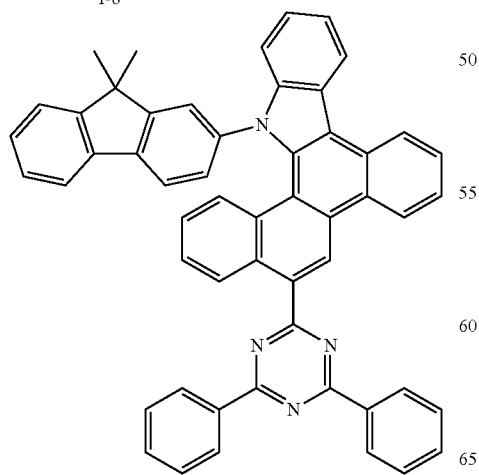

Synthesis of Intermediate I-7

5.29 g of Intermediate I-7 was synthesized from Intermediate I-4 and 2-bromo-9,9-dimethylfluorene in the same manner as in the synthesis of Intermediate I-5 (Yield: 90%). This compound was identified using LC-MS. $C_{39}H_{26}BrN$: M+587.1

Synthesis of Intermediate I-8

4.64 g of Intermediate I-8 was synthesized from Intermediate I-7 in the same manner as in the synthesis of Intermediate I-6 (Yield: 73%). This compound was identified using LC-MS. $C_{45}H_{38}BNO_2$: M+635.3

Synthesis of Compound 8

2.78 g of Compound 8 was synthesized from Intermediate I-8 in the same manner as in the synthesis of Compound 7 (Yield: 75%). This compound was identified using LC-MS and NMR. $C_{54}H_{36}N_4$: M+740.3

$^1$H NMR (CDCl$_3$, 400 MHz) δ (ppm) 9.30 (s, 1H), 9.01-8.98 (m, 1H), 8.83 (dd, 1H), 8.67-8.63 (m, 4H), 8.52 (d, 1H), 8.43-8.40 (m, 1H), 8.20 (dd, 1H), 7.82-7.80 (m, 1H), 7.69-7.58 (m, 4H), 7.52 (m, 1H), 7.46-7.21 (m, 9H), 6.95 (dt, 1H), 6.85-6.77 (m, 2H), 6.67-6.66 (m, 1H), 6.38 (dd, 1H), 1.84 (s, 6H)

Synthesis Example 3

Synthesis of Compound 13

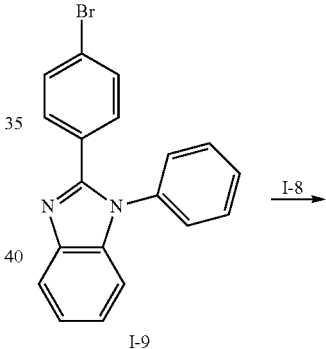

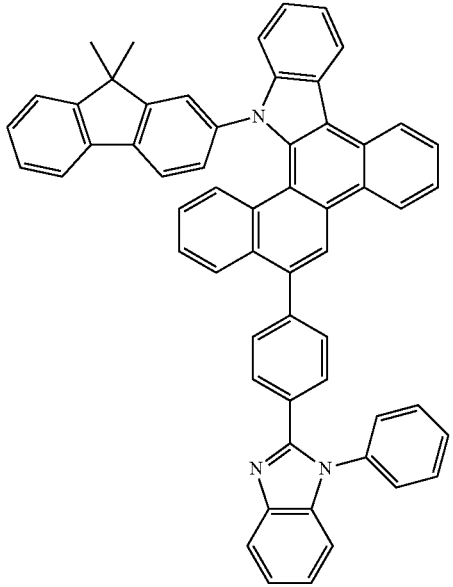

3.58 g of Compound 13 was synthesized from Intermediate I-8 and Intermediate 1-9, synthesized using a known method, in the same manner as in the synthesis of Compound 8 (Yield: 92%). This compound was identified using LC-MS and NMR. $C_{58}H_{39}N_3$: M+777.3

$^1$H NMR (CDCl$_3$, 400 MHz) δ (ppm) 9.00 (d, 1H), 8.83 (d, 1H), 8.70 (s, 1H), 8.52 (d, 1H), 8.20 (dd, 1H), 8.17-8.13 (m, 2H), 7.81 (d, 1H), 7.73-7.59 (m, 4H), 7.53-7.36 (m, 8H), 7.35-7.12 (m, 8H), 6.95 (dt, 1H), 6.85-6.76 (m, 2H), 6.67-6.65 (m, 1H), 6.39-6.35 (m, 1H), 1.83 (s, 6H)

Synthesis Example 4

Synthesis of Compound 29

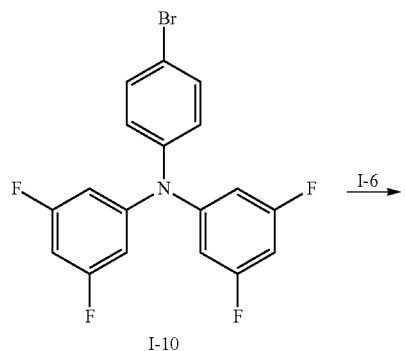

2.94 g of Compound 29 was synthesized from Intermediate I-6 and Intermediate I-10, synthesized using a known method, in the same manner as in the synthesis of Compound 13 (Yield: 83%). This compound was identified using LC-MS and NMR. $C_{48}H_{28}F_4N_2$: M+708.2

$^1$H NMR (CDCl$_3$, 400 MHz) δ (ppm) 8.99 (d, 1H), 8.89 (s, 1H), 8.73 (d, 1H), 8.42 (dd, 1H), 8.18 (dd, 1H), 7.83-7.66 (m, 3H), 7.62-7.52 (m, 5H), 7.46-7.32 (m, 5H), 6.96-6.89 (m, 2H), 6.74-6.58 (m, 8H)

Synthesis Example 5

Synthesis of Compound 37

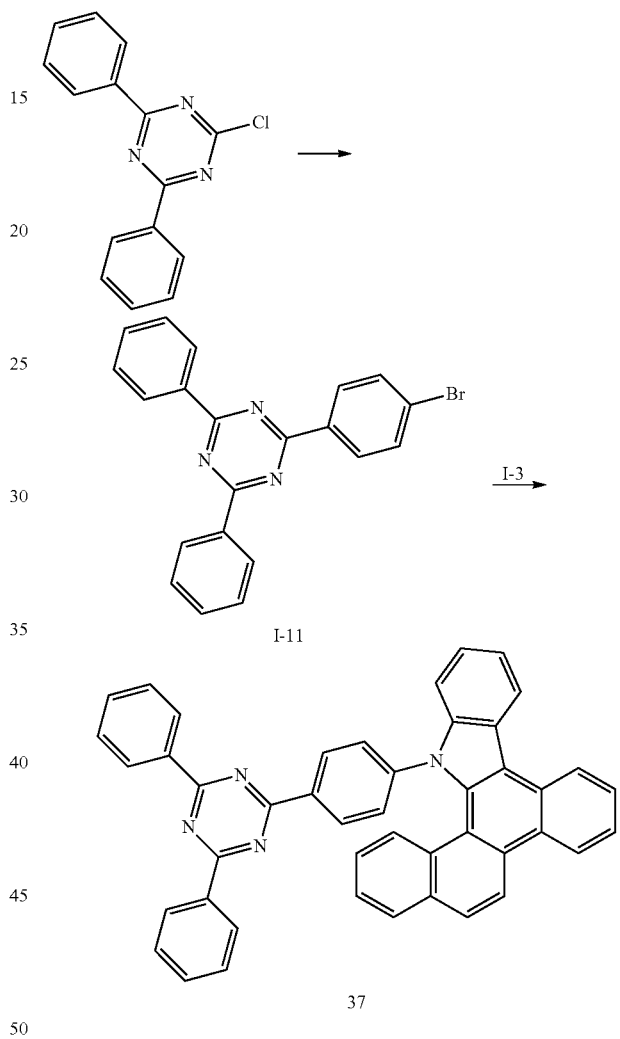

Synthesis of Intermediate I-11

2.68 g (10 mmol) of 2-chloro-4,6-diphenyl-[1,3,5]-triazine, 3.00 g (15.0 mmol) of 4-bromophenyl-1-boronic acid, 0.58 g (0.5 mmol) of Pd(PPh$_3$)$_4$, and 4.14 g (30.0 mmol) of K$_2$CO$_3$ were dissolved in 60 mL of a mixed solution THF/H$_2$O (2:1) to obtain a solution, which was then stirred at about 70° C. for about 5 hours. The reaction solution was cooled to room temperature, followed by extraction three times with 60 mL of water and 60 mL of diethylether. The organic phase was collected, and was dried using magnesium sulfate to evaporate the solvent. The residue was separated and purified using silica gel column chromatography to obtain 2.56 g of Intermediate I-11 (Yield: 66%) This compound was identified using LC-MS. $C_{21}H_{14}BrN_3$: M+387.0

Synthesis of Compound 37

1.59 g (5 mmol) of Intermediate I-3, 2.14 g (1.5 mmol) of Intermediate I-11, 0.08 g (0.5 mmol) of CuI, 0.025 g (0.1 mmol) of 18-Crown-6, and 2.07 g (30.0 mmol) of $K_2CO_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by extraction three times with 50 mL of water and 50 mL of dichloromethane. The organic phase was collected, and was dried using magnesium sulfate to evaporate the solvent. The residue was separated and purified using silica gel column chromatography to obtain 2.72 g of Compound 37 (Yield: 81%) This compound was identified using LC-MS and NMR. $C_{45}H_{28}N_4$: M+624.2

$^1$H NMR (CDCl$_3$, 400 MHz) δ (ppm) 9.08 (d, 1H), 8.81 (d, 1H), 8.70-8.63 (m, 7H), 8.56 (dd, 1H), 8.25 (m, 1H), 8.05 (d, 1H), 7.82 (m, 1H), 7.68 (dt, 1H), 7.63 (dt, 1H), 7.52-7.25 (m, 9H), 6.89-6.79 (m, 4H)

Synthesis Example 6

Synthesis of Compound 64

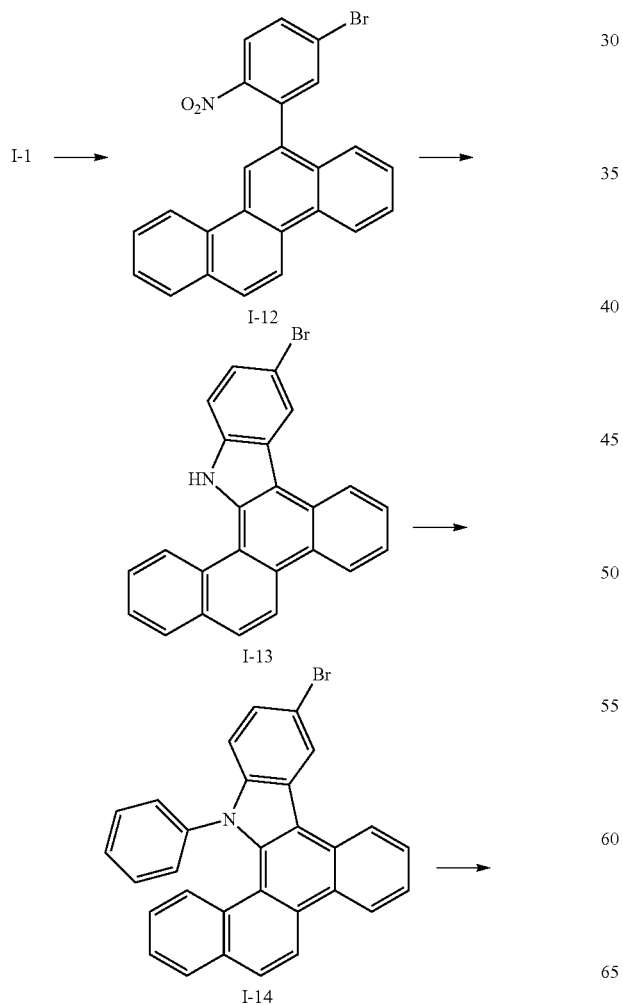

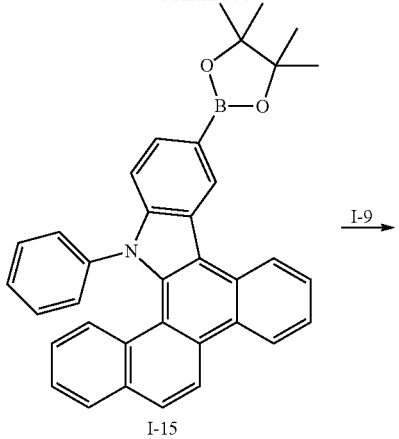

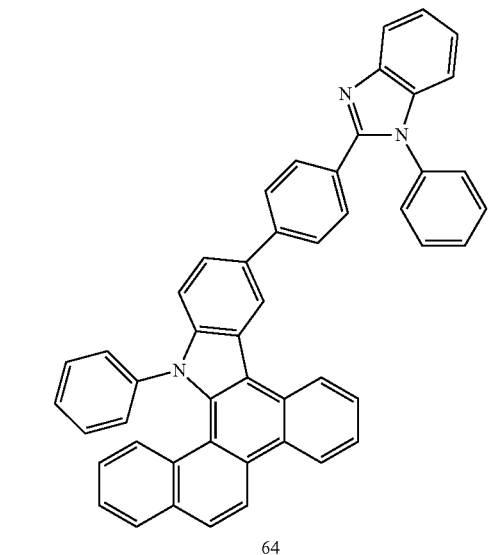

Synthesis of Intermediate I-12

2.66 g of Intermediate I-12 was synthesized from Intermediate I-1 and 2,4-dibromo-1-nitrobenzene in the same manner as in the synthesis of Intermediate I-2 (Yield: 62%). This compound was identified using LC-MS. $C_{24}H_{14}BrNO_2$: M+427.0

Synthesis of Intermediate I-13

3.25 g of Intermediate I-13 was synthesized from Intermediate I-12 in the same manner as in the synthesis of Intermediate I-3 (Yield: 82%). This compound was identified using LC-MS. $C_{24}H_{14}BrN$: M+395.0

Synthesis of Intermediate I-14

4.20 g of Intermediate I-14 was synthesized from Intermediate I-13 in the same manner as in the synthesis of Intermediate I-5 (Yield: 89%). This compound was identified using LC-MS. $C_{30}H_{18}BrN$: M+471.1

Synthesis of Intermediate I-15

3.95 g of Intermediate I-15 was synthesized from Intermediate I-14 in the same manner as in the synthesis of Intermediate I-6 (Yield: 76%). This compound was identified using LC-MS. $C_{36}H_{30}BNO_2$: M+519.2

Synthesis of Compound 64

2.75 g of Compound 64 was synthesized from Intermediate I-9 and Intermediate 1-15 in the same manner as in the synthesis of Compound 29 (Yield: 83%). This compound was identified using LC-MS and NMR. $C_{49}H_{31}N_3$: M+661.3

$^1$H NMR (CDCl$_3$, 400 MHz) δ (ppm) 9.06 (d, 1H), 8.78 (d, 1H), 8.63 (d, 1H), 8.49 (d, 1H), 8.19-8.16 (m, 2H), 8.03 (d, 1H), 7.91 (d, 1H), 7.82 (dd, 1H), 7.75-7.59 (m, 3H), 7.51-7.23 (m, 16H), 7.17-7.11 (m, 1H), 7.00-6.97 (m, 1H), 6.88 (dt, 1H)

Synthesis Example 7

Synthesis of Compound 65

2.25 g of Compound 65 was synthesized from Intermediate I-15 and 2-chloro-4,6-diphenyl-[1,3,5]-triazine in the same manner as in the synthesis of Compound 64 (Yield: 72%). This compound was identified using LC-MS and NMR. $C_{45}H_{28}N_4$: M+624.2

$^1$H NMR (CDCl$_3$, 400 MHz) δ (ppm) 9.03 (d, 1H), 8.82-8.76 (m, 2H), 8.68-8.53 (m, 6H), 8.48 (d, 1H), 8.46-8.43 (m, 1H), 8.07 (d, 1H), 7.85-7.82 (m, 1H), 7.78 (dt, 1H), 7.64-7.60 (m, 1H), 7.49-7.31 (m, 12H), 6.96 (dt, 1H)

Synthesis Example 8

Synthesis of Compound 68

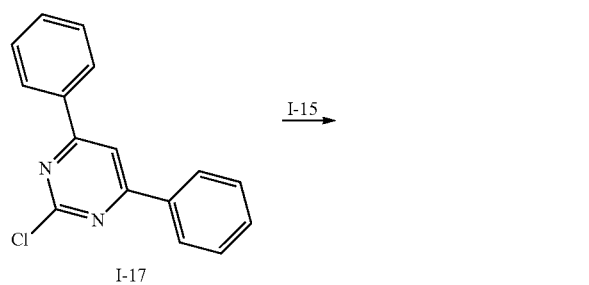

2.15 g of Compound 68 was synthesized from Intermediate I-15 and Intermediate 1-17 (2-chloro-4,6-diphenylpyrimi-dine) in the same manner as in the synthesis of Compound 64 (Yield: 69%). This compound was identified using LC-MS and NMR. $C_{46}H_{29}N_3$: M+623.2

$^1$H NMR (CDCl$_3$, 400 MHz) δ (ppm) 8.96 (d, 1H), 8.78 (d, 1H), 8.59 (dt, 2H), 8.49-8.43 (m, 2H), 8.32-8.30 (m, 1H), 8.10 (d, 1H), 7.99-7.92 (m, 6H), 7.82 (dd, 1H), 7.76 (s, 1H), 7.68-7.60 (m, 2H), 7.54-7.46 (m, 5H), 7.39-7.30 (m, 5H), 6.87 (dt, 1H)

Synthesis Example 9

Synthesis of Compound 69

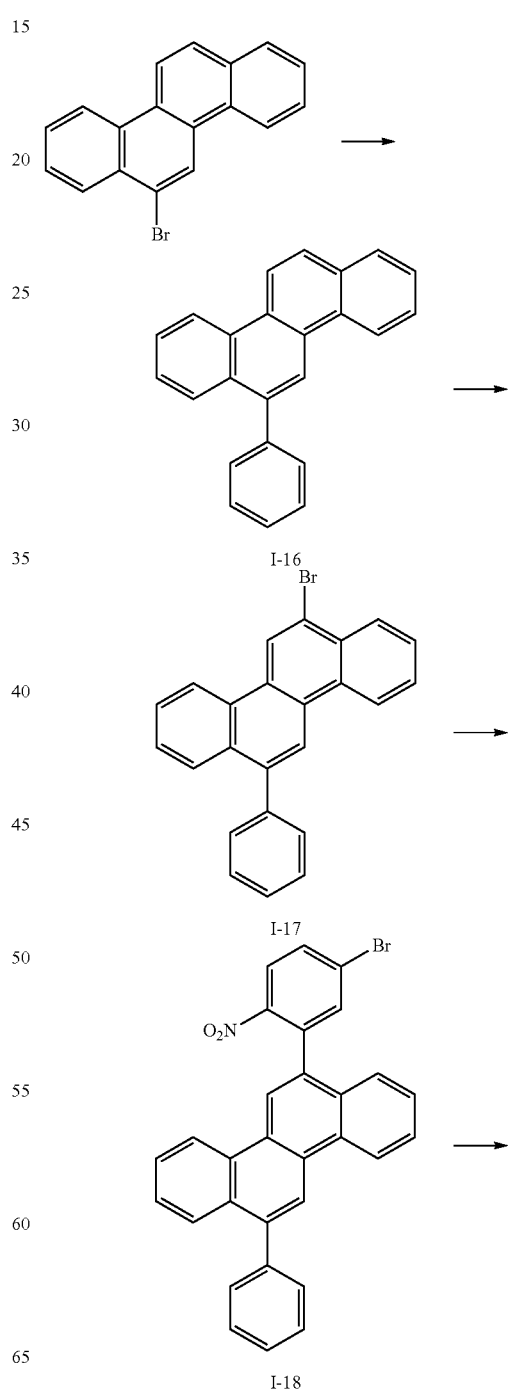

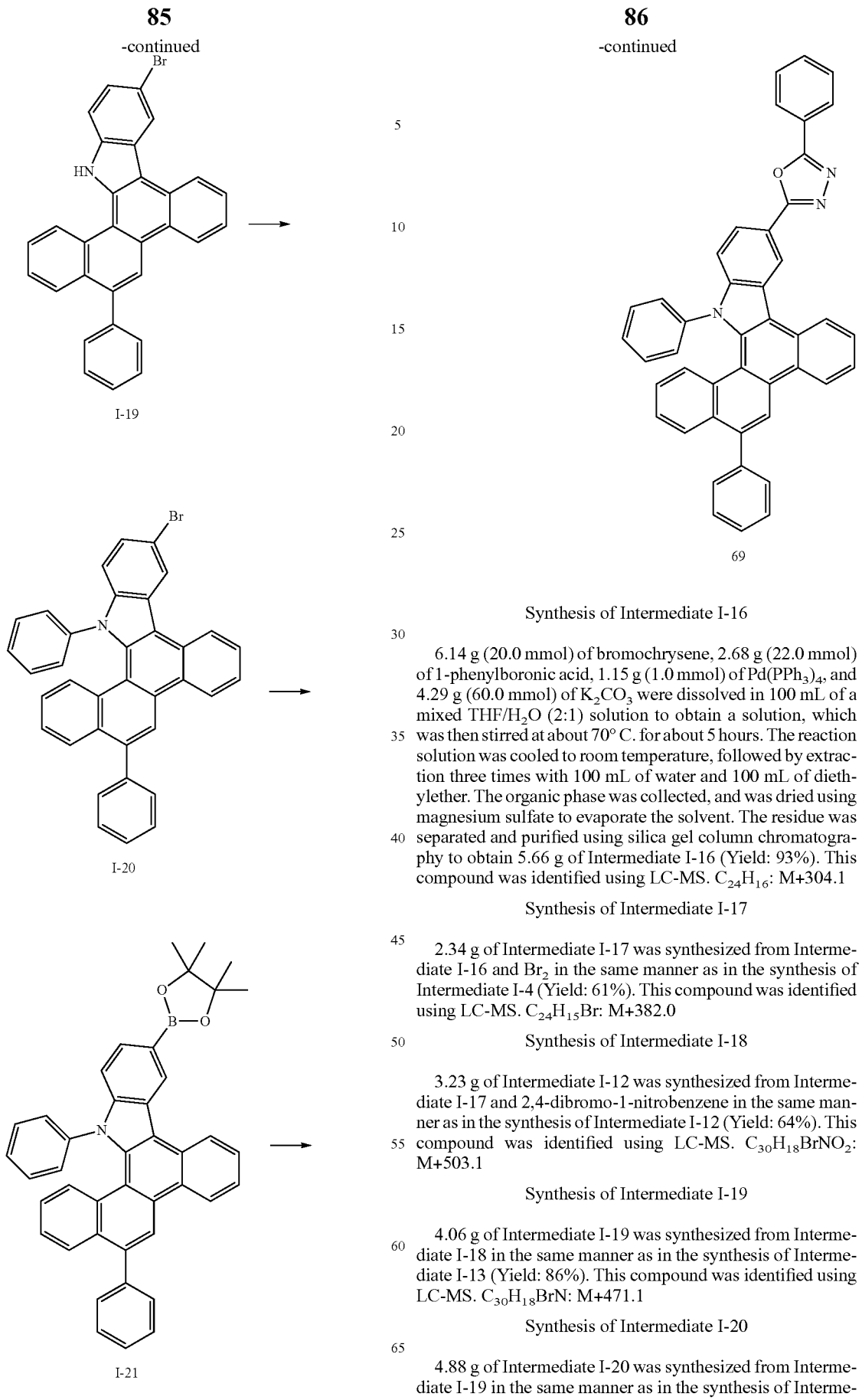

Synthesis of Intermediate I-16

6.14 g (20.0 mmol) of bromochrysene, 2.68 g (22.0 mmol) of 1-phenylboronic acid, 1.15 g (1.0 mmol) of Pd(PPh$_3$)$_4$, and 4.29 g (60.0 mmol) of K$_2$CO$_3$ were dissolved in 100 mL of a mixed THF/H$_2$O (2:1) solution to obtain a solution, which was then stirred at about 70° C. for about 5 hours. The reaction solution was cooled to room temperature, followed by extraction three times with 100 mL of water and 100 mL of diethylether. The organic phase was collected, and was dried using magnesium sulfate to evaporate the solvent. The residue was separated and purified using silica gel column chromatography to obtain 5.66 g of Intermediate I-16 (Yield: 93%). This compound was identified using LC-MS. C$_{24}$H$_{16}$: M+304.1

Synthesis of Intermediate I-17

2.34 g of Intermediate I-17 was synthesized from Intermediate I-16 and Br$_2$ in the same manner as in the synthesis of Intermediate I-4 (Yield: 61%). This compound was identified using LC-MS. C$_{24}$H$_{15}$Br: M+382.0

Synthesis of Intermediate I-18

3.23 g of Intermediate I-12 was synthesized from Intermediate I-17 and 2,4-dibromo-1-nitrobenzene in the same manner as in the synthesis of Intermediate I-12 (Yield: 64%). This compound was identified using LC-MS. C$_{30}$H$_{18}$BrNO$_2$: M+503.1

Synthesis of Intermediate I-19

4.06 g of Intermediate I-19 was synthesized from Intermediate I-18 in the same manner as in the synthesis of Intermediate I-13 (Yield: 86%). This compound was identified using LC-MS. C$_{30}$H$_{18}$BrN: M+471.1

Synthesis of Intermediate I-20

4.88 g of Intermediate I-20 was synthesized from Intermediate I-19 in the same manner as in the synthesis of Intermediate I-14 (Yield: 89%). This compound was identified using LC-MS. $C_{36}H_{22}BrN$: M+547.1

Synthesis of Intermediate I-21

4.70 g of Intermediate I-21 was synthesized from Intermediate I-20 in the same manner as in the synthesis of Intermediate I-15 (Yield: 79%). This compound was identified using LC-MS. $C_{42}H_{34}BNO_2$: M+595.3

Synthesis of Compound 69

2.33 g of Compound 69 was synthesized from Intermediate I-21 and 2-bromo-5-phenyl-[1,3,4]-oxadiazole in the same manner as in the synthesis of Compound 64 (Yield: 76%). This compound was identified using LC-MS and NMR. $C_{44}H_{27}N_3O$: M+613.2

$^1$H NMR (CDCl$_3$, 400 MHz) δ (ppm) 8.99 (d, 1H), 8.75 (s, 1H), 8.70 (d, 1H), 8.47 (d, 1H), 8.31-8.26 (m, 2H), 8.22 (s, 1H), 8.15-8.09 (m, 2H), 7.72-7.62 (m, 4H), 7.56-7.42 (m, 10H), 7.38-7.31 (m, 3H), 6.84 (dt, 1H)

Synthesis Example 10

Synthesis of Compound 79

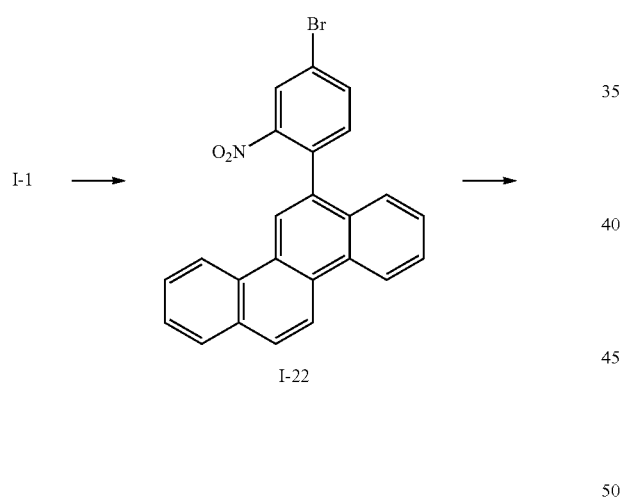

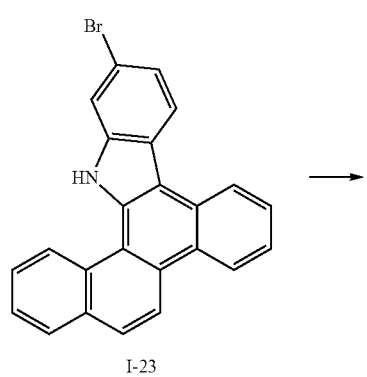

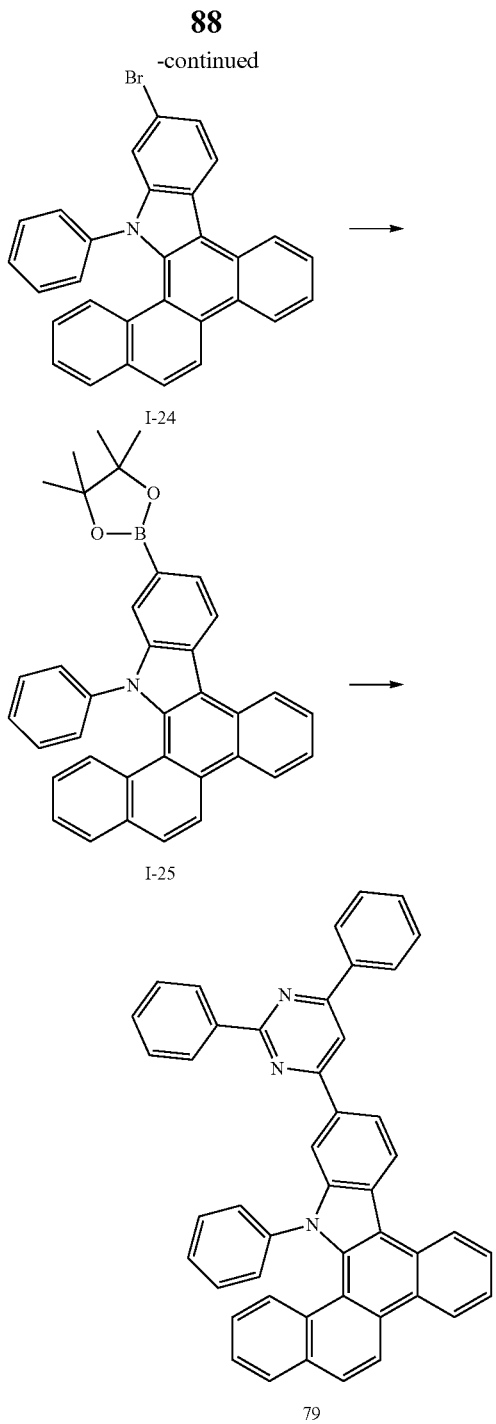

Synthesis of Intermediate I-22

5.74 g of Intermediate I-22 was synthesized from Intermediate I-1 and 1.4-dibromo-2-nitrobenzene in the same manner as in the synthesis of Intermediate I-18 (Yield: 67%). This compound was identified using LC-MS. $C_{24}H_{14}BrNO_2$: M+427.0

Synthesis of Intermediate I-23

3.53 g of Intermediate I-23 was synthesized from Intermediate I-22 in the same manner as in the synthesis of Intermediate I-19 (Yield: 89%). This compound was identified using LC-MS. $C_{24}H_{14}BrN$: M+395.0

Synthesis of Intermediate I-24

4.29 g of Intermediate I-24 was synthesized from Intermediate I-23 in the same manner as in the synthesis of Intermediate I-20 (Yield: 91%). This compound was identified using LC-MS. $C_{30}H_{18}BrN$: M+471.1

Synthesis of Intermediate I-25

3.95 g of Intermediate I-25 was synthesized from Intermediate I-24 in the same manner as in the synthesis of Intermediate I-21 (Yield: 76%). This compound was identified using LC-MS. $C_{36}H_{30}BNO_2$: M+519.2

Synthesis of Compound 79

2.25 g of Compound 79 was synthesized from Intermediate I-25 and 2-chloro-4,6-diphenyl-[1,3,5]-triazine in the same manner as in the synthesis of Compound 69 (Yield: 72%). This compound was identified using LC-MS and NMR. $C_{45}H_{28}N_4$: M+624.2

$^1$H NMR (CDCl$_3$, 400 MHz) δ (ppm) 9.06 (d, 1H), 8.84 (d, 1H), 8.65 (d, 5H), 8.56 (d, 1H), 8.35-8.33 (m, 2H), 8.23 (d, 1H), 8.01 (d, 1H), 7.85 (dd, 1H), 7.66 (dt, 1H), 7.59 (dt, 1H), 7.48-7.27 (m, 12H), 6.83 (dt, 1H)

Synthesis Example 11

Synthesis of Compound 86

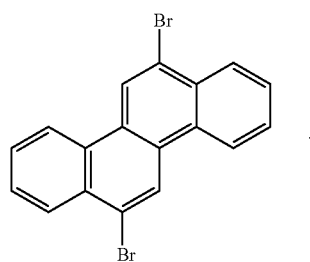

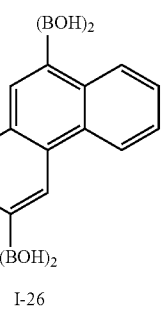

I-26

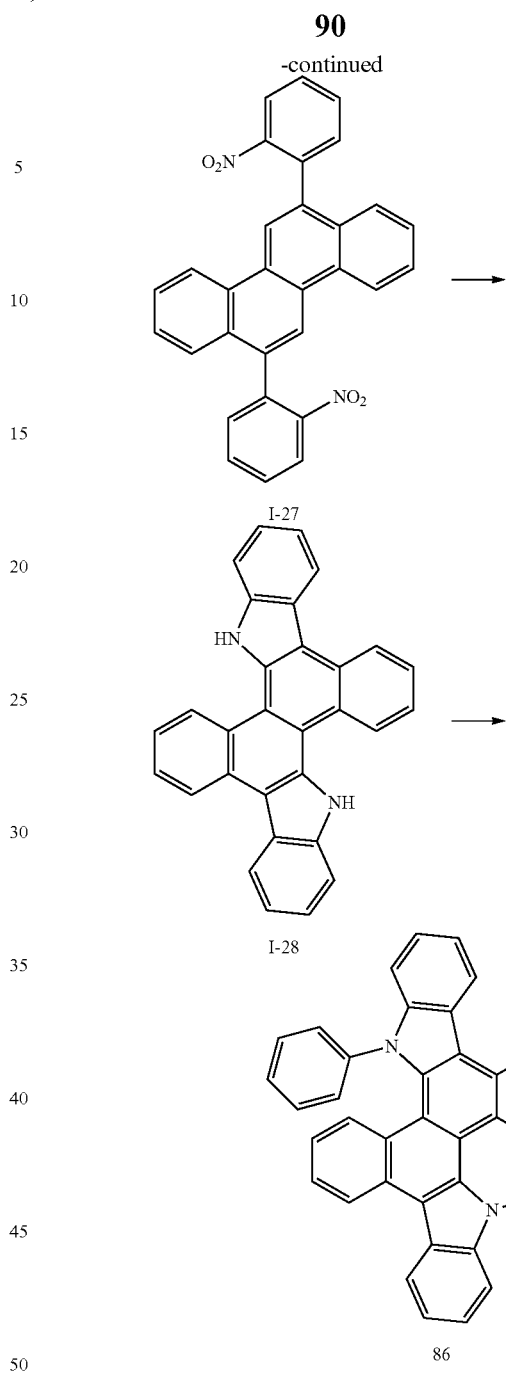

Synthesis of Intermediate I-26

3.86 g (10.0 mmol) of 6,12-dibromochrysene was dissolved in 30 mL of THF and then 8 mL of n-butyllithium (n-BuLi, 2.5M in hexane) was slowly added thereto at a temperature of −78° C. to obtain a solution, which was then stirred at the same temperature for about 1 hour. Then, 2.78 mL (25 mmol) of B(OMe)$_3$ was slowly added thereto. The temperature was slowly raised to room temperature, followed by further stirring for about 3 hours. After the reaction was completed, 20 mL of a 10% HCl aqueous solution was added, followed by extraction three times with 30 mL of EtOAc and 40 mL of water. The organic phase was collected and was dried using magnesium sulfate to evaporate the solvent. The residue was recrystallized using diethylether to obtain 2.67 g of Intermediate I-26 (Yield: 79%) This compound was identified using LC-MS. $C_{18}H_{14}B_4O_4$: M+338.1

Synthesis of Intermediate I-27

3.86 g of Intermediate I-27 was synthesized from Intermediate I-26 and 2-bromonitrobenzene in the same manner as in the synthesis of Intermediate I-2 (Yield: 82%). This compound was identified using LC-MS. $C_{30}H_{18}N_2O_4$: M+470.1

Synthesis of Intermediate I-28

2.97 g of Intermediate I-28 was synthesized from Intermediate I-27 in the same manner as in the synthesis of Intermediate I-3 (Yield: 73%). This compound was identified using LC-MS. $C_{30}H_{16}N_2$: M+406.1

Synthesis of Compound 86

2.43 g of Compound 86 was synthesized from Intermediate I-28 in the same manner as in the synthesis of Intermediate I-5 (Yield: 87%). This compound was identified using LC-MS and NMR. $C_{42}H_{26}N_2$: M+558.2

$^1$H NMR (CDCl$_3$, 400 MHz) δ (ppm) 8.66-8.60 (m, 2H), 8.22 (dd, 2H), 8.01-7.97 (m, 2H), 7.63-7.40 (m, 8H), 7.38-7.23 (m, 6H), 7.03-6.83 (m, 5H), 6.82-6.78 (m, 1H)

Synthesis Example 12

Synthesis of Compound 94

3.19 g of Compound 94 was synthesized from Intermediate I-28 and 9-bromophenanthrene in the same manner as in the synthesis of Compound 86 (Yield: 84%). This compound was identified using LC-MS and NMR. $C_{58}H_{34}N_2$: M+758.3

$^1$H NMR (CDCl$_3$, 400 MHz) δ (ppm) 8.67-8.60 (m, 4H), 8.47 (d, 2H), 8.36-8.33 (m, 2H), 8.19 (dd, 2H), 8.07 (s, 2H), 8.01-7.97 (m, 2H), 7.68-7.55 (m, 6H), 7.48 (dt, 2H), 7.41 (dt, 2H), 7.35-7.22 (m, 4H), 6.95-6.82 (m, 4H), 6.80-6.76 (m, 2H)

Synthesis Example 13

Synthesis of Compound 99

3.32 g of Compound 99 was synthesized from Intermediate I-28 and 2-bromo-9,9-dimethylfluorene in the same manner as in the synthesis of Compound 86 (Yield: 84%). This compound was identified using LC-MS and NMR. $C_{60}H_{42}N_2$: M+790.3

$^1$H NMR (CDCl$_3$, 400 MHz) δ (ppm) 8.66-8.61 (m, 2H), 8.22-8.18 (m, 2H), 8.03-7.99 (m, 2H), 7.83-7.78 (m, 2H), 7.60 (d, 2H), 7.54 (dd, 2H), 7.37-7.19 (m, 6H), 6.99-6.83 (m, 6H), 6.78 (dd, 2H), 6.68 (dd, 2H), 6.38 (dd, 2H), 1.82 (s, 12H)

Synthesis Example 14

Synthesis of Compound 107

3.35 g of Compound 107 was synthesized from Intermediate I-28 and 4-bromotriphenylamine in the same manner as in the synthesis of Compound 86 (Yield: 75%). This compound was identified using LC-MS and NMR. $C_{66}H_{44}N_4$: M+892.4

$^1$H NMR (CDCl$_3$, 400 MHz) δ (ppm) 8.58 (dd, 2H), 8.18 (dd, 2H), 7.96 (dd, 2H), 7.80-7.76 (m, 4H), 7.42-7.28 (m, 12H), 6.98-7.82 (m, 6H), 6.68 (dt, 4H), 6.43 (d, 4H), 6.22 (dd, 8H)

Synthesis Example 15

Synthesis of Compound 109

3.30 g of Compound 109 was synthesized from Intermediate I-28 and 4-bromophenyl-2-fluorophenyl-o-tolylamine in the same manner as in the synthesis of Compound 86 (Yield: 69%). This compound was identified using LC-MS and NMR. $C_{68}H_{46}F_2N_4$: M+956.4

$^1$H NMR (CDCl$_3$, 400 MHz) δ (ppm) 8.62 (dd, 2H), 8.24 (dd, 2H), 7.99 (dd, 2H), 7.78 (d, 4H), 7.38-6.90 (m, 20H), 6.86 (d, 2H), 6.68 (dd, 2H), 6.32 (d, 4H), 6.21 (dt, 2H), 2.01 (s, 6H)

Synthesis Example 16

Synthesis of Compound 116

2.91 g of Compound 116 was synthesized from Intermediate I-28 and 4-bromophenyl-4-pyridinyl-o-tolylamine in the same manner as in the synthesis of Compound 86 (Yield: 63%). This compound was identified using LC-MS and NMR. $C_{66}H_{46}N_6$: M+922.4

$^1$H NMR (CDCl$_3$, 400 MHz) δ (ppm) 8.62 (dd, 2H), 8.23 (dd, 2H), 8.15-8.11 (m, 4H), 7.99 (dd, 2H), 7.81-7.74 (m, 4H), 7.42-7.22 (m, 6H), 7.17 (dt, 2H), 7.03-6.86 (m, 6H), 6.82 (dd, 2H), 6.72 (dd, 4H), 6.62 (d, 2H), 6.41-6.30 (m, 4H), 2.00 (6H)

Synthesis Example 17

Synthesis of Compound 119

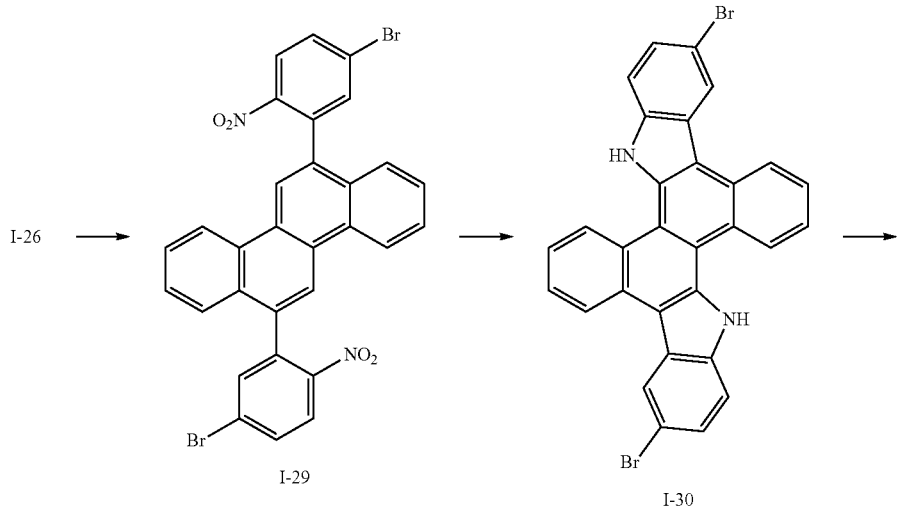

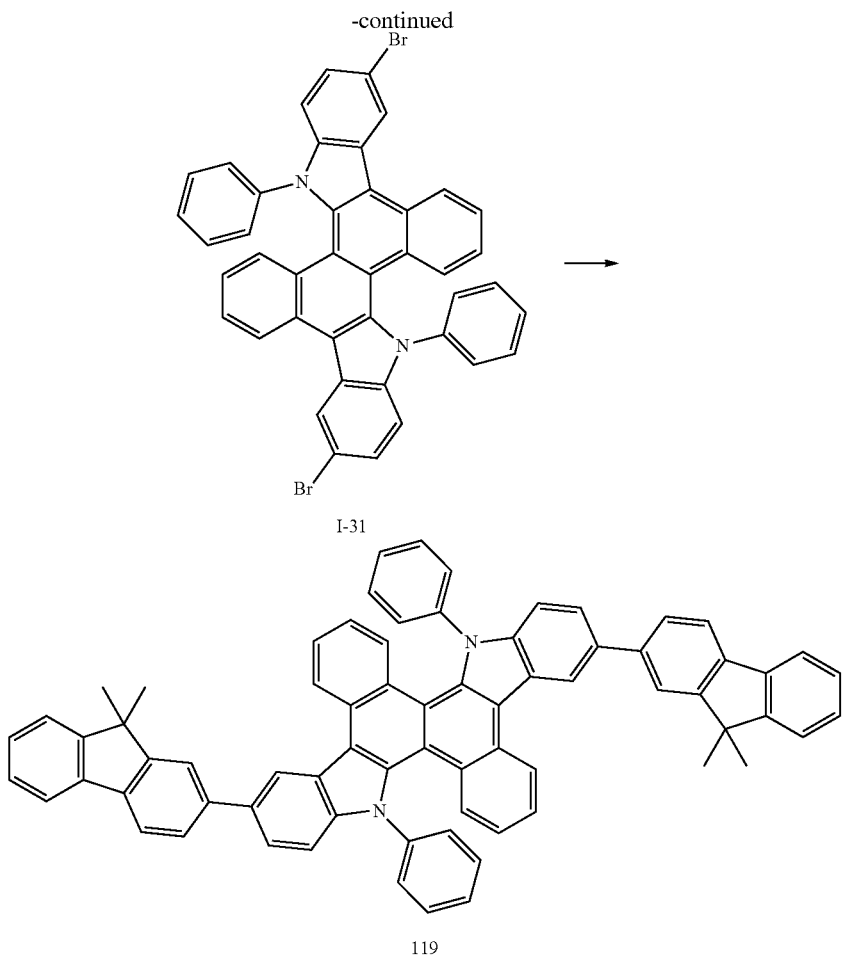

Synthesis of Intermediate I-29

4.02 g of Intermediate I-29 was synthesized from Intermediate I-26 and 2.4-dibromo-1-nitrobenzene in the same manner as in the synthesis of Intermediate I-27 (Yield: 64%). This compound was identified using LC-MS. $C_{30}H_{16}Br_2N_2O_4$: M+625.9

Synthesis of Intermediate I-30

4.34 g of Intermediate I-30 was synthesized from Intermediate I-29 in the same manner as in the synthesis of Intermediate I-28 (Yield: 77%). This compound was identified using LC-MS. $C_{30}H_{16}Br_2N_2$: M+562.0

Synthesis of Intermediate I-31

6.09 g of Intermediate I-31 was synthesized from Intermediate I-30 in the same manner as in the synthesis of Compound 86 (Yield: 85%). This compound was identified using LC-MS. $C_{42}H_{24}Br_2N_2$: M+714.0

Synthesis of Compound 119

3.58 g (5.0 mmol) of Intermediate I-31, 1.31 g (5.5 mmol) of 9,9-dimethylfluorene-2-boronic acid, 0.29 g (0.25 mmol) of Pd(PPh$_3$)$_4$, and 2.07 g (15.0 mmol) of K$_2$CO$_3$ were dissolved in 30 mL of a mixed solution THF/H$_2$O (2:1) to obtain a solution, which was then stirred at about 70° C. for about 5 hours. The reaction solution was cooled to room temperature, and 30 mL of water was added thereto, followed by extraction three times with 30 mL of ethylether. The organic phase was collected, and was dried using magnesium sulfate to evaporate the solvent. The residue was separated and purified using silica gel column chromatography to obtain 3.44 g of Compound 119 (Yield: 73%) This compound was identified using LC-MS and NMR. $C_{72}H_{50}N_2$: M+942.4

$^1$H NMR (CDCl$_3$, 400 MHz) δ (ppm) 8.98 (dd, 2H), 8.58 (dd, 2H), 7.89 (d, 2H), 7.78 (dd, 2H), 7.65 (dd, 2H), 7.54-7.42 (m, 10H), 7.38-7.30 (m, 2H), 7.22 (dt, 2H), 7.05-6.84 (m, 14H), 1.85 (s, 12H)

Example 1

To manufacture an anode, a coming 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

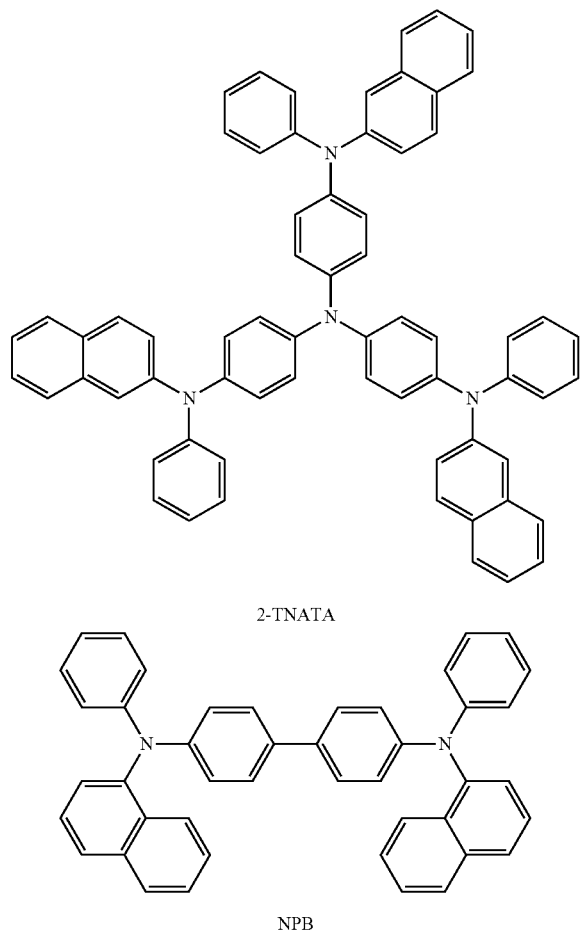

2-TNATA

NPB

Then, a green fluorescent host Alq3 and a green fluorescent dopant C545T were deposited at the same time in a weight ratio of 98:2, on the HTL, to form an EML with a thickness of 300 Å.

Then, Compound 7 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of 5.65V at a current density of 50 mA/cm$^2$, a high luminosity of 8,350 cd/m$^2$, color coordinates of (0.313, 0.644), and a luminescent efficiency of 16.7 cd/A.

Example 2

An organic light-emitting device was manufactured in the same manner as in Example 1, except that Compound 8 was used, instead of Compound 7, to form the ETL.

The organic light-emitting device had a driving voltage of 5.60V at a current density of 50 mA/cm$^2$, a high luminosity of 8,460 cd/m$^2$, color coordinates of (0.311, 0.643), and a luminescent efficiency of 16.92 cd/A.

Example 3

An organic light-emitting device was manufactured in the same manner as in Example 1, except that Compound 13 was used, instead of Compound 7, to form the ETL.

The organic light-emitting device had a driving voltage of 5.73V at a current density of 50 mA/cm$^2$, a high luminosity of 8,967 cd/m$^2$, color coordinates of (0.311, 0.641), and a luminescent efficiency of 17.93 cd/A.

Example 4

An organic light-emitting device was manufactured in the same manner as in Example 1, except that Compound 37 was used, instead of Compound 7, to form the ETL.

The organic light-emitting device had a driving voltage of 5.42V at a current density of 50 mA/cm$^2$, a high luminosity of 8,684 cd/m$^2$, color coordinates of (0.310, 0.644), and a luminescent efficiency of 17.37 cd/A.

Example 5

An organic light-emitting device was manufactured in the same manner as in Example 1, except that Compound 64 was used, instead of Compound 7, to form the ETL.

The organic light-emitting device had a driving voltage of 5.81V at a current density of 50 mA/cm$^2$, a high luminosity of 8,692 cd/m$^2$, color coordinates of (0.311, 0.643), and a luminescent efficiency of 17.38 cd/A.

Example 6

An organic light-emitting device was manufactured in the same manner as in Example 1, except that Compound 65 was used, instead of Compound 7, to form the ETL.

The organic light-emitting device had a driving voltage of 5.65V at a current density of 50 mA/cm$^2$, a high luminosity of 8,262 cd/m$^2$, color coordinates of (0.311, 0.643), and a luminescent efficiency of 16.52 cd/A.

Example 7

An organic light-emitting device was manufactured in the same manner as in Example 1, except that Compound 68 was used, instead of Compound 7, to form the ETL.

The organic light-emitting device had a driving voltage of 5.62V at a current density of 50 mA/cm$^2$, a high luminosity of 8,354 cd/m$^2$, color coordinates of (0.311, 0.643), and a luminescent efficiency of 16.71 cd/A.

Example 8

An organic light-emitting device was manufactured in the same manner as in Example 1, except that Compound 69 was used, instead of Compound 7, to form the ETL.

The organic light-emitting device had a driving voltage of 6.12V at a current density of 50 mA/cm$^2$, a high luminosity of 7,684 cd/m$^2$, color coordinates of (0.311, 0.643), and a luminescent efficiency of 15.37 cd/A.

Example 9

An organic light-emitting device was manufactured in the same manner as in Example 1, except that Compound 79 was used, instead of Compound 7, to form the ETL.

The organic light-emitting device had a driving voltage of 5.67V at a current density of 50 mA/cm$^2$, a high luminosity of 7,958 cd/m$^2$, color coordinates of (0.311, 0.643), and a luminescent efficiency of 15.92 cd/A.

Example 10

To manufacture an anode, a coming 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

A blue fluorescent host 9,10-di-naphthalene-2-yl-anthracene (ADN) and Compound 29, which is a blue fluorescent dopant, were deposited at the same time on the HTL in a weight ratio of 98:2 to form an EML having a thickness of 300A.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of 6.24V at a current density of 50 mA/cm², a luminosity of 2,890 cd/m², and a luminescent efficiency of 5.78 cd/A, and emitted blue light.

Comparative Example 1

An organic light-emitting device was manufactured in the same manner as in Example 1, except that Alq3 was used, instead of Compound 7, to form the ETL.

The organic light-emitting device had a driving voltage of 7.45V at a current density of 50 mA/cm², a high luminosity of 6,102 cd/m², color coordinates of (0.309, 0.642), which are almost the same as those of the organic light-emitting device of Example 1, and a luminescent efficiency of 12.2 cd/A.

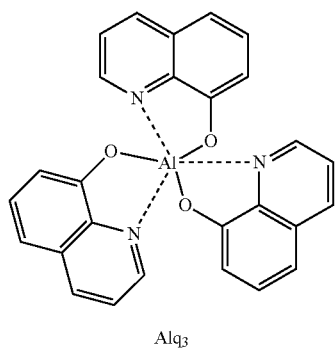

Alq3

Comparative Example 2

An organic light-emitting device was manufactured in the same manner as in Example 10, except that a blue fluorescent dopant 1,4-bis-(2,2-diphenylvinyl)biphenyl (DPVBi) was used, instead of Compound 29, to form the EML.

The organic light-emitting device had a driving voltage of 7.85V at a current density of 50 mA/cm², a luminosity of 1,560 cd/m², and a luminescent efficiency of 3.12 cd/A, and emitted blue light.

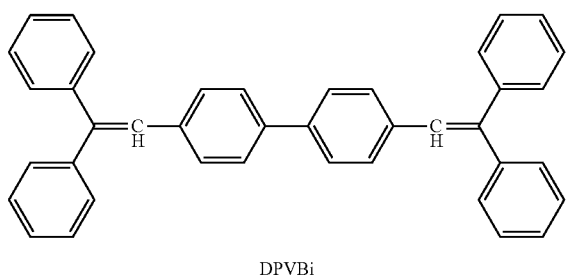 [SMILES: C(=C(c1ccccc1)c1ccccc1)c1ccc(-c2ccc(C=C(c3ccccc3)c3ccccc3)cc2)cc1 ; "DPVBi"]

DPVBi

The organic light-emitting devices including the heterocyclic compounds of Formula 1 as ETL or EML materials had a driving voltage that was lower by 1V or greater than devices manufactured using Alq3, and thus had higher efficiency and good I-V-L characteristics. In particular, lifetime characteristics were markedly improved in the organic light-emitting devices of Examples 1 through 9, as compared to the organic light-emitting device of Comparative Example 1. The organic light-emitting device of Example 10 manufactured by using Compound 29 as a blue fluorescent dopant for the EML had a driving voltage that was lower by 1.5V or greater as compared to the organic light-emitting device manufactured using DPVBi, and thus had higher efficiency and good I-V-L characteristics. In addition, the organic light-emitting device of Example 10 had lifetime characteristics markedly improved from the organic light-emitting device including DPVBi.

The characteristics of the organic light-emitting devices of Examples 1-10 and Comparative Examples 1 and 2 are tabled in Table 1 below.

TABLE 1

| | EML or ETL material | Driving voltage Driving voltage (V) | Current density (mA/cm²) | Luminocity (cd/m²) | Luminescent efficiency (cd/A) | Color of light | Half-life span (hr @ 100 mA/cm²) |
|---|---|---|---|---|---|---|---|
| Example 1 | Compound 7 | 5.65 | 50 | 8350 | 16.7 | Green | 490 hr |
| Example 2 | Compound 8 | 5.60 | 50 | 8460 | 16.92 | Green | 510 hr |
| Example 3 | Compound 13 | 5.73 | 50 | 8967 | 17.93 | Green | 562 hr |

TABLE 1-continued

| | EML or ETL material | Driving voltage Driving voltage (V) | Current density (mA/cm$^2$) | Luminocity (cd/m$^2$) | Luminescent efficiency (cd/A) | Color of light | Half-life span (hr @ 100 mA/cm$^2$) |
|---|---|---|---|---|---|---|---|
| Example 4 | Compound 37 | 5.42 | 50 | 8684 | 17.37 | Green | 486 hr |
| Example 5 | Compound 64 | 5.81 | 50 | 8692 | 17.38 | Green | 557 hr |
| Example 6 | Compound 65 | 5.65 | 50 | 8262 | 16.52 | Green | 506 hr |
| Example 7 | Compound 68 | 5.62 | 50 | 8354 | 16.71 | Green | 523 hr |
| Example 8 | Compound 69 | 6.12 | 50 | 7684 | 15.37 | Green | 370 hr |
| Example 9 | Compound 79 | 5.67 | 50 | 7958 | 15.92 | Green | 397 hr |
| Example 10 | Compound 29 | 6.24 | 50 | 2890 | 5.78 | Blue | 212 hr |
| Comparative Example 1 | Alq3 | 7.45 | 50 | 6102 | 12.2 | Green | 237 hr |
| Comparative Example 2 | DPVBi | 7.85 | 50 | 1560 | 3.12 | Blue | 113 hr |

Example 11

To manufacture an anode, a coming 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

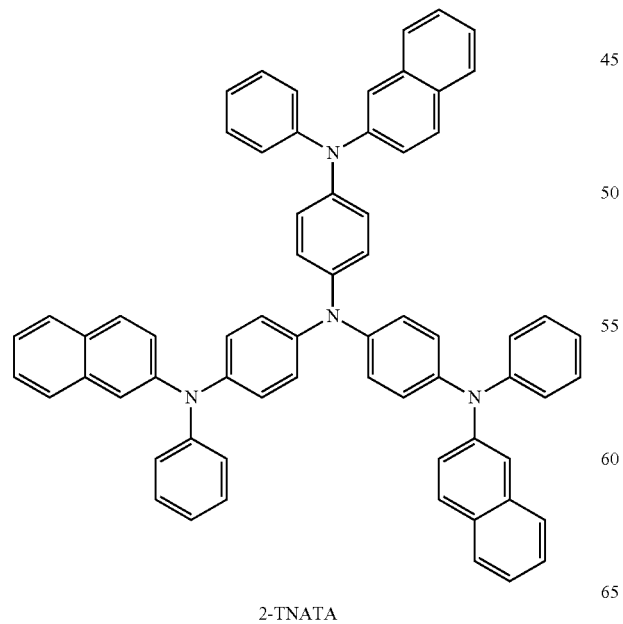

2-TNATA

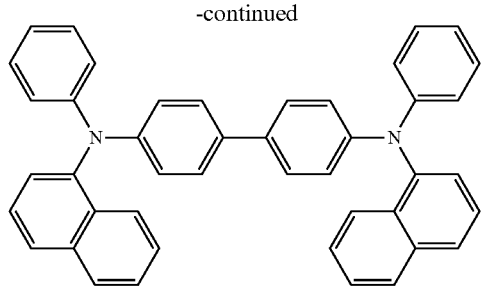

NPB

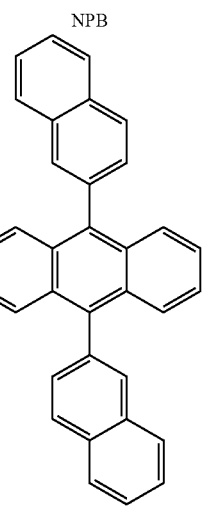

ADN

A blue fluorescent host 9,10-di-naphthalene-2-yl-anthracene (ADN) and Compound 86, which is a blue fluorescent dopant, were deposited at the same time on the HTL in a weight ratio of 98:2 to form an EML having a thickness of 300 Å.

Then, Alq3 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of 6.72V at a current density of 50 mA/cm$^2$, a luminosity of 2183 cd/m$^2$, and a luminescent efficiency of 4.37 cd/A, and emitted blue light.

Example 12

An organic light-emitting device was manufactured in the same manner as in Example 11, except that Compound 94 was used, instead of Compound 86, to form the EML.

The organic light-emitting device had a driving voltage of 6.47V at a current density of 50 mA/cm$^2$, a luminosity of 2254 cd/m$^2$, and a luminescent efficiency of 4.51 cd/A, and emitted blue light.

Example 13

An organic light-emitting device was manufactured in the same manner as in Example 11, except that Compound 99 was used, instead of Compound 86, to form the EML.

The organic light-emitting device had a driving voltage of 6.59V at a current density of 50 mA/cm$^2$, a luminosity of 2405 cd/m$^2$, and a luminescent efficiency of 4.81 cd/A, and emitted blue light.

Example 14

An organic light-emitting device was manufactured in the same manner as in Example 11, except that Compound 107 was used, instead of Compound 86, to form the EML.

The organic light-emitting device had a driving voltage of 6.31V at a current density of 50 mA/cm$^2$, a luminosity of 2590 cd/m$^2$, and a luminescent efficiency of 5.18 cd/A, and emitted blue light.

Example 15

An organic light-emitting device was manufactured in the same manner as in Example 11, except that Compound 109 was used, instead of Compound 86, to form the EML.

The organic light-emitting device had a driving voltage of 6.26V at a current density of 50 mA/cm$^2$, a luminosity of 2870 cd/m$^2$, and a luminescent efficiency of 5.74 cd/A, and emitted blue light.

Example 16

An organic light-emitting device was manufactured in the same manner as in Example 11, except that Compound 116 was used, instead of Compound 86, to form the EML.

The organic light-emitting device had a driving voltage of 6.15V at a current density of 50 mA/cm$^2$, a luminosity of 2623 cd/m$^2$, and a luminescent efficiency of 5.25 cd/A, and emitted blue light.

Example 17

An organic light-emitting device was manufactured in the same manner as in Example 11, except that Compound 119 was used, instead of Compound 86, to form the EML.

The organic light-emitting device had a driving voltage of 6.66V at a current density of 50 mA/cm$^2$, a luminosity of 2324 cd/m$^2$, and a luminescent efficiency of 4.64 cd/A, and emitted blue light.

The organic light-emitting devices including Compounds 86-119, the heterocyclic compounds of Formula 1, as EML materials had a driving voltage that was lower by 1V or greater than devices manufactured using DPVBi, and thus had higher efficiency and good I-V-L characteristics. In particular, lifetime characteristics were markedly improved in the organic light-emitting devices of Examples 11-17, as compared to the organic light-emitting device of Comparative Example 2. The characteristics of the organic light-emitting devices of Examples 11-17 and Comparative Example 2 are tabled in Table 2 below.

TABLE 2

| | EML material | Driving voltage Driving voltage (V) | Current density (mA/cm$^2$) | Luminocity (cd/m$^2$) | Luminescent efficiency (cd/A) | Color of light | Half-life span (hr @ 100 mA/cm$^2$) |
|---|---|---|---|---|---|---|---|
| Example 11 | Compound 86 | 6.72 | 50 | 2,183 | 4.37 | Blue | 209 hr |
| Example 12 | Compound 94 | 6.47 | 50 | 2,254 | 4.51 | Blue | 218 hr |
| Example 13 | Compound 99 | 6.59 | 50 | 2,405 | 4.81 | Blue | 225 hr |
| Example 14 | Compound 107 | 6.31 | 50 | 2,590 | 5.18 | Blue | 235 hr |
| Example 15 | Compound 109 | 6.26 | 50 | 2,870 | 5.74 | Blue | 210 hr |
| Example 16 | Compound 116 | 6.15 | 50 | 2,623 | 5.25 | Blue | 196 hr |
| Example 17 | Compound 119 | 6.66 | 50 | 2,324 | 4.65 | Blue | 260 hr |
| Comparative Example 2 | DPVBi | 7.85 | 50 | 1,560 | 3.12 | Blue | 113 hr |

The heterocyclic compounds of Formula 1 according to embodiments of the present invention have good light emitting characteristics and charge transporting capability, and thus, may be used as electron injecting or transporting materials that are suitable for any color fluorescent or phosphorescent devices, such as red, green, blue, and white fluorescent or phosphorescent devices, and may be used as light emitting materials for green, blue, or white fluorescent devices. Therefore, organic light-emitting devices having high efficiency, low driving voltages, high luminance, and long lifetime may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

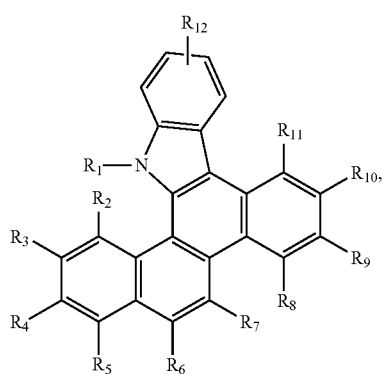

Formula 1

$R_1$ to $R_5$ and $R_8$ to $R_{12}$ in Formula 1 each being independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group, a halogen atom, a cyano group, a nitro group, a hydroxyl group, and a carboxyl group, except that $R_1$ is not a substituted or unsubstituted 4-pyridyl group, $R_6$ and $R_7$ being linked to each other to form a group represented by formula 2 in which ** and * indicates binding sites corresponding to the binding sites corresponding to the binding sites of $R_6$ and $R_7$ of Formula 1:

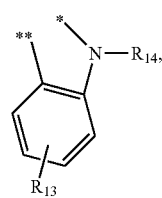

Formula 2

$R_{13}$ and $R_{14}$ in Formula 2 each being independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl or $C_2$-$C_{60}$ heterocyclic group, a substituted or unsubstituted $C_2$-$C_{60}$ heterocyclic group, a halogen atom, a cyano group, a nitro group, a hydroxyl group, or a carboxyl group; and two adjacent substituents among $R_1$ to $R_{14}$ are optionally linked to each other to form a ring.

2. The heterocyclic compound of claim 1, $R_1$ to $R_5$ and $R_8$ to $R_{14}$ in Formulae 1 and 2 being each independently selected from the group consisting of a hydrogen atom, a deuterium atom, a halogen atom, a cyano group, a $C_1$-$C_{20}$ alkyl group, and groups represented by Formulae 2a to 2l below:

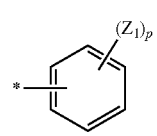

formula 2a

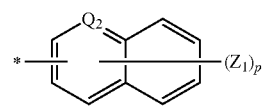

formula 2b

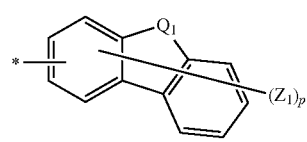

formula 2c

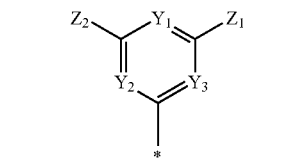

formula 2d

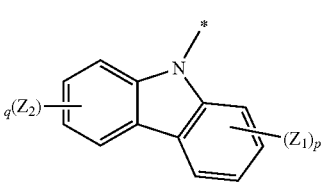

formula 2e

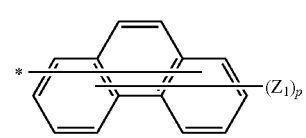

formula 2f

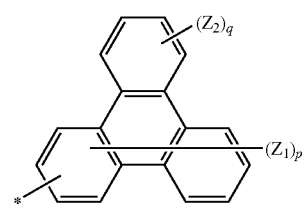

formula 2g formula 2h

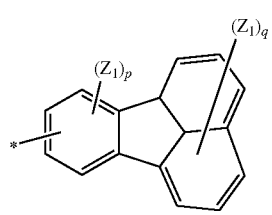

formula 2i

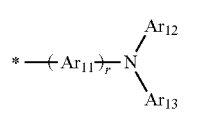

formula 2j

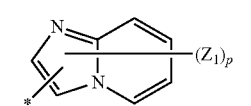

formula 2k

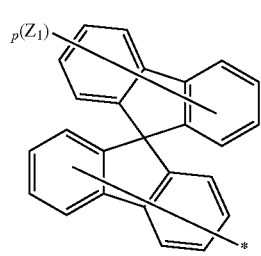

formula 2l

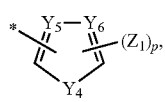

$Q_1$ and $Q_2$ in Formulae 2a to 2l each independently being a linking group selected from the group consisting of —C($R_{15}$)($R_{16}$)—, —N($R_{15}$)—, —S—, and —O—;

$Y_1, Y_2, Y_3, Y_4, Y_5$, and $Y_6$ are each independently a linking group selected from the group consisting of —N═, —C($R_{17}$)═, —S—, and —O—, except that if $R_6$ is formula 2d, then $Y_1, Y_2$ and $Y_3$ are not all —N═ and, if $R_1$ is formula 2d and $Y_1$ is —N═, then $Y_2$ and $Y_3$ are not both —C($R_{17}$)═;

$Z_1, Z_2, Ar_{12}, Ar_{13}, R_{15}, R_{16}$, and $R_{17}$ are each independently selected from the group consisting of a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_2$-$C_{20}$ heterocyclic group, a halogen atom, a cyano group, a nitro group, a hydroxyl group, and a carboxyl group;

$Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_2$-$C_{20}$ divalent heterocyclic group;

p is an integer from 1 to 12;

q is an integer from 1 to 12;

r is an integer from 0 to 5; and

* indicates a binding site.

3. The heterocyclic compound of claim 1, $R_1$ to $R_5$ and $R_8$ to $R_{14}$ in Formulae 1 and 2 being each independently selected from the group consisting of a hydrogen atom, a deuterium atom, a halogen atom, a cyano group, a methyl group, an ethyl group, a propyl group, a butyl group, a pentyl group, and groups represented by Formulae 3a to 3h below:

formula 3a formula 3b formula 3c formula 3d formula 3e formula 3f formula 3g formula 3h $Z_1, Ar_{12}$, and $Ar_{13}$ in Formulae 3a to 3h each independently being selected from the group consisting of a hydrogen atom, a deuterium atom, a substituted or unsubstituted aryl group, and a substituted or unsubstituted $C_2$-$C_{20}$ heterocyclic group;

r is an integer from 0 to 2;

p is an integer from 1 to 5; and

* indicates a binding site.

4. The heterocyclic compound of claim 1, $R_2$ to $R_5$ and $R_8$ to $R_{11}$ in Formula 1 being each independently a hydrogen atom or a deuterium atom.

5. The heterocyclic compound of claim 1, $R_2$ to $R_5$ and $R_8$ to $R_{11}$ in Formula 1 being each independently a hydrogen atom or a deuterium atom; and $R_1$, and $R_{12}$—$R_{14}$ are each independently selected from the group consisting of a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_5$-$C_{60}$ aryloxy group, a substituted or unsubstituted $C_5$-$C_{60}$ arylthio group, a substituted or unsubstituted $C_5$-$C_{60}$ aryl group, a substituted amino group with a $C_5$-$C_{60}$ aryl group or a $C_2$-$C_{60}$ heterocyclic group, a substituted or unsubstituted $C_2$-$C_{60}$ heterocyclic group.

6. The heterocyclic compound of claim 1, $R_2$ to $R_5$, and $R_8$ to $R_{11}$ in Formula 1 each being independently a hydrogen atom or a deuterium atom; and $R_1$, and $R_{12}$—$R_{14}$ each being independently selected from the group consisting of a halogen atom, a cyano group, a $C_1$-$C_{20}$ alkyl group, and groups represented by Formulae 2a to 2l below:

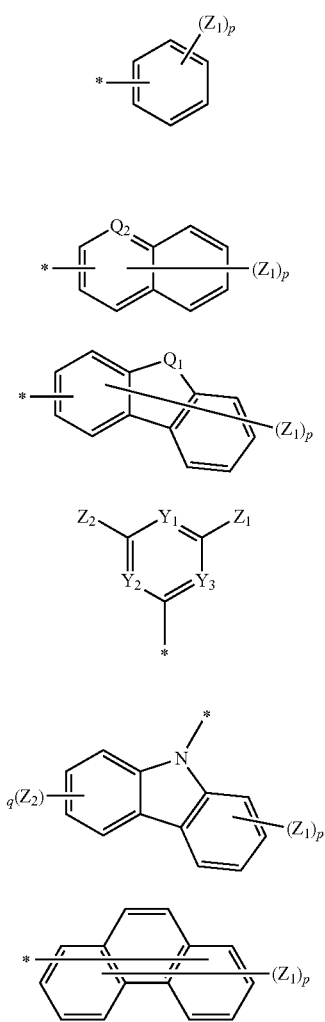

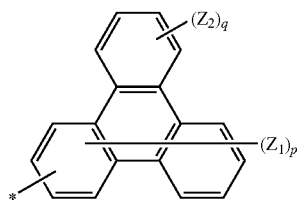

formula 2g

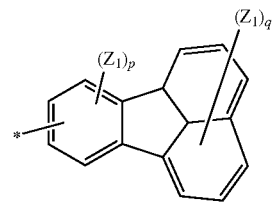

formula 2h

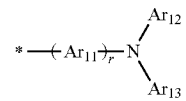

formula 2i

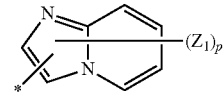

formula 2j

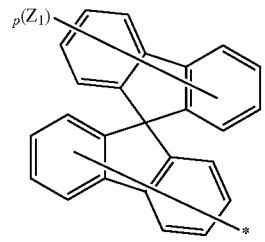

formula 2k

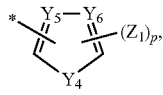

formula 2l $Q_1$ and $Q_2$ in formulae 2a to 2l being each independently a linking group selected from the group consisting of —C($R_{15}$)($R_{16}$)—, —N($R_{15}$)—, —S—, and —O—;

$Y_1, Y_2, Y_3, Y_4, Y_5$, and $Y_6$ are each independently a linking group selected from the group consisting of —N=, —C($R_{17}$)=, —S—, and —O—, except that if $R_6$ is formula 2d, then $Y_1, Y_2$ and $Y_3$ are not all —N= and, if $R_6$ and $R_7$ are not linked to each other to form a group represented by Formula 2, $R_1$ is formula 2d and $Y_1$ is —N=, then $Y_2$ and $Y_3$ are not both —C($R_{17}$)=;

$Z_1, Z_2, Ar_{12}, Ar_{13}, R_{15}, R_{16}$, and $R_{17}$ are each independently selected from the group consisting of a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_2$-$C_{20}$ heterocyclic group, a halogen atom, a cyano group, a nitro group, a hydroxyl group, and a carboxyl group;

$Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_2$-$C_{20}$ divalent heterocyclic group;

p is an integer from 1 to 12;
q is an integer from 1 to 12;
r is an integer from 0 to 5; and
* indicates a binding site.

7. The heterocyclic compound of claim 1, $R_1$, $R_2$, $R_3$, $R_4$, $R_5$ and $R_{12}$ in Formulae 1 and 2 being respectively identical with $R_{14}$, $R_8$, $R_9$, $R_{10}$, $R_{11}$ and $R_{13}$;

$R_1$ to $R_5$ and $R_8$ to $R_{14}$ being each independently selected from the group consisting of a hydrogen atom, a deuterium atom, a halogen atom, a cyano group, a methyl group, an ethyl group, a propyl group, a butyl group, a pentyl group, and groups represented by Formulae 3a to 3h below:

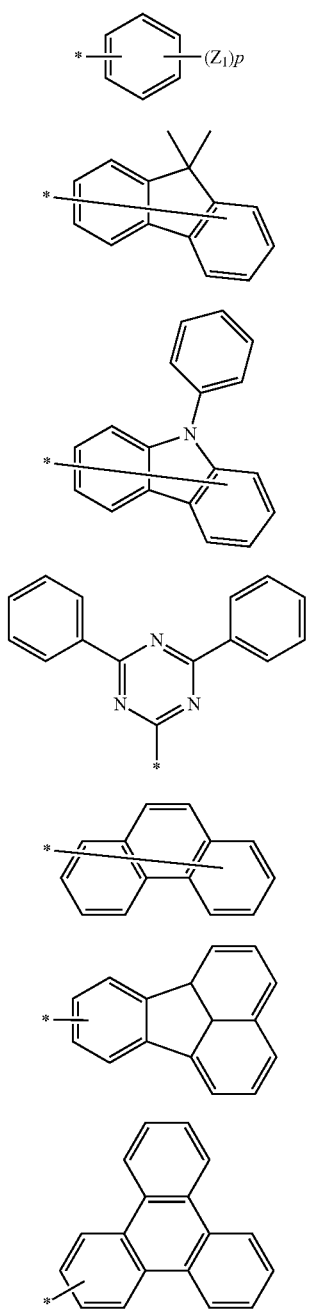

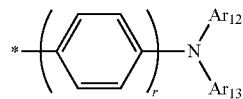

formula 3h $Z_1$, $Ar_{12}$, and $Ar_{13}$ in Formulae 3a to 3h, being each independently selected from the group consisting of a hydrogen atom, a deuterium atom, a substituted or unsubstituted aryl group, and a substituted or unsubstituted $C_2$-$C_{20}$ heterocyclic group;

r is an integer from 0 to 2;
p is an integer from 1 to 5; and
* indicates a binding site.

8. The heterocyclic compound of claims 1, $R_1$, $R_2$, $R_3$, $R_4$, $R_5$ and $R_{12}$ in Formulae 1 and 2 being respectively identical with $R_{14}$, $R_8$, $R_9$, $R_{10}$, $R_{11}$ and $R_{13}$;

$R_2$ to $R_5$ and $R_8$ to $R_{11}$ are each independently a hydrogen atom or a deuterium atom; and $R_1$, $R_{12}$, $R_{13}$ and $R_{14}$ are each independently selected from the group consisting of a hydrogen atom, a deuterium atom, a halogen atom, a cyano group, a methyl group, an ethyl group, a propyl group, a butyl group, a pentyl group, and groups represented by Formulae 3a to 3h below:

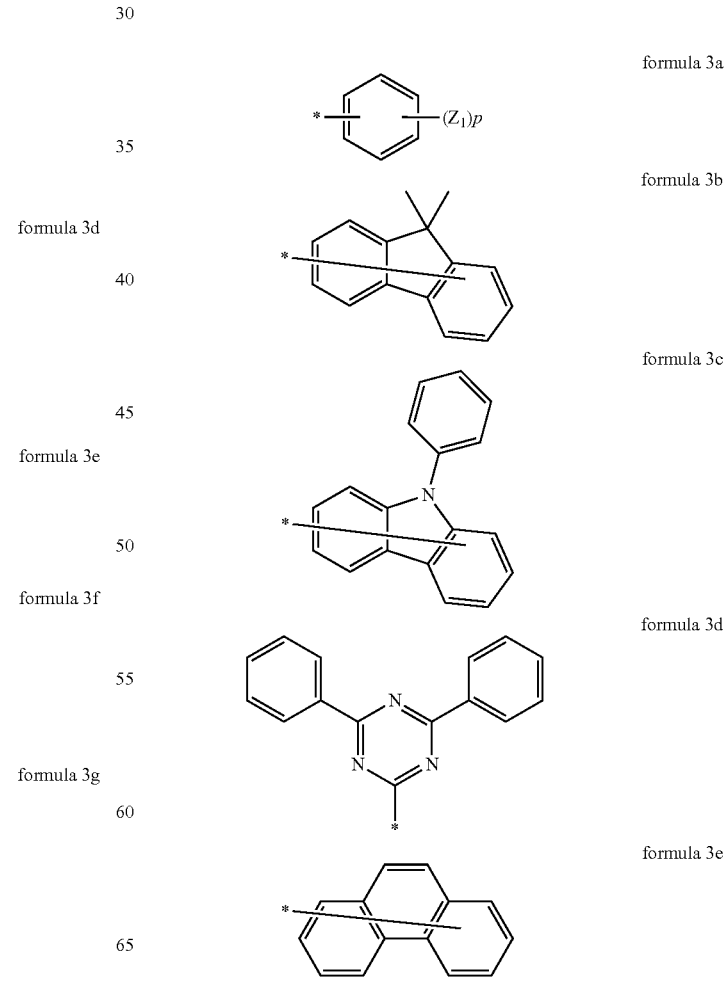

111
-continued

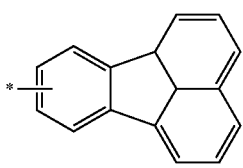 formula 3f

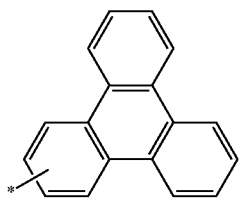 formula 3g

112
-continued

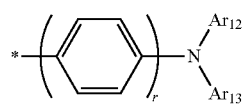 formula 3h $Z_1$, $Ar_{12}$, and $Ar_{13}$ being each independently selected from the group consisting of a hydrogen atom, a deuterium atom, a substituted or unsubstituted aryl group, and a substituted or unsubstituted $C_2$-$C_{20}$ heterocyclic group;

r is an integer from 0 to 2;

p is an integer from 1 to 5; and

* indicates a binding site.

9. The heterocyclic compound of claim 1, the heterocyclic compound of Formula 1 being one of the compounds below:

86

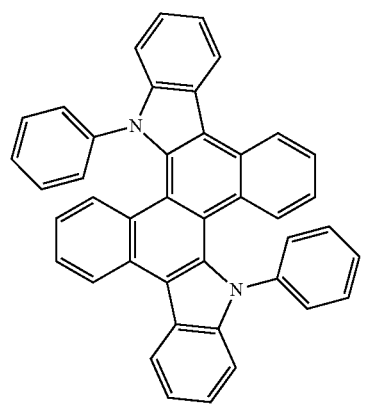

94

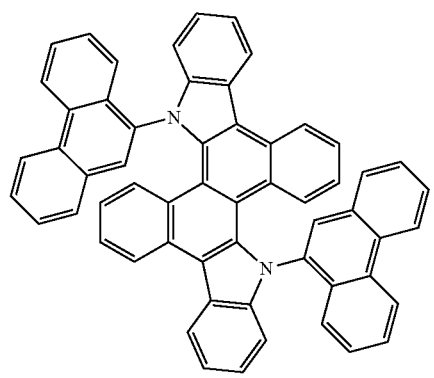

99

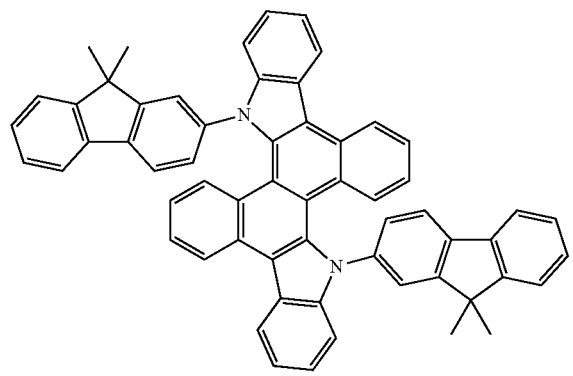

107

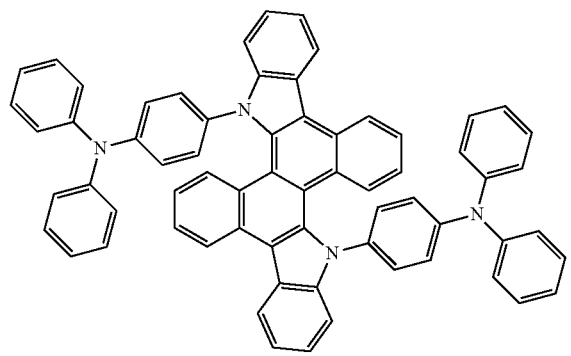

109

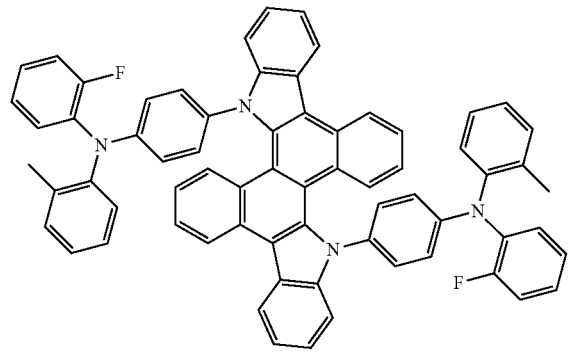

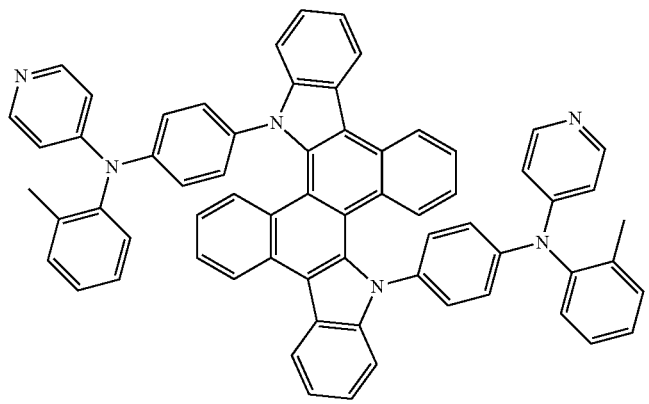

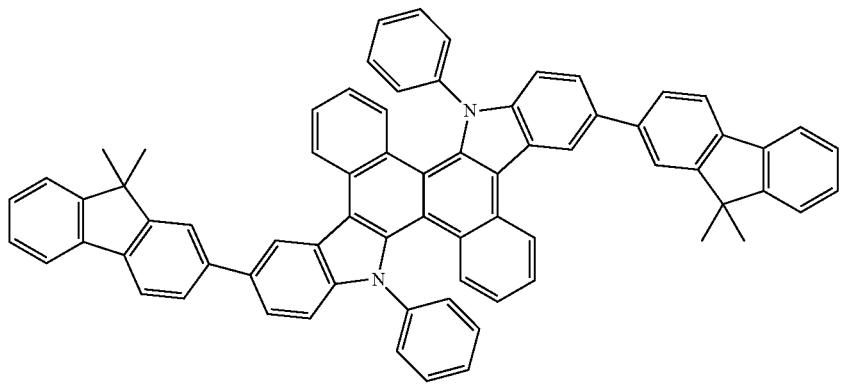

10. An organic light-emitting device comprising:
  a first electrode;
  a second electrode; and
  an organic layer between the first electrode and the second electrode, the organic layer comprising the heterocyclic compound of claim 1.

11. The organic light-emitting device of claim 10, the organic layer comprising an emission layer comprising the heterocyclic compound of Formula 1 as a host for a fluorescence or phosphorescence device.

12. The organic light-emitting device of claim 10, the organic layer comprising an emission layer comprising the heterocyclic compound of claim 1 as a dopant for a fluorescence device.

13. The organic light-emitting device of claim 10, the organic layer comprising an electron injection layer or an electron transport layer.

14. The organic light-emitting device of claim 10, the organic layer comprising a single layer having both an electron injection function and an electron transport function.

15. The organic light-emitting device of claim 10, the organic layer comprising at least one layer of an emission layer, an electron injection layer and an electron transport layer;
  at least one of said at least one layer of the emission layer, the electron injection layer and the electron transport layer comprising the heterocyclic compound of Formula 1; and
  the emission layer comprising an anthracene compound, an arylamine compound, or a styryl compound.

16. The organic light-emitting device of claim 10:
  the organic layer comprising at least one layer of an emission layer, an electron injection layer and an electron transport layer;
  at least one of said at least one layer of the emission layer, the electron injection layer and the electron transport layer comprising the heterocyclic compound of Formula 1; and
  the emission layer comprising red, green, blue, and white emission layers, one of which comprises a phosphorescent compound.

17. An organic light-emitting device comprising:
  a first electrode;
  a second electrode; and
  an organic layer between the first electrode and the second electrode,
  the organic layer comprising at least one layer comprising the heterocyclic compound of claim 1, the at least one layer being formed using a wet process.

18. A flat panel display device comprising the organic light-emitting device of claim 10, the first electrode of the organic light-emitting device being electrically connected to a source electrode or a drain electrode of a thin-film transistor.

19. The organic light-emitting device comprising:
  a first electrode;
  a second electrode; and
  an organic layer between the first electrode and the second electrode, the organic layer comprising one of the compounds below:

-continued
| | |
|---|---|
| 1 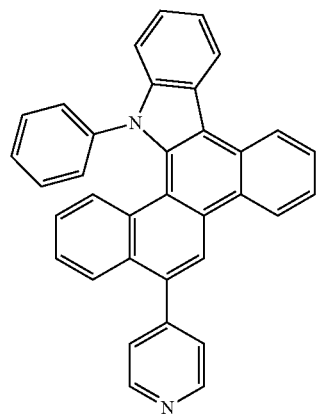 | 4 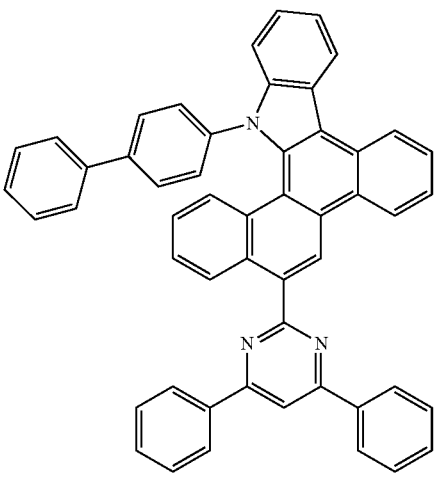 |
| 2 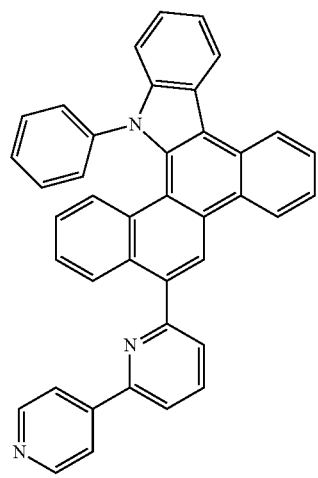 | 5 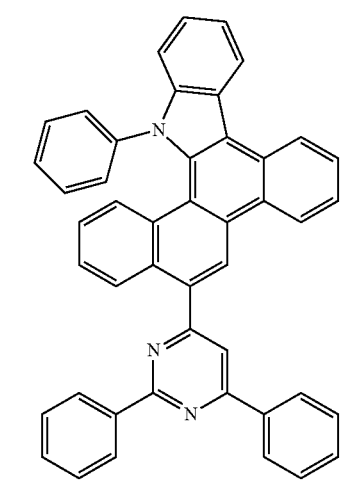 |
| 3 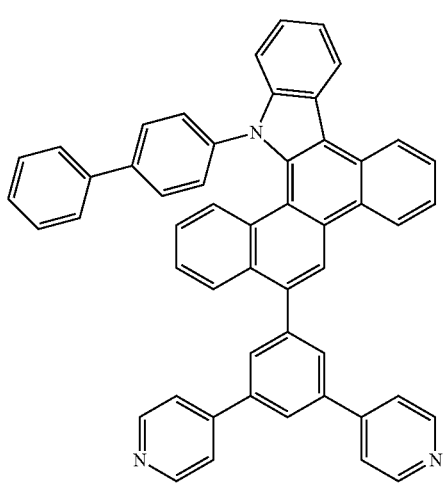 | 6 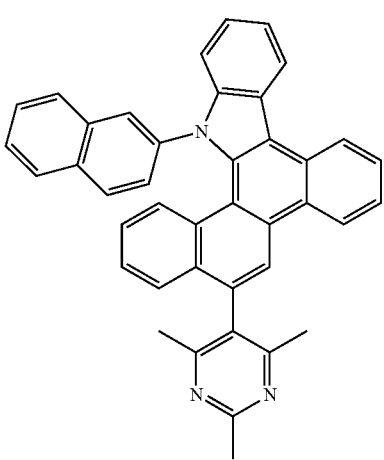 |

-continued
8
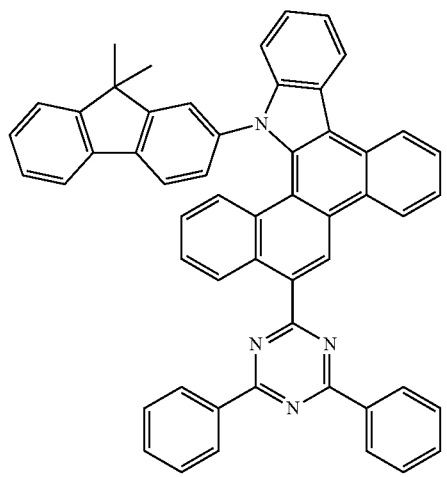
9
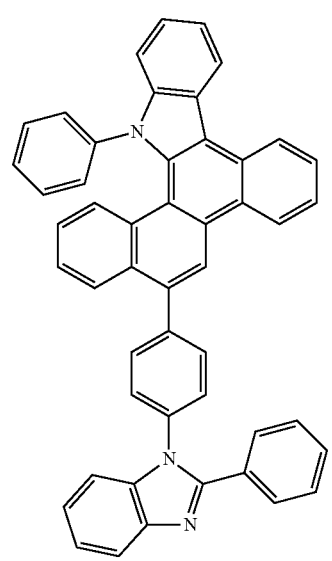
10
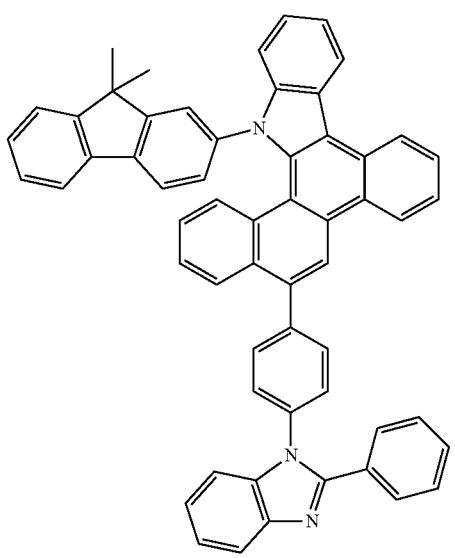
-continued
11
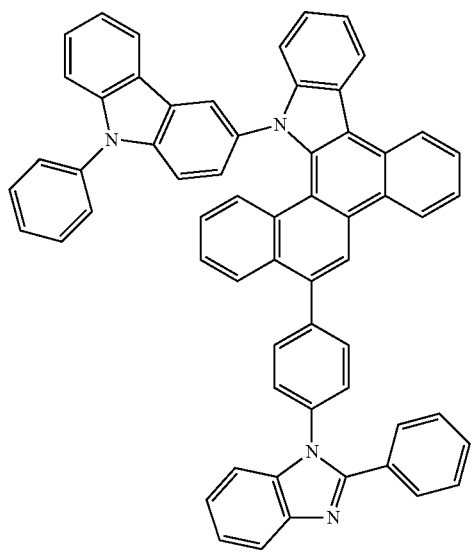
12
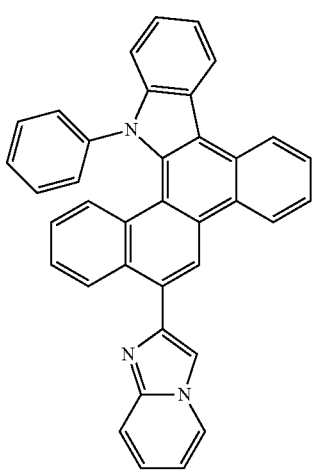
13
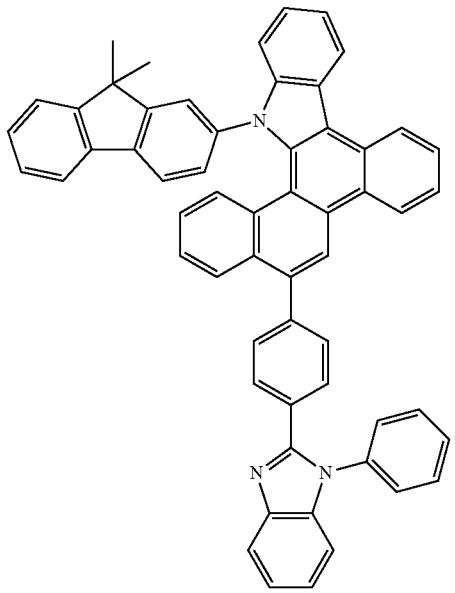

119
-continued
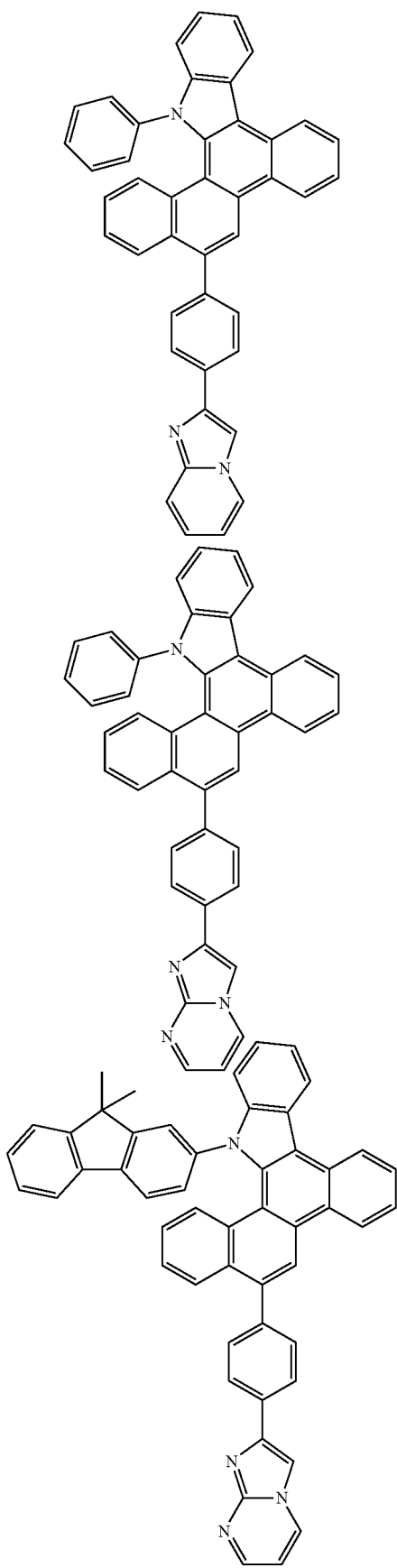
120
-continued
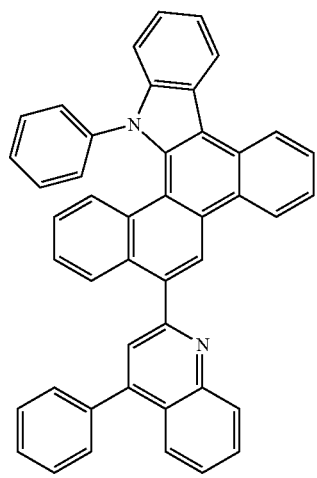
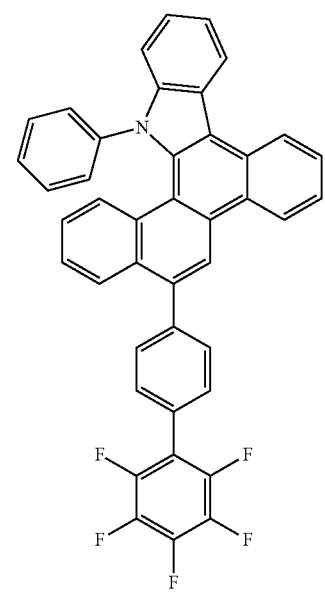
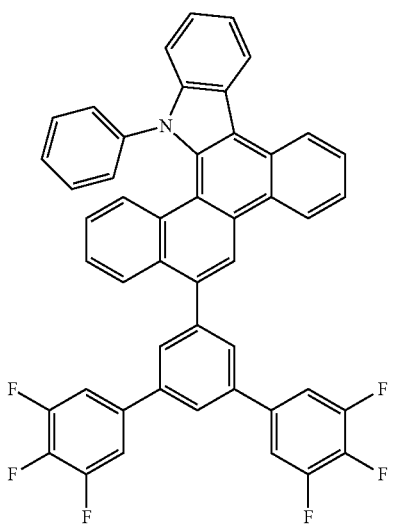

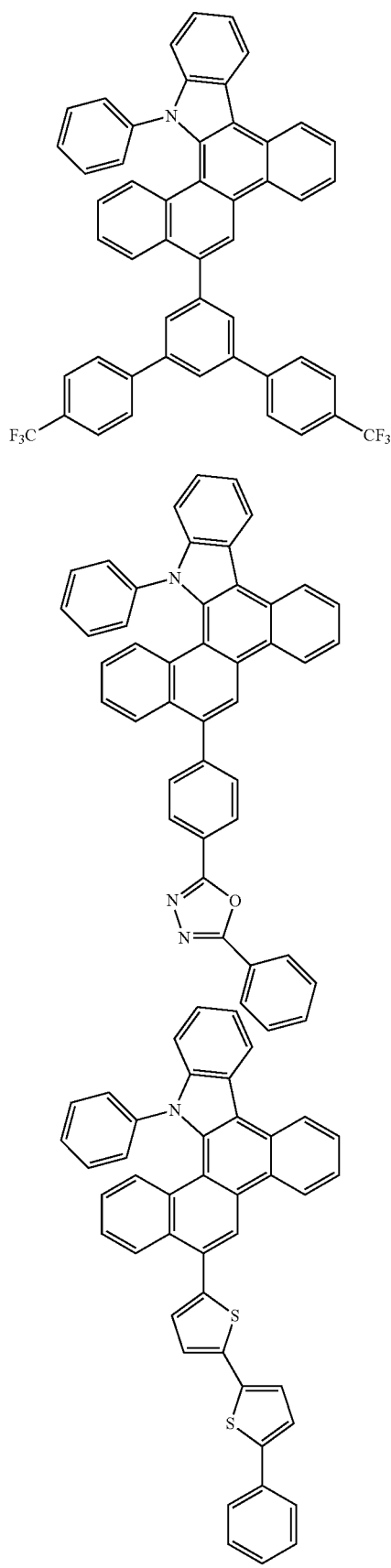
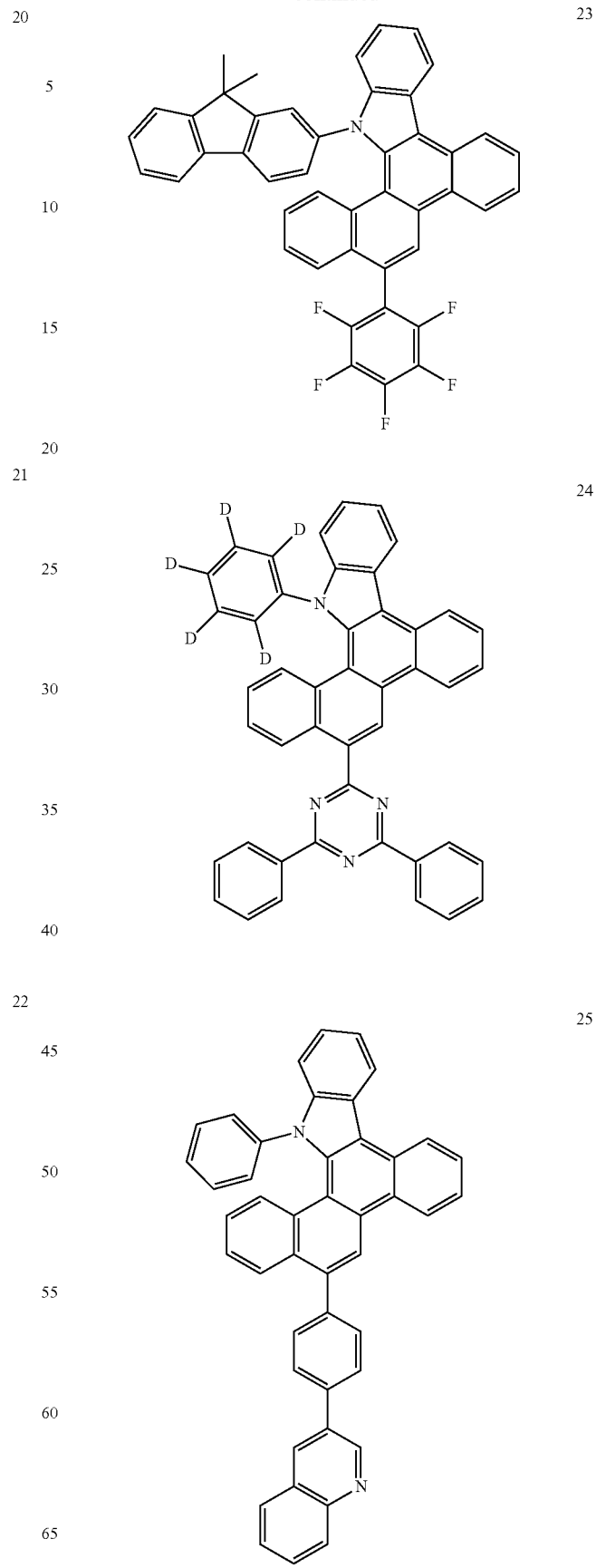

26
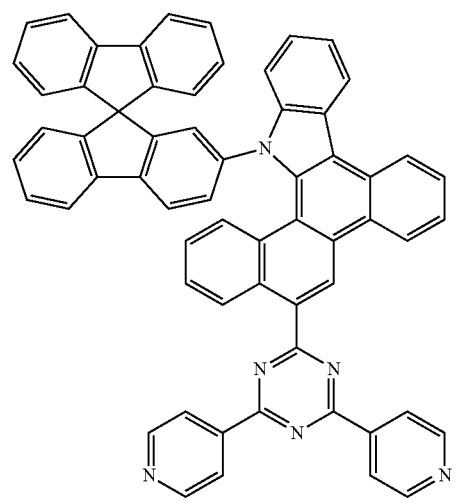
27
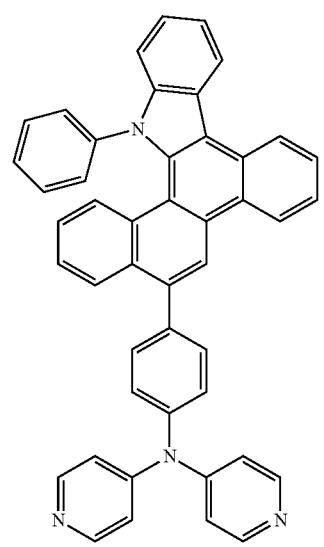
28
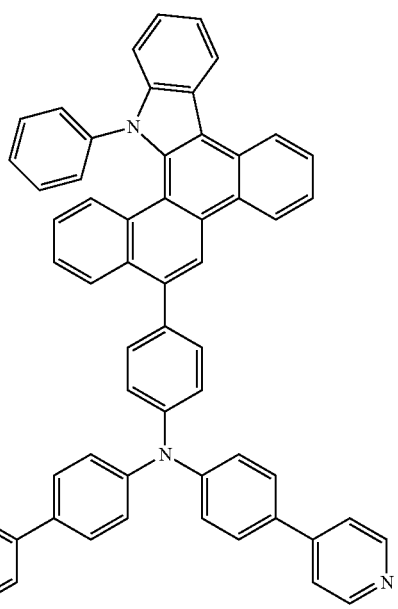
29
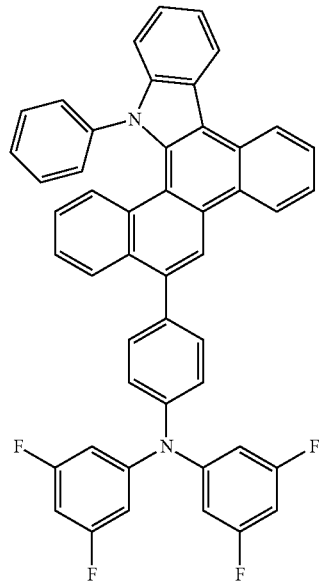
30
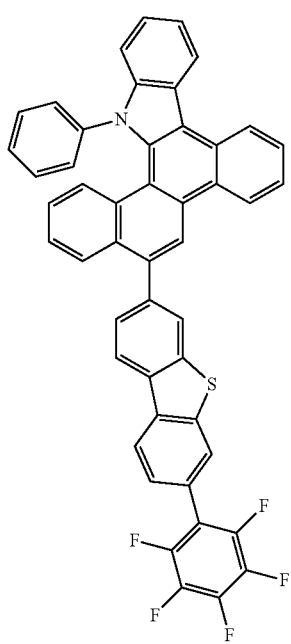

31
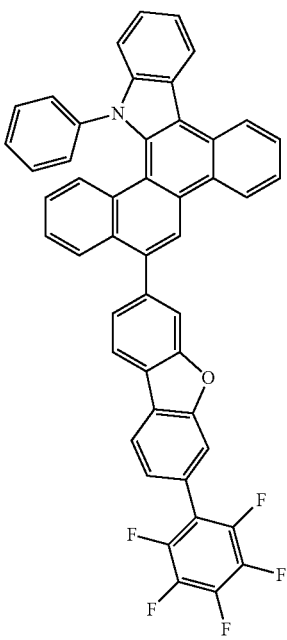
32
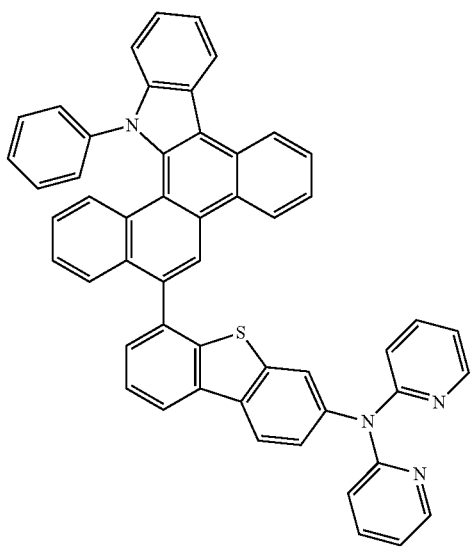
33
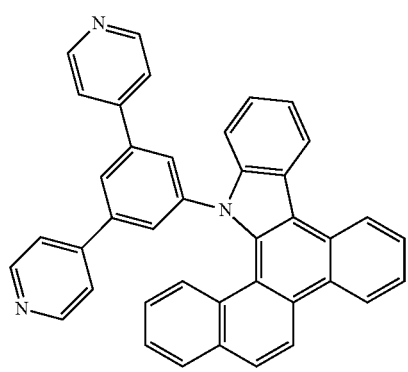
34
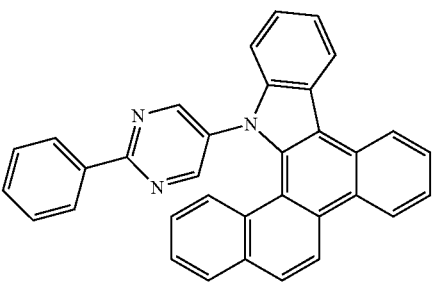
35
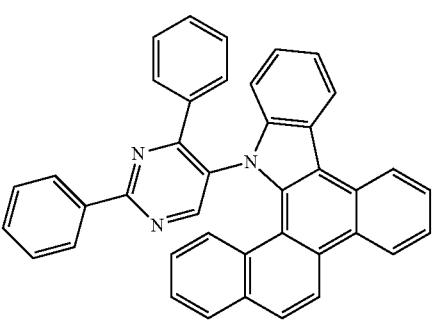
36
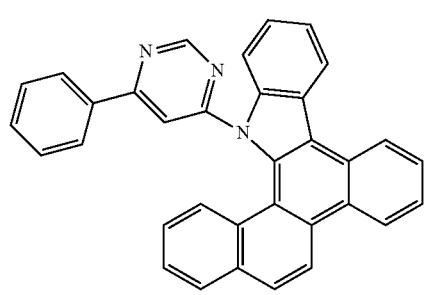
37
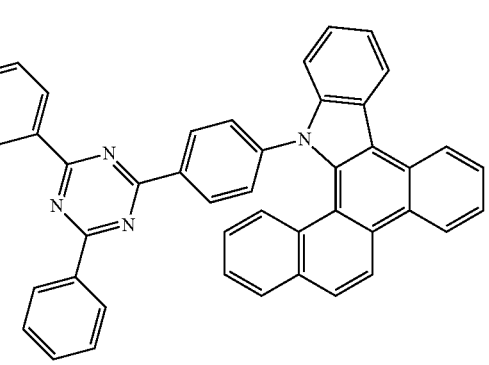
38
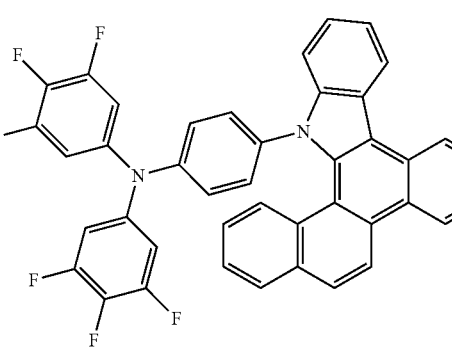

39
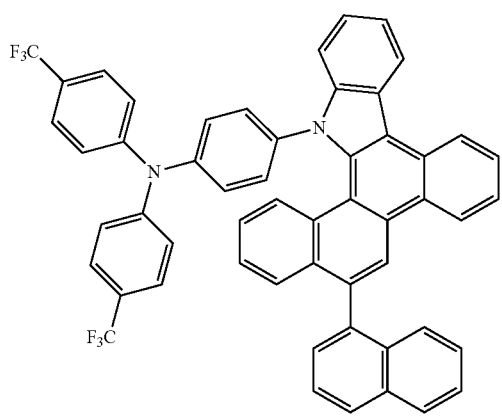
40
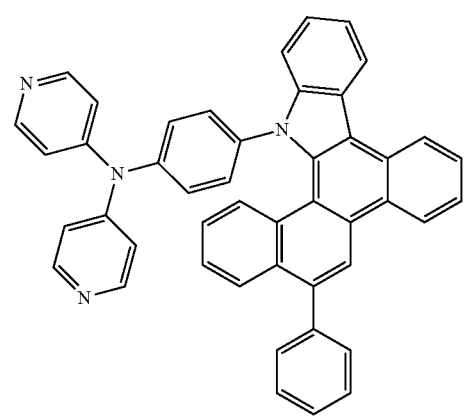
41
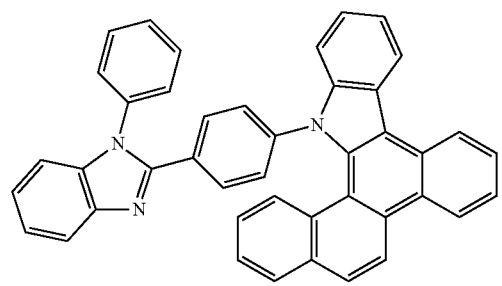
42
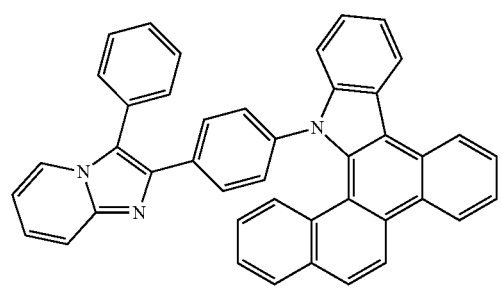
43
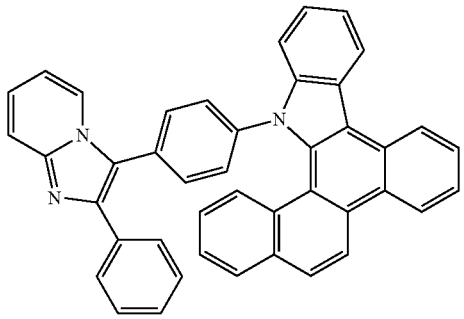
44
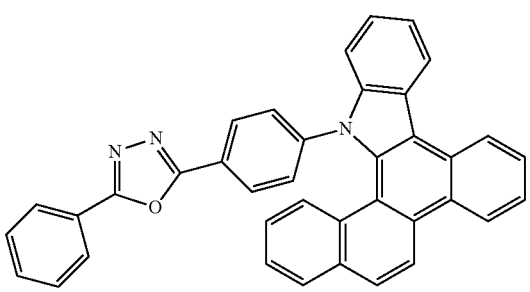
45
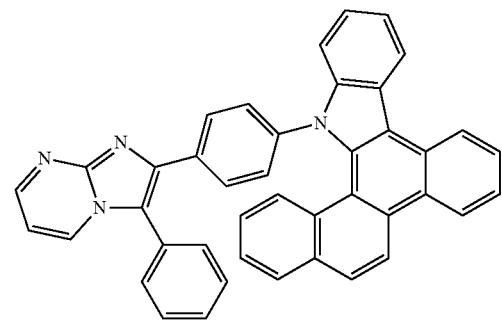
46
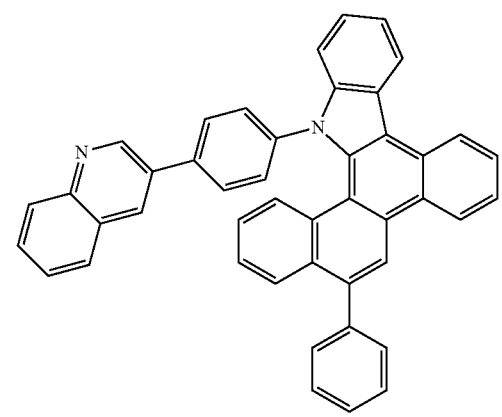

-continued
47
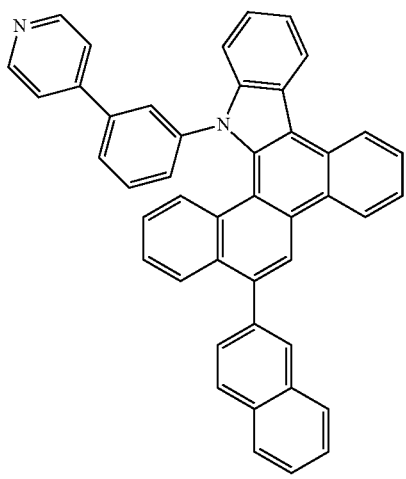
48
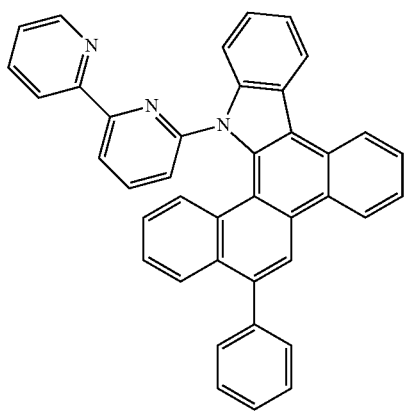
49
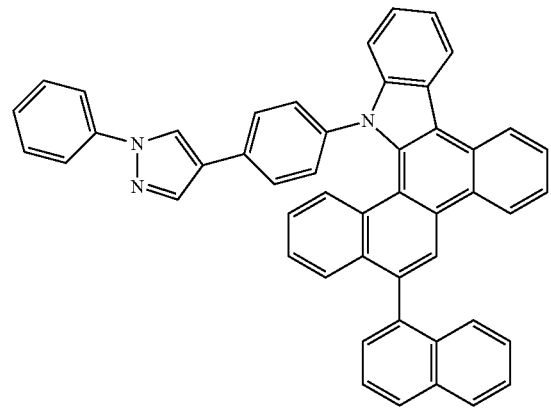
-continued
50
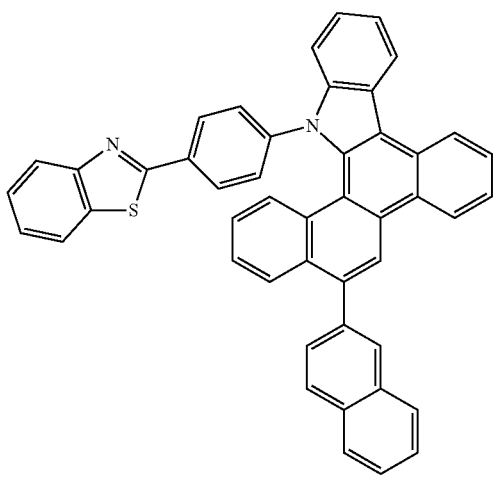
51
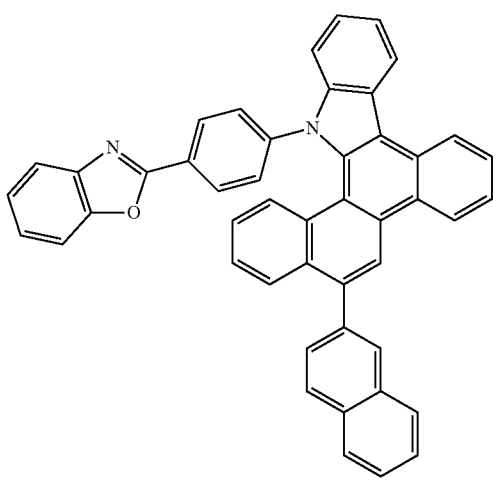
52
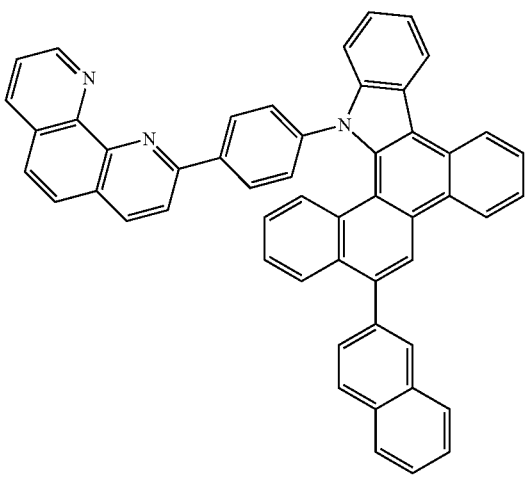

53
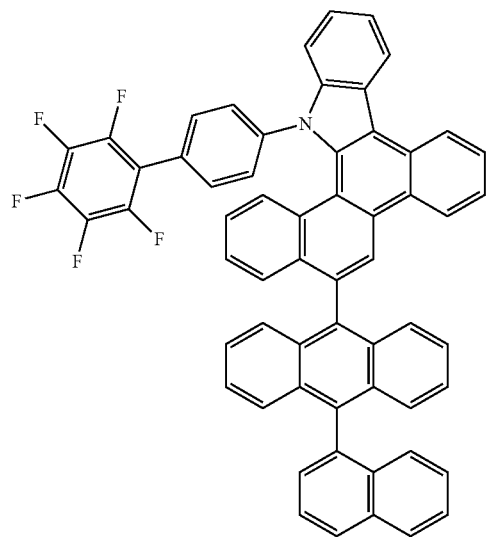
54
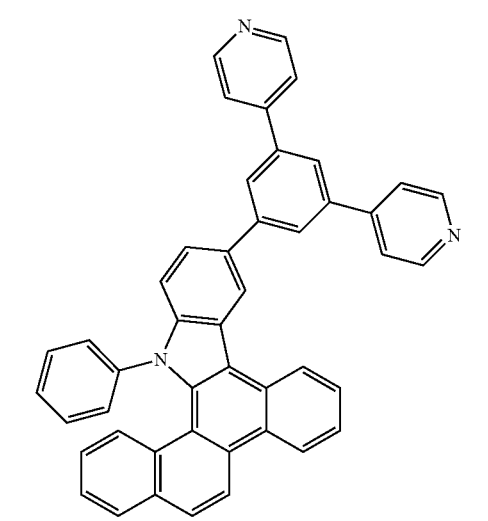
55
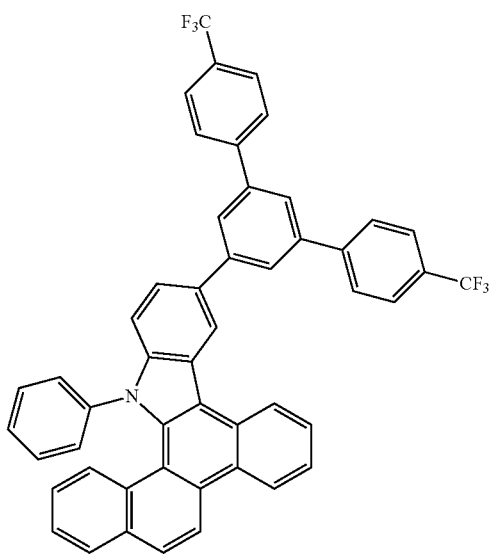
56
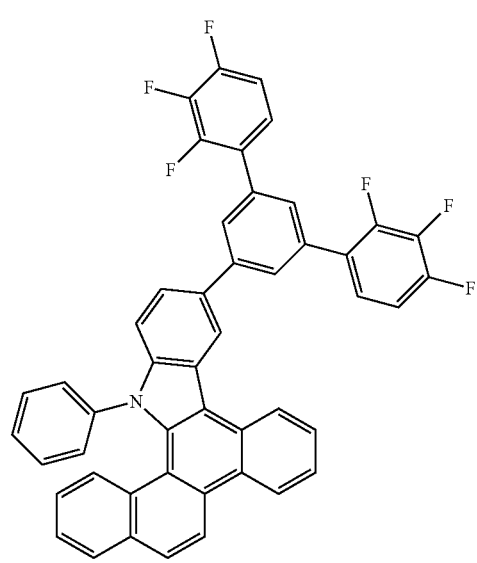
57
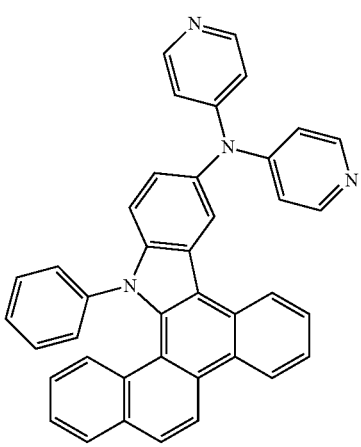
58
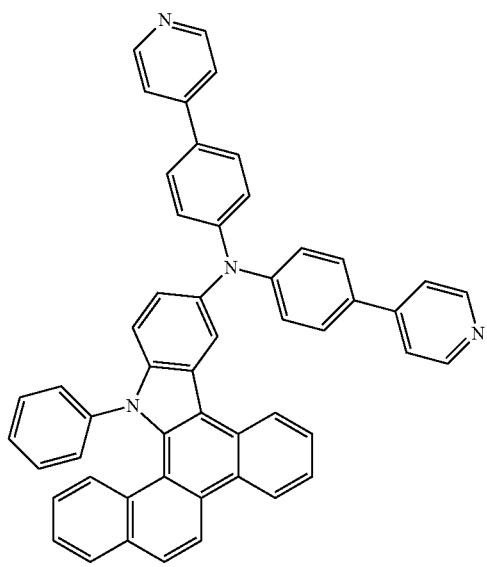

59
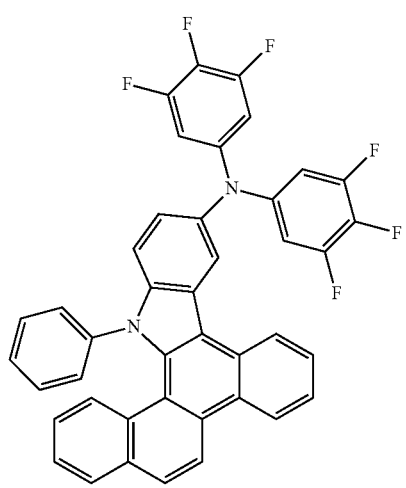
60
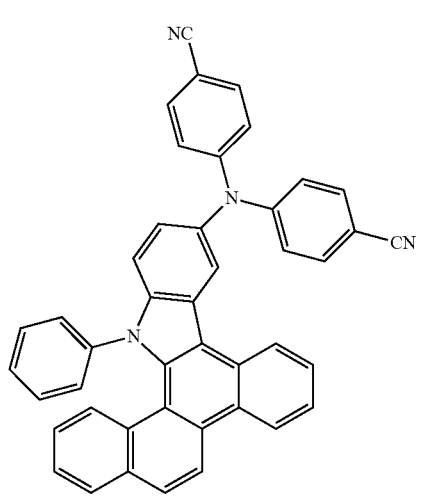
61
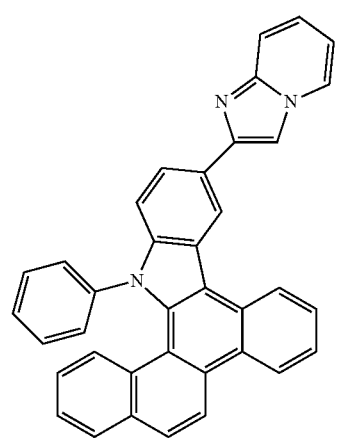
62
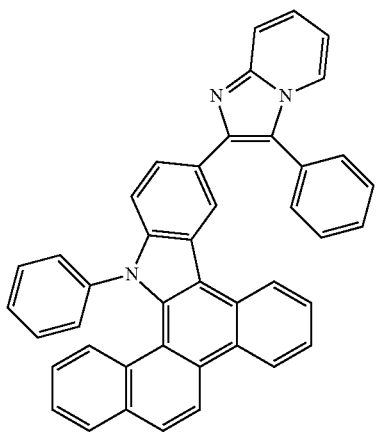
63
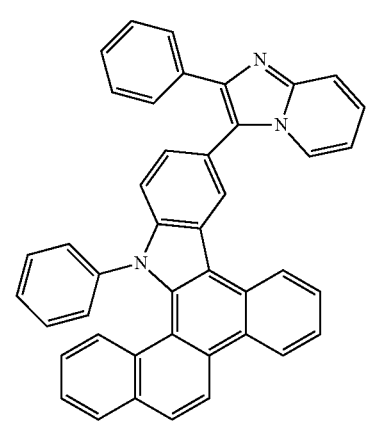
64
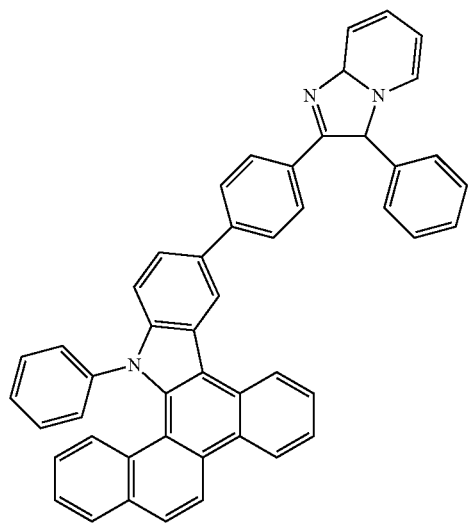

65
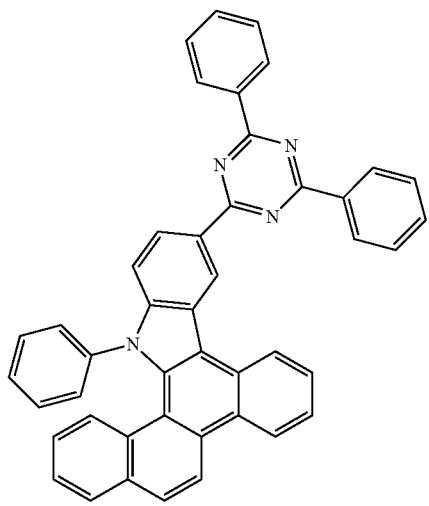
66
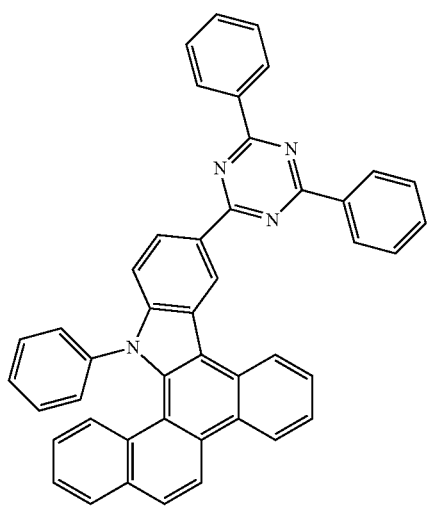
67
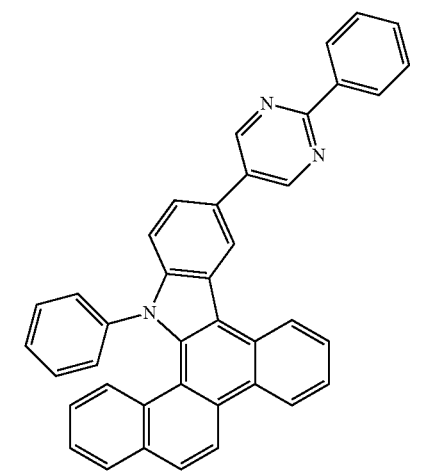
68
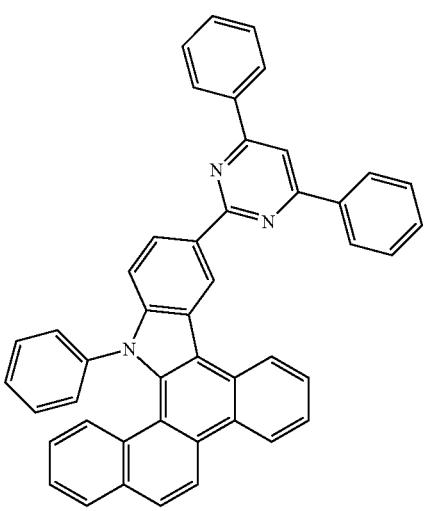
69
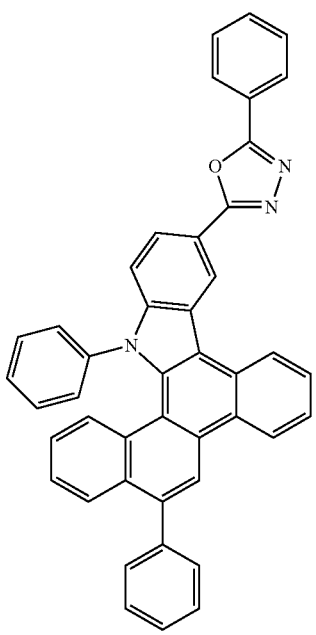
70
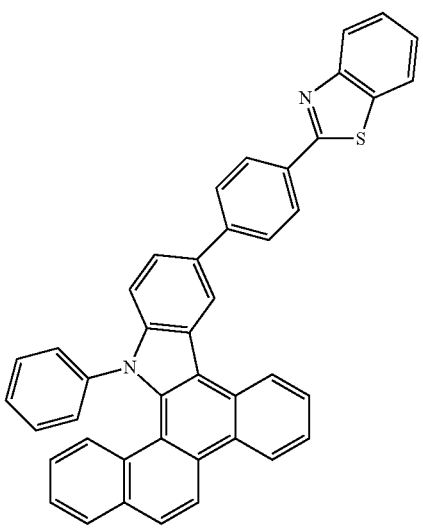

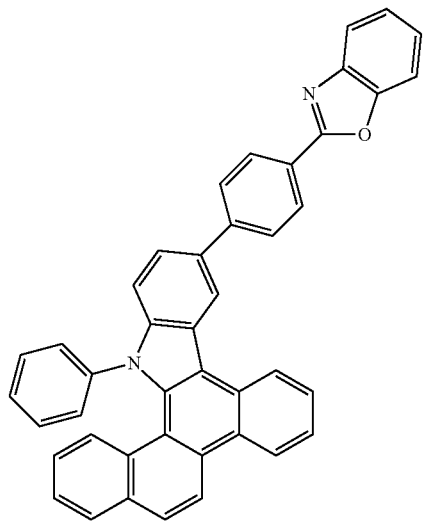
71
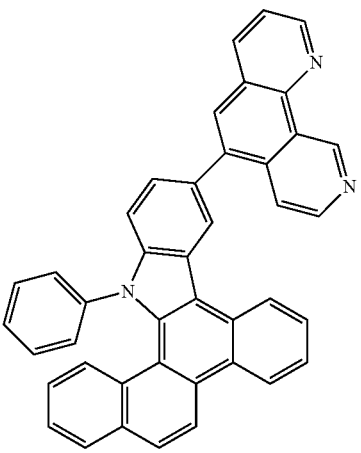
74
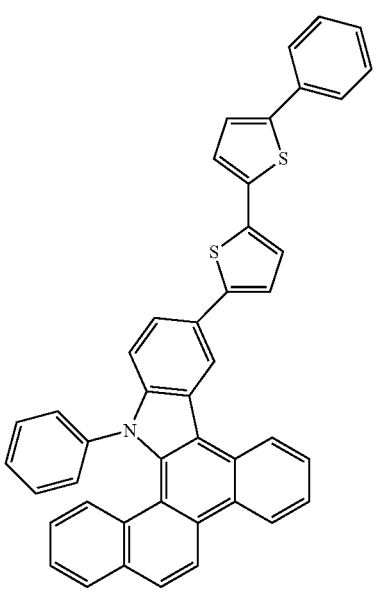
75
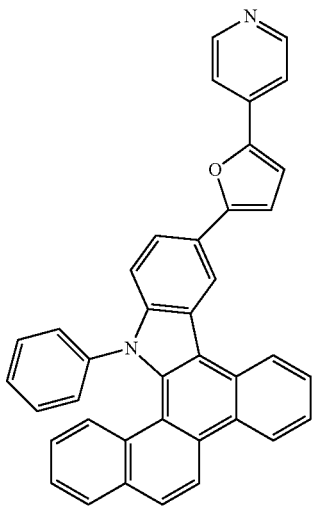
76

77
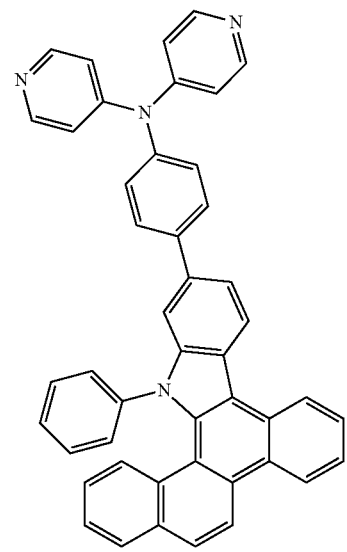
78
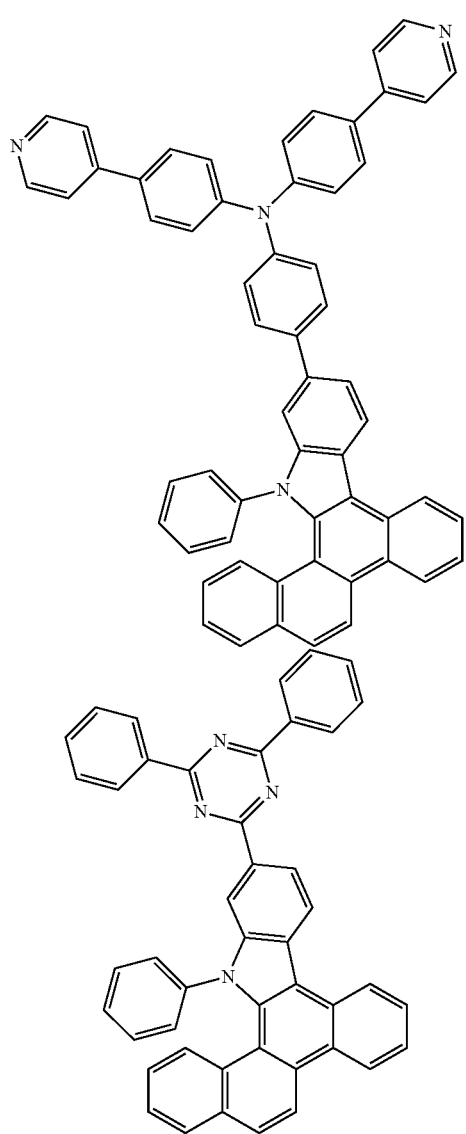
79
80
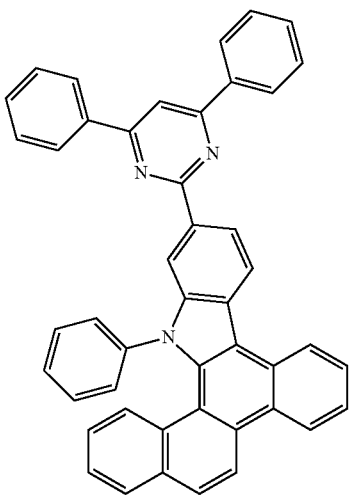
81
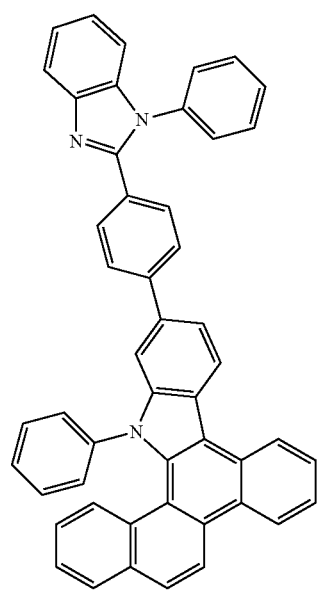
82
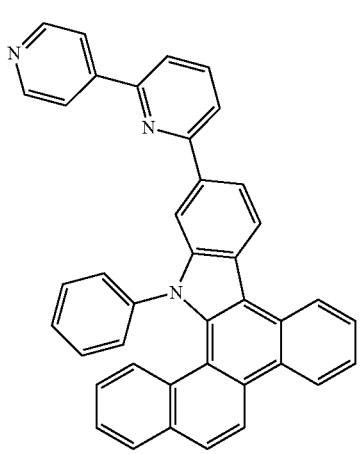

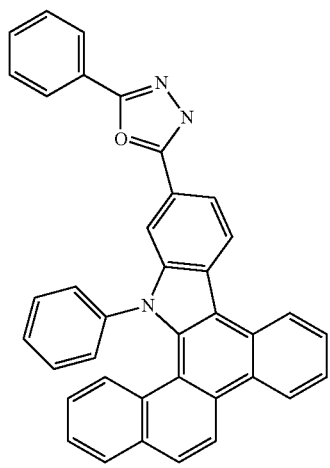
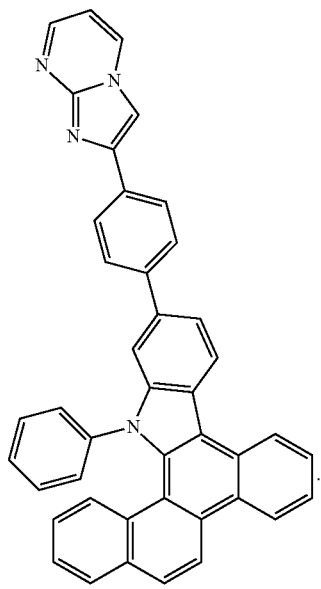
20. The organic light-emitting device of claim 10, the heterocyclic compound of claim 1 being one of the compounds below:
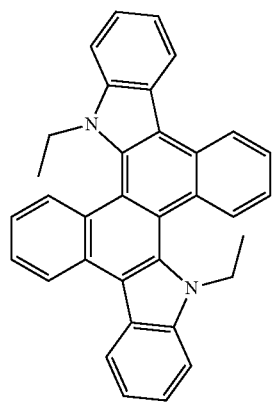
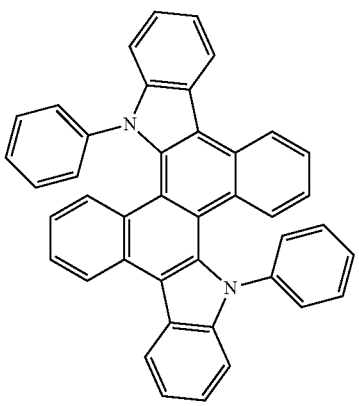
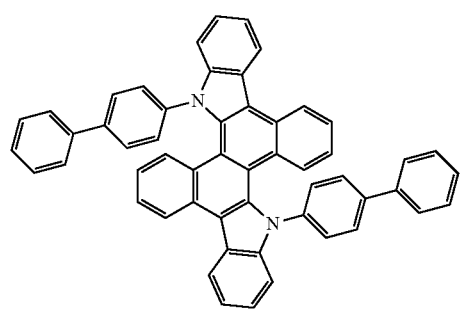
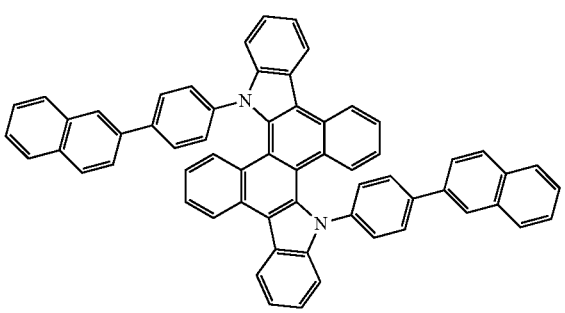

89
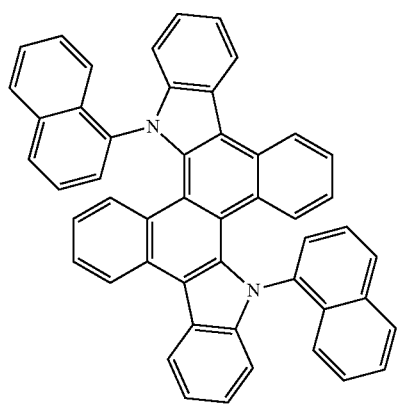
90
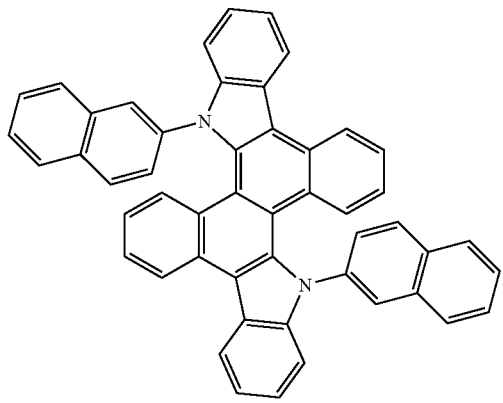
91
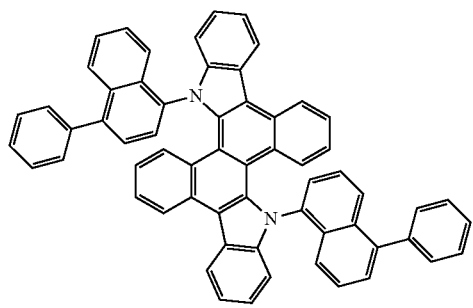
92
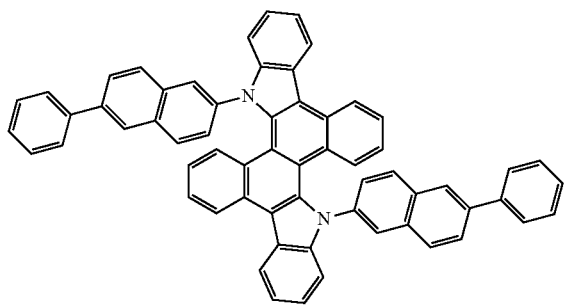
93
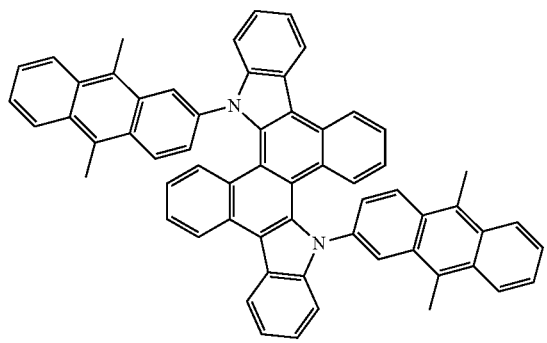
94
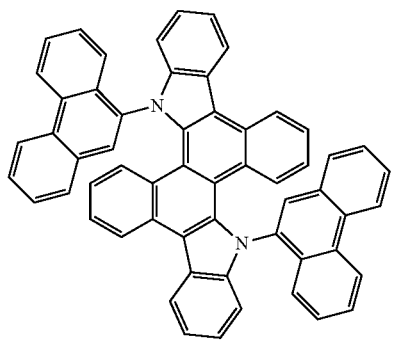
95
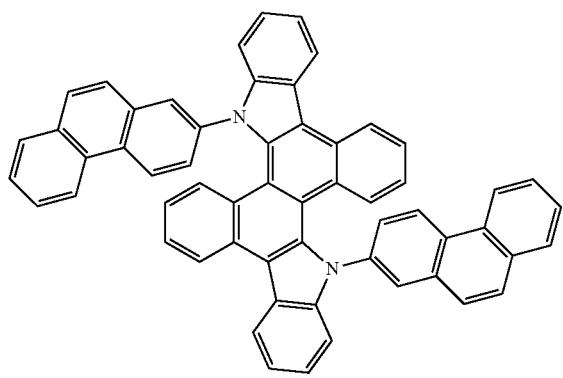
96
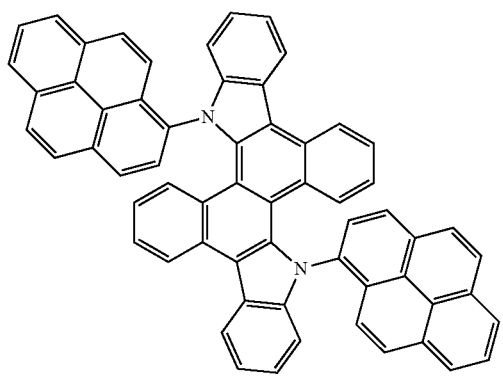

-continued
97
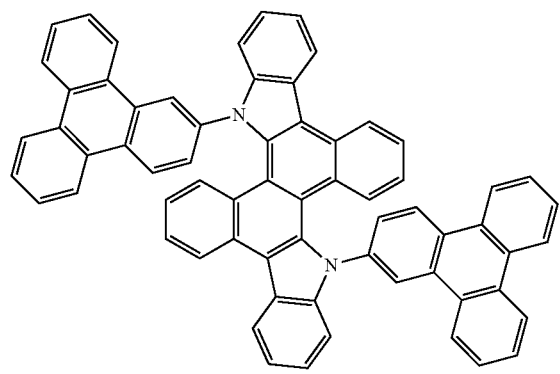
98
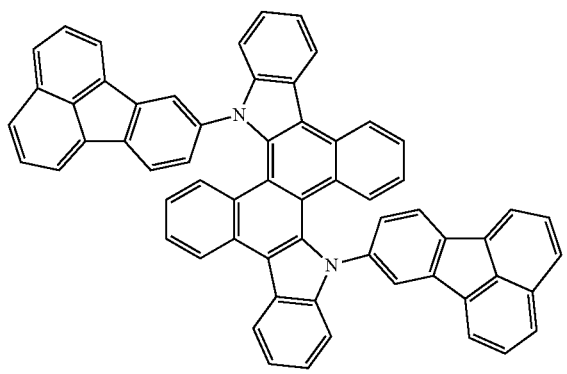
99
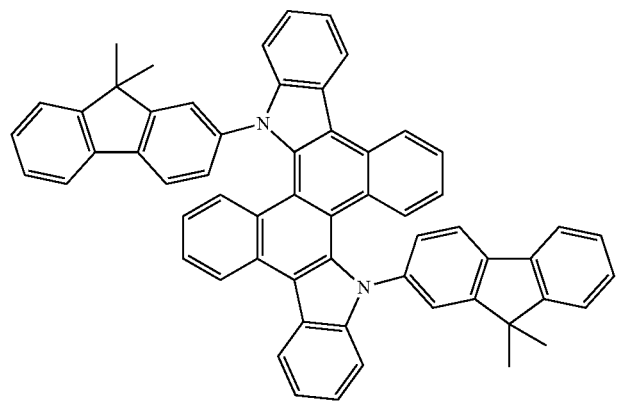
100
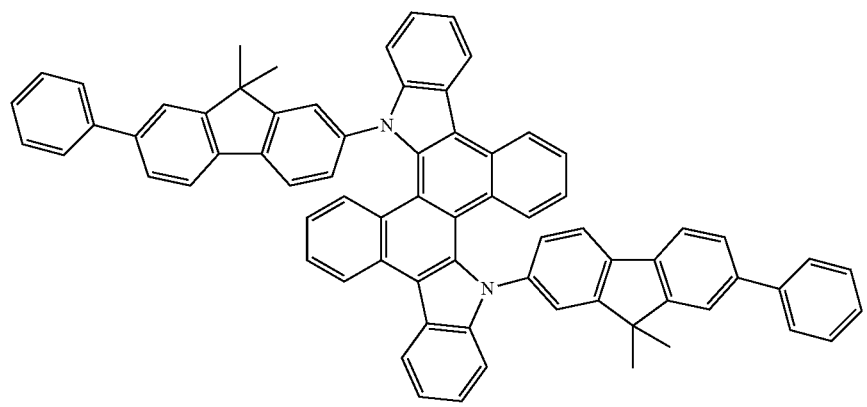
101
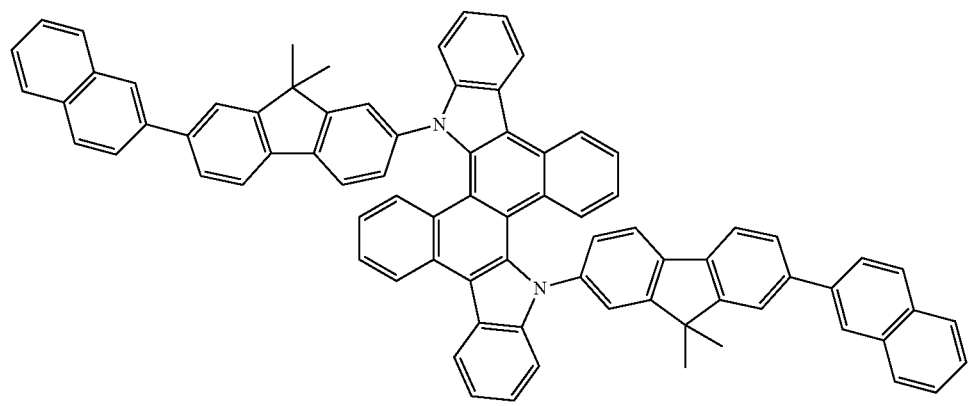

-continued
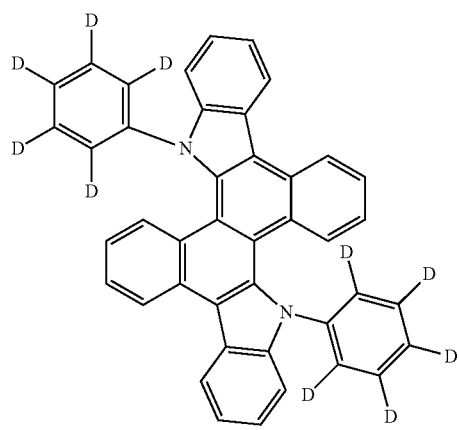
102
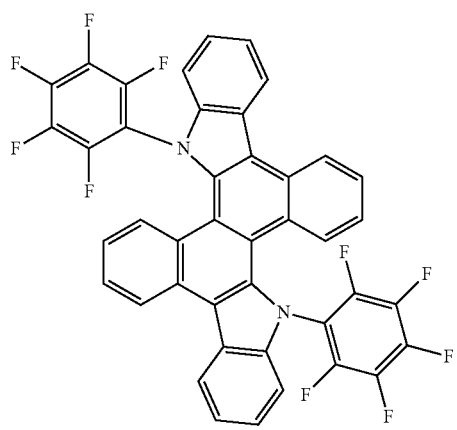
103
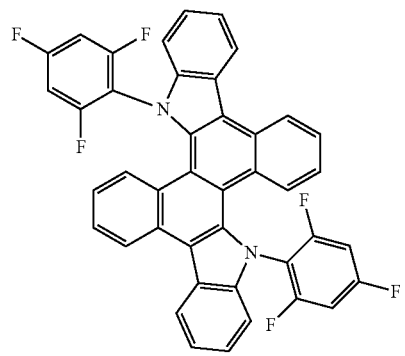
104
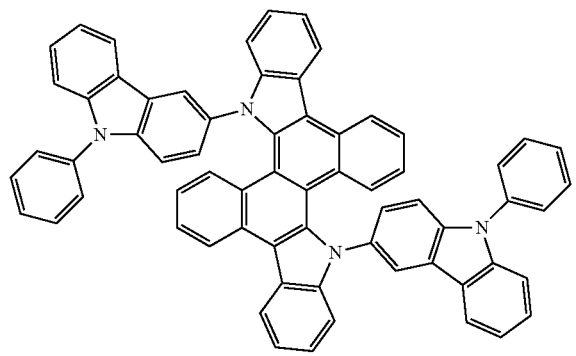
105
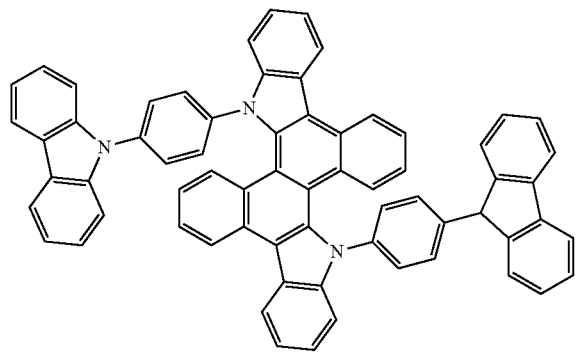
106
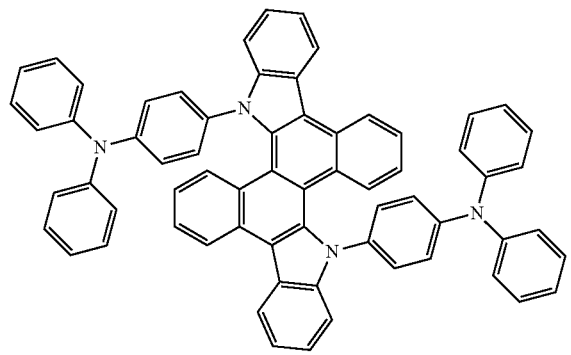
107
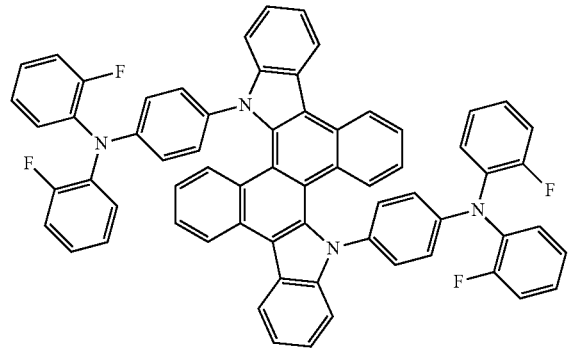
108
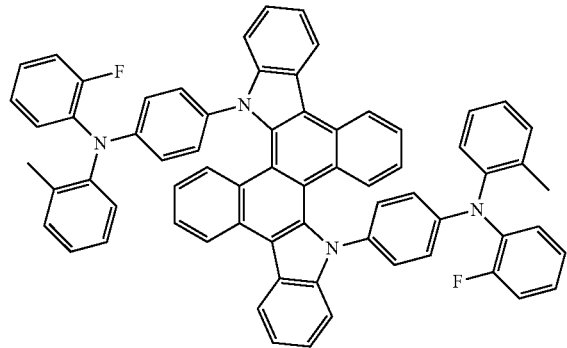
109

-continued
110
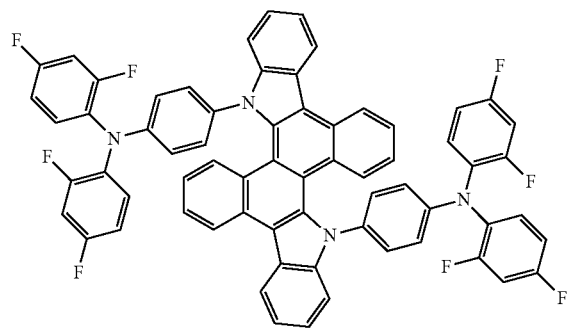
111
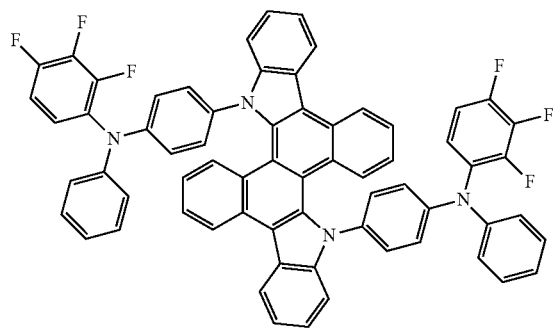
112
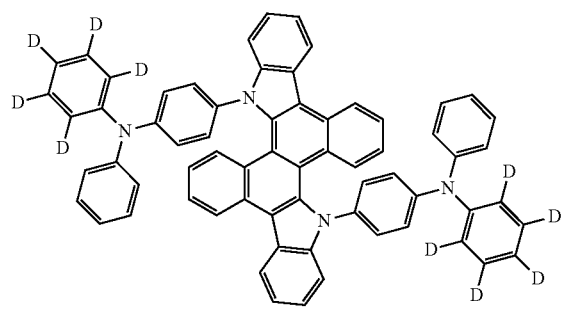
113
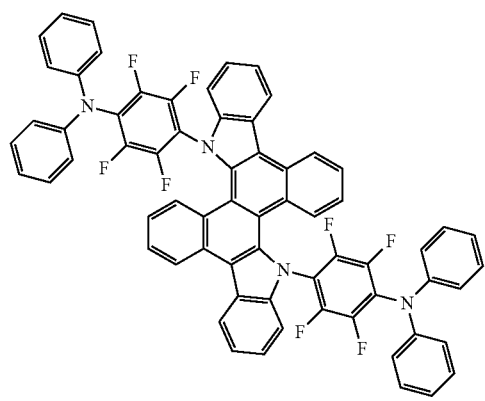
114
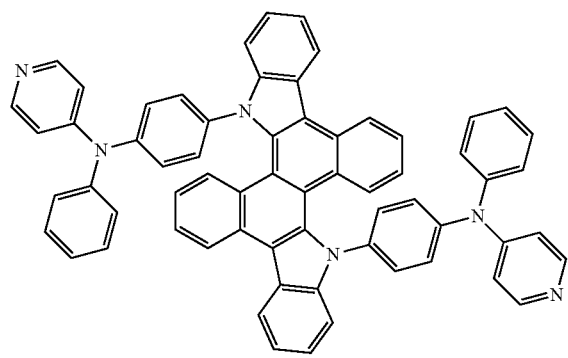
115
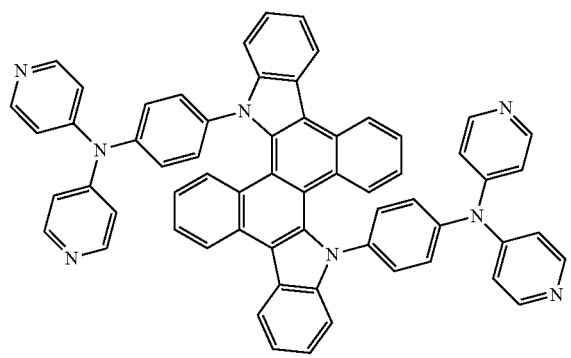

-continued
116
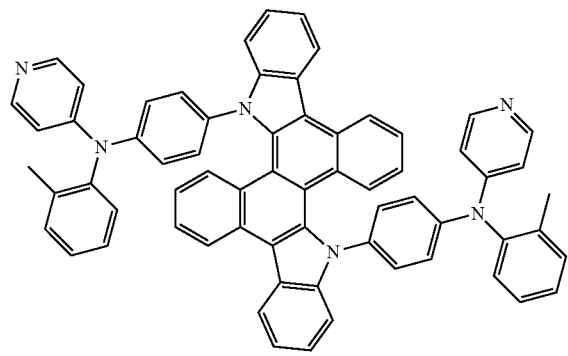
117
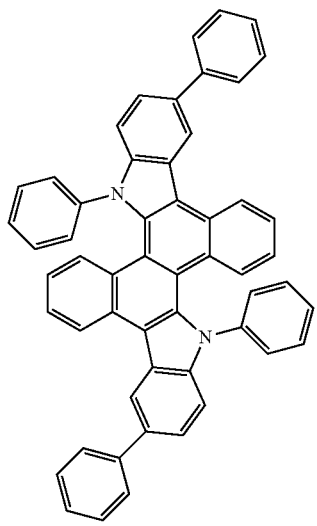
118
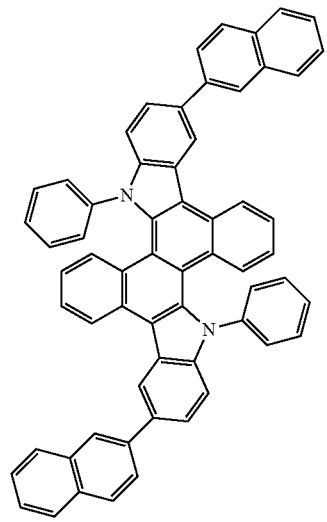
119
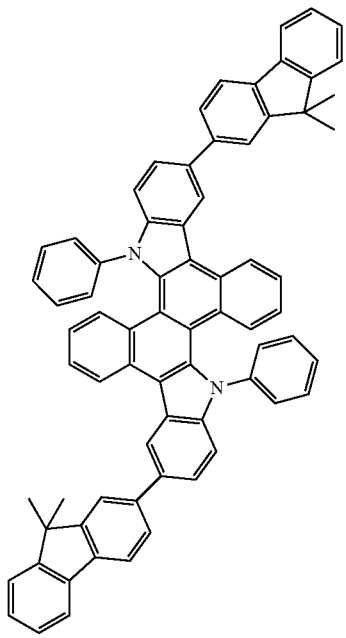

-continued
120
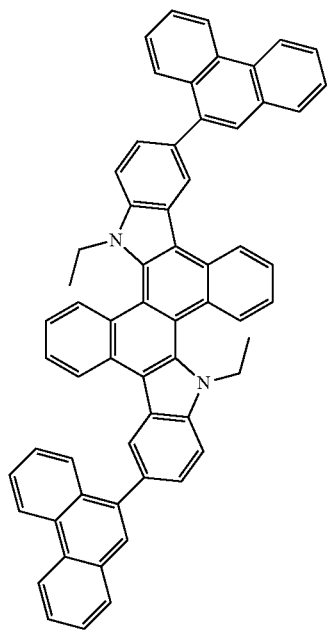
121
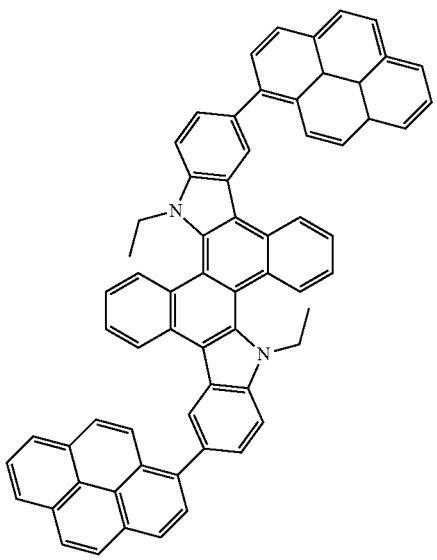
122
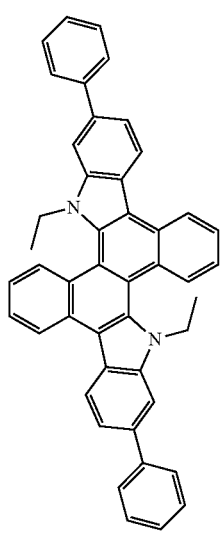
123
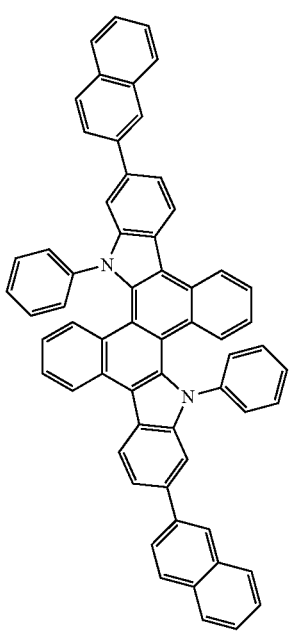

-continued

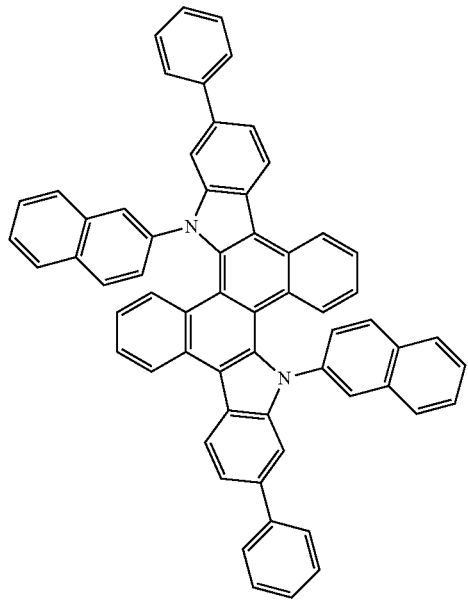

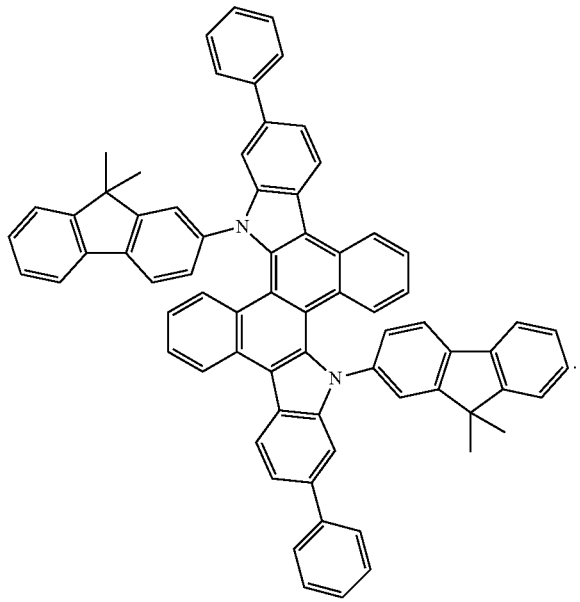

21. The heterocyclic compound of claim 1:
$R_1$ in Formula 1 being independently selected from substituted or unsubstituted $C_5$-$C_{30}$ nonheteroaromatic aryl group;
$R_{12}$ and in Formula 1 being independently selected from a hydrogen atom, a deuterium atom, a substituted or unsubstituted $C_5$-$C_{30}$ aryl group and a substituted or unsubstituted $C_2$-$C_{30}$ heterocyclic group;
substituents in the aryl groups and heterocyclic groups of $R_1$ and $R_{12}$—$R_{14}$ being independently selected from a hydrogen atom, a deuterium atom, a halogen atom, trihalomethyl, a substituted or unsubstituted $C_1$-$C_{10}$ alkyl group, a substituted or unsubstituted $C_6$-$C_{20}$ aryl group, a substituted or unsubstituted $C_2$-$C_{20}$ heterocyclic group and $N(Q_{101})(Q_{102})$, where $Q_{101}$ and $Q_{102}$ are selected from a $C_6$-$C_{20}$ aryl group and a substituted or unsubstituted $C_2$-$C_{20}$ heterocyclic group;
$R_2$-$R_5$ and $R_8$-$R_{11}$ in Formula 1 being independently selected from a hydrogen atom and a deuterium atom.

* * * * *